US012779044B2

(12) United States Patent
Klement

(10) Patent No.: US 12,779,044 B2
(45) Date of Patent: Nov. 3, 2026

(54) PLATELET-FACILITATED DELIVERY OF THERAPEUTIC COMPOUNDS

(71) Applicant: Longitude Therapeutics S.r.l., Milan (IT)

(72) Inventor: Giannoula Lakka Klement, Toronto (CA)

(73) Assignee: Longitude Therapeutics S.R.L. (IT)

( * ) Notice: Subject to any disclaimer, the term of this patent is extended or adjusted under 35 U.S.C. 154(b) by 1224 days.

(21) Appl. No.: 17/581,706

(22) Filed: Jan. 21, 2022

(65) Prior Publication Data

US 2022/0218833 A1 Jul. 14, 2022

Related U.S. Application Data

(63) Continuation of application No. PCT/IB2020/000630, filed on Jul. 23, 2020.

(60) Provisional application No. 62/877,459, filed on Jul. 23, 2019.

(51) Int. Cl.

| | |
|---|---|
| ***A61K 47/64*** | (2017.01) |
| ***A61K 35/19*** | (2015.01) |
| ***A61K 47/69*** | (2017.01) |
| ***A61P 35/00*** | (2006.01) |
| ***C07K 7/06*** | (2006.01) |

(52) U.S. Cl.

CPC .............. *A61K 47/64* (2017.08); *A61K 35/19* (2013.01); *A61K 47/6901* (2017.08); *A61P 35/00* (2018.01); *C07K 7/06* (2013.01)

(58) Field of Classification Search

CPC ..... A61K 47/6901; A61K 35/19; A61K 47/64

See application file for complete search history.

(56) References Cited

U.S. PATENT DOCUMENTS

| | | | |
|---|---|---|---|
| 5,759,542 | A | 6/1998 | Gurewich |
| 6,942,639 | B2 | 9/2005 | Baugh et al. |
| 8,512,697 | B2 | 8/2013 | Fischer et al. |
| 2004/0175374 | A1 | 9/2004 | Wolkers et al. |
| 2005/0272161 | A1 | 12/2005 | Nichols et al. |
| 2012/0156184 | A1 | 6/2012 | Prochazka et al. |
| 2013/0315828 | A1 | 11/2013 | Chang et al. |
| 2015/0004099 | A1 | 1/2015 | Salanti et al. |
| 2015/0250822 | A1 | 9/2015 | Klement et al. |
| 2017/0016905 | A1 | 1/2017 | Salanti et al. |
| 2018/0235894 | A1 | 8/2018 | Gu et al. |

FOREIGN PATENT DOCUMENTS

| | | | |
|---|---|---|---|
| CN | 108136023 | A | 6/2018 |
| EP | 0771211 | A4 | 11/1997 |
| JP | H0610250 | U | 2/1994 |
| JP | H0752117 | Y2 | 11/1995 |
| WO | WO-9207935 | A1 | 5/1992 |
| WO | WO-9604004 | A1 | 2/1996 |
| WO | WO-2010019263 | A2 | 2/2010 |
| WO | WO-2010059541 | A1 | 5/2010 |
| WO | WO-2010115866 | A1 | 10/2010 |
| WO | WO-2014055949 | A1 | 4/2014 |
| WO | WO-2016187708 | A1 | 12/2016 |
| WO | WO-2016187711 | A1 | 12/2016 |
| WO | WO-2017027760 | A1 | 2/2017 |

OTHER PUBLICATIONS

Chen et al (Advanced Healthcare Materials, 2018, article 1800424, 11 pages) (Year: 2018).*

Butterfield et al.: Identification and Sequence Composition Characterization of Chondroitin Sulfate-Binding Peptides through Peptide Array Screening. Biochemistry. 49(7):1549-1555 (2010).

Chinese Patent Application No. 2020800654733 First Office Action dated Jun. 24, 2024.

EP20844844.9 European Search Report dated Oct. 23, 2023.

Korean Application No. 10-2022-7005977 Office Action dated Aug. 20, 2023.

Ambrosio et al.: Mechanism of platelet aα-granule biogenesis: study of cargo transport and the VPS33B-VPS16B complex in a model system. Blood Adv. 3(17): 2617-2626 (2019).

Dixon et al.: Highly Efficient Delivery of Functional Cargoes by the Synergistic Effect of GAG Binding Motifs and Cell-penetrating Peptides. Proc Natl Acad Sci U S A. 113(3): E291-E299 (2016).

High, K.A.: The leak stops here: platelets as delivery vehicles for coagulation factors. J Clin Invest. 116(7): 1840-1842 (2006).

PCT/IB2020/000630 International Preliminary Report on Patentability mailed Feb. 3, 2022.

PCT/IB2020/000630 International Search Report and Written Opinion mailed Nov. 30, 2020.

Hamad et al.: Contribution of Chondroitin Sulfate A to the Binding of Complement Proteins to Activated Platelets. PLoS ONE. 5(e12889):1-10 (2010).

JP2022-504588 Notice of Allowance dated Feb. 9, 2026.

Ward, J V, and M A Packham. Characterization of the Sulfated Glycosaminoglycan on the Surface and in the Storage Granules of Rabbit Platelets. Biochimica Biophys Acta 583(2):196-207 (1979).

* cited by examiner

*Primary Examiner* — Karen A. Canella

(74) *Attorney, Agent, or Firm* — Wilson Sonsini Goodrich & Rosati

(57) ABSTRACT

The present disclosure provides compositions and methods comprising platelets loaded with an agent. Agents loaded into platelets are generally protected from degradation and the subject is protected from toxicity, if any, from the agent. These benefits, coupled with the platelets' natural ability to home to sites of injury, inflammation, and/or angiogenesis, helps ensure that a therapeutically-effective amount of the agent is delivered to a target site.

21 Claims, 20 Drawing Sheets

Specification includes a Sequence Listing.

FIG. 3E

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 1.16E+05 | -2.48E+03 | 1.48E+01 | 4.37E+03 | -6.85E+03 |
| 2 | 1.69E+04 | -1.70E+03 | 1.36E+01 | 4.01E+03 | -5.71E+03 |
| 3 | 5.55E+03 | -1.81E+02 | 1.65E+01 | 4.87E+03 | -5.05E+03 |
| 4 | 2.66E+03 | -1.98E+03 | 8.95E+00 | 2.64E+03 | -4.63E+03 |
| 5 | 1.27E+04 | 1.62E+03 | 2.43E+01 | 7.17E+03 | -5.55E+03 |
| 6 | 9.03E+03 | 1.63E+04 | 7.33E+01 | 2.16E+04 | -5.34E+03 |
| 7 | 1.20E+05 | 2.67E+04 | 1.14E+02 | 3.36E+04 | -6.96E+03 |
| 8 | 8.43E+03 | -1.04E+05 | -3.34E+02 | -9.86E+04 | -5.22E+03 |
| sum | 2.91E+05 | -6.55E+04 | -6.86E+01 | -2.02E+04 | -4.53E+04 |
| average | 3.64E+04 | -8.19E+03 | -8.57E+00 | -2.53E+03 | -5.66E+03 |
| average kd | 2.75E-05 | | | | |

FIG. 3F

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 1.23E+05 | -2.77E+03 | 1.39E+01 | 4.10E+03 | -6.88E+03 |
| 2 | 1.52E+04 | -1.69E+03 | 1.34E+01 | 3.96E+03 | -5.64E+03 |
| 3 | 4.56E+02 | -3.82E+03 | -7.58E-01 | -2.24E+02 | -3.59E+03 |
| 4 | 2.76E+03 | -1.31E+04 | -2.87E+01 | -8.47E+03 | -4.65E+03 |
| 5 | 2.06E+04 | 1.10E+04 | 5.71E+01 | 1.69E+04 | -5.82E+03 |
| 6 | 2.91E+04 | 7.02E+04 | 2.58E+02 | 7.61E+04 | -5.93E+03 |
| 7 | 3.26E+04 | -7.54E+04 | -2.35E+02 | -6.94E+04 | -6.05E+03 |
| sum | 2.24E+05 | -1.56E+04 | 7.79E+01 | 2.30E+04 | -3.86E+04 |
| average | 3.20E+04 | -2.22E+03 | 1.11E+01 | 3.29E+03 | -5.51E+03 |
| average kd | 3.13E-05 | | | | |

FIG. 7D

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 3.93E+05 | -1.20E+03 | 2.15E+01 | 6.35E+03 | -7.54E+03 |
| 2 | 3.13E+05 | -5.79E+02 | 2.32E+01 | 6.85E+03 | -7.43E+03 |
| 3 | 6.27E+03 | -1.63E+03 | 1.19E+01 | 3.51E+03 | -5.14E+03 |
| sum | 7.12E+05 | -3.41E+03 | 5.66E+01 | 1.67E+04 | -2.01E+04 |
| average | 2.37E+05 | -1.14E+03 | 1.89E+01 | 5.57E+03 | -6.70E+03 |
| Average Kd ($M^{-1}$) | 4.21E-06 | | | | |

FIG. 7E

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 2.28E+05 | -1.11E+03 | 2.08E+01 | 6.14E+03 | -7.24E+03 |
| 2 | 6.09E+04 | -1.67E+03 | 1.62E+01 | 4.78E+03 | -6.46E+03 |
| 3 | 1.11E+05 | 1.30E+03 | 2.75E+01 | 8.12E+03 | -6.81E+03 |
| sum | 4.00E+05 | -1.48E+03 | 6.45E+01 | 1.90E+04 | -2.05E+04 |
| average | 1.33E+05 | -4.92E+02 | 2.15E+01 | 6.35E+03 | -6.84E+03 |
| Average Kd ($M^{-1}$) | 7.50E-06 | | | | |

FIG. 7F

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 1.62E+03 | -1.51E+04 | -3.66E+01 | -1.08E+04 | -4.33E+03 |
| 2 | 1.14E+04 | 1.55E+04 | 7.12E+01 | 2.10E+04 | -5.48E+03 |
| sum | 1.30E+04 | 4.00E+02 | 3.46E+01 | 1.02E+04 | -9.81E+03 |
| average | 6.51E+03 | 2.00E+02 | 1.73E+01 | 5.11E+03 | -4.91E+03 |
| Average Kd ($M^{-1}$) | 1.54E-04 | | | | |

FIG. 9B

| 3 mM CSA titrated in mNeon-PAL1A at 22°C | | | | | |
|---|---|---|---|---|---|
| binding site | Ka ($M^{-1}$) | ΔH (kcal/mol) | ΔS (kcal/mol/degree) | T ΔS (kcal/mol) | ΔG (kcal/mol) |
| 1 | 2.06E+03 | -7.13E+03 | -8.98E+00 | -2.65E+03 | -4.48E+03 |
| 2 | 3.15E+04 | -1.77E+03 | 1.46E+01 | 4.31E+03 | -6.08E+03 |
| 3 | 1.66E+04 | 8.58E+03 | 4.84E+01 | 1.43E+04 | -5.71E+03 |
| sum | 5.02E+04 | -3.21E+02 | 5.40E+01 | 1.59E+04 | -1.63E+04 |
| average | 1.67E+04 | -1.07E+02 | 1.80E+01 | 5.31E+03 | -5.42E+03 |
| average kd ($M^{-1}$) | 5.98E-05 | | | | |

FIG. 9C

| binding site | Ka ($M^{-1}$) | ΔH (kcal/mol) | ΔS (kcal/mol/degree) | T ΔS (kcal/mol) | ΔG (kcal/mol) |
|---|---|---|---|---|---|
| 1 | 1.02E+04 | -2.76E+03 | 8.99E+00 | 2.65E+03 | -5.41E+03 |
| 2 | 6.62E+04 | -6.46E+02 | 1.99E+01 | 5.87E+03 | -6.52E+03 |
| 3 | 1.99E+03 | 4.33E+03 | 2.97E+01 | 8.77E+03 | -4.44E+03 |
| sum | 7.84E+04 | 9.22E+02 | 5.86E+01 | 1.73E+04 | -1.64E+04 |
| average | 2.61E+04 | 3.07E+02 | 1.95E+01 | 5.76E+03 | -5.46E+03 |
| average kd ($M^{-1}$) | 3.83E-05 | | | | |

FIG. 9D

| binding site | Ka ($M^{-1}$) | ΔH (kcal/mol) | ΔS (kcal/mol/degree) | T ΔS (kcal/mol) | ΔG (kcal/mol) |
|---|---|---|---|---|---|
| 1 | 1.91E+05 | -1.17E+03 | 2.02E+01 | 5.96E+03 | -7.14E+03 |
| 2 | 1.10E+04 | -1.64E+03 | 1.29E+01 | 3.81E+03 | -5.44E+03 |
| 3 | 1.12E+04 | 1.25E+03 | 2.28E+01 | 6.73E+03 | -5.48E+03 |
| sum | 2.13E+05 | -1.56E+03 | 5.59E+01 | 1.65E+04 | -1.81E+04 |
| average | 7.11E+04 | -5.21E+02 | 1.86E+01 | 5.50E+03 | -6.02E+03 |
| average kd ($M^{-1}$) | 1.41E-05 | | | | |

FIG. 9E

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 9.78E+03 | -3.19E+03 | 7.44E+00 | 2.20E+03 | -5.39E+03 |
| 2 | 5.00E+04 | -7.69E+02 | 1.89E+01 | 5.58E+03 | -6.35E+03 |
| 3 | 2.99E+03 | 3.02E+03 | 2.61E+01 | 7.70E+03 | -4.68E+03 |
| sum | 6.28E+04 | -9.44E+02 | 5.24E+01 | 1.55E+04 | -1.64E+04 |
| average | 2.09E+04 | -3.15E+02 | 1.75E+01 | 5.16E+03 | -5.47E+03 |
| average kd ($M^{-1}$) | 4.78E-05 | | | | |

FIG. 9F

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 4.85E+04 | -1.36E+03 | 1.68E+01 | 4.96E+03 | -6.32E+03 |
| 2 | 2.74E+04 | -1.03E+03 | 1.68E+01 | 4.96E+03 | -5.99E+03 |
| 3 | 5.81E+03 | 1.87E+03 | 2.36E+01 | 6.97E+03 | -5.09E+03 |
| sum | 8.17E+04 | -5.23E+02 | 5.72E+01 | 1.69E+04 | -1.74E+04 |
| average | 2.72E+04 | -1.74E+02 | 1.91E+01 | 5.63E+03 | -5.80E+03 |
| average kd ($M^{-1}$) | 3.67E-05 | | | | |

FIG. 9G

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 1.25E+06 | -7.66E+02 | 2.53E+01 | 7.47E+03 | -8.23E+03 |
| 2 | 1.05E+05 | -5.46E+02 | 2.11E+01 | 6.23E+03 | -6.77E+03 |
| 3 | 8.60E+00 | -1.70E+03 | -1.48E+00 | -4.37E+02 | -1.26E+03 |
| sum | 1.36E+06 | -3.01E+03 | 4.49E+01 | 1.33E+04 | -1.63E+04 |
| average | 4.52E+05 | -1.00E+03 | 1.50E+01 | 4.42E+03 | -5.42E+03 |
| average kd ($M^{-1}$) | 2.21E-06 | | | | |

FIG. 9H

| binding site | Ka ($M^{-1}$) | ΔH (kcal/mol) | ΔS (kcal/mol/degree) | T·ΔS (kcal/mol) | ΔG (kcal/mol) |
|---|---|---|---|---|---|
| 1 | 2.90E+02 | -1.62E+04 | -4.35E+01 | -1.28E+04 | -3.32E+03 |
| 2 | 1.26E+03 | 2.88E+04 | 1.12E+02 | 3.31E+04 | -4.31E+03 |
| 3 | 4.17E+03 | -1.83E+04 | -4.55E+01 | -1.34E+04 | -4.90E+03 |
| sum | 5.72E+03 | -5.74E+03 | 2.30E+01 | 6.79E+03 | -1.25E+04 |
| average | 1.91E+03 | -1.91E+03 | 7.67E+00 | 2.26E+03 | -4.18E+03 |
| average kd ($M^{-1}$) | 5.24E-04 | | | | |

FIG. 9I

| binding site | Ka ($M^{-1}$) | ΔH (kcal/mol) | ΔS (kcal/mol/degree) | TΔS (kcal/mol) | ΔG (kcal/mol) |
|---|---|---|---|---|---|
| 1 | 6.06E+04 | -7.85E+02 | 1.92E+01 | 5.67E+03 | -6.45E+03 |
| 2 | 1.41E+04 | -2.05E+03 | 1.20E+01 | 3.54E+03 | -5.59E+03 |
| 3 | 3.04E+04 | 1.87E+03 | 2.68E+01 | 7.91E+03 | -6.04E+03 |
| sum | 1.05E+05 | -9.66E+02 | 5.80E+01 | 1.71E+04 | -1.81E+04 |
| average | 3.50E+04 | -3.22E+02 | 1.93E+01 | 5.71E+03 | -6.03E+03 |
| average kd ($M^{-1}$) | 2.85E-05 | | | | |

FIG. 9J

| binding site | Ka ($M^{-1}$) | ΔH (kcal/mol) | ΔS (kcal/mol/degree) | TΔS (kcal/mol) | ΔG (kcal/mol) |
|---|---|---|---|---|---|
| 1 | 3.77E+04 | -1.78E+03 | 1.49E+01 | 4.40E+03 | -6.18E+03 |
| 2 | 1.37E+04 | -2.10E+03 | 1.18E+01 | 3.48E+03 | -5.58E+03 |
| 3 | 5.61E+03 | 3.11E+03 | 2.77E+01 | 8.18E+03 | -5.07E+03 |
| sum | 5.70E+04 | -7.76E+02 | 5.44E+01 | 1.61E+04 | -1.68E+04 |
| average | 1.90E+04 | -2.59E+02 | 1.81E+01 | 5.35E+03 | -5.61E+03 |
| average kd ($M^{-1}$) | 5.26E-05 | | | | |

FIG. 9K

| binding site | Ka ($M^{-1}$) | ΔH (kcal/mol) | ΔS (kcal/mol/degree) | TΔS (kcal/mol) | ΔG (kcal/mol) |
|---|---|---|---|---|---|
| 1 | 3.55E+04 | -3.26E+03 | 9.79E+00 | 2.89E+03 | -6.15E+03 |
| 2 | 1.05E+05 | 4.46E+02 | 2.45E+01 | 7.23E+03 | -6.79E+03 |
| 3 | 4.62E+01 | 2.66E+04 | 9.78E+01 | 2.89E+04 | -2.26E+03 |
| sum | 1.41E+05 | 2.38E+04 | 1.32E+02 | 3.90E+04 | -1.52E+04 |
| average | 4.68E+04 | 7.93E+03 | 4.40E+01 | 1.30E+04 | -5.06E+03 |
| average kd ($M^{-1}$) | 2.13E-05 | | | | |

FIG. 9L

| binding site | Ka ($M^{-1}$) | ΔH (kcal/mol) | ΔS (kcal/mol/degree) | TΔS (kcal/mol) | ΔG (kcal/mol) |
|---|---|---|---|---|---|
| 1 | 2.47E+03 | -9.67E+03 | -1.72E+01 | -5.08E+03 | -4.60E+03 |
| 2 | 1.96E+05 | 4.81E+03 | 4.05E+01 | 1.20E+04 | -7.14E+03 |
| 3 | 3.82E+03 | 3.39E+03 | 2.79E+01 | 8.23E+03 | -4.84E+03 |
| sum | 2.02E+05 | -1.47E+03 | 5.12E+01 | 1.51E+04 | -1.66E+04 |
| average | 6.74E+04 | -4.89E+02 | 1.71E+01 | 5.04E+03 | -5.53E+03 |
| average kd ($M^{-1}$) | 1.48E-05 | | | | |

PLATELET-FACILITATED DELIVERY OF THERAPEUTIC COMPOUNDS

CROSS-REFERENCE TO RELATED APPLICATIONS

This application is a continuation of International Application No. PCT/IB2020/000630, filed Jul. 23, 2020, which claims the benefit of U.S. Provisional Patent Application No. 62/877,459, filed Jul. 23, 2019. The entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 21, 2022, is named 58533-701.301_ST25.txt and is 3,199 bytes in size.

BACKGROUND

Therapeutic compounds that are systemically administered can degrade prior to arrival to their target site; thus, if they arrive at all, their dose may be too low to achieve a therapeutic effect. Platelets naturally home to sites of injury, inflammation, and/or angiogenesis and are known to transport native cargos to these sites. If exogenous therapeutic agents could be loaded into platelets, the agents should be protected from the degradation that would occur following the agent's systemic administration. However, no mechanisms for loading exogenous, therapeutic agents into platelet's alpha granules has been described. Thus, there is an unmet need for loaded platelets that can deliver exogenous therapeutic agents to sites of injury, inflammation, and/or angiogenesis.

SUMMARY

In various aspects, the present disclosure provides platelets loaded with agents that can be delivered, in a therapeutically-effective dose, to target sites of injury, inflammation, and/or angiogenesis. In part, the present invention relates to compounds comprising at least an agent and a glycosaminoglycan (GAG)-binding peptide, with the GAG-binding peptide being useful for loading the compound into an alpha granule of a platelet. Since the agents are loaded into platelets, they are generally protected from degradation upon systemic administration. Moreover, certain agents are toxic to a subject; when loaded into platelets, toxic agents are less able to harm the subject. These benefits, coupled with platelets' natural ability to home to sites of injury, inflammation, and/or angiogenesis, help to ensure that a therapeutically-effective amount of the agent is delivered to a target site. Accordingly, the present disclosure overcomes deficiencies in current therapeutics by providing directed therapeutics, in a therapeutically-effective amount, to sites of injury (e.g., for treating chronic wounds), pathological inflammation (e.g., for treating injury to joints or lungs), and/or angiogenesis (e.g., for treating cancer).

An aspect of the present disclosure is a compound comprising a first agent and a first polypeptide. The first polypeptide comprises a glycosaminoglycan (GAG)-binding peptide which can bind a GAG in an alpha granule of a platelet.

In embodiments, the GAG-binding peptide binds to chondroitin sulfate (CS) and/or to heparan sulfate (HS). In embodiments, the GAG-binding peptide preferentially binds to CS. In embodiments, the GAG-binding peptide preferentially binds to chondroitin sulfate A (CSA).

In embodiments, the GAG-binding peptide binds to heparan sulfate (HS), serglycin, perlecan, dermatan sulfate, keratan sulfate, and/or GPIIb/IIIa. In embodiments, the GAG-binding peptide does not preferentially bind to heparan sulfate (HS), serglycin, perlecan, dermatan sulfate, keratan sulfate, and/or GPIIb/IIIa. In embodiments, the GAG-binding peptide does not bind, does not detectably bind, does not substantially bind, or binds with low affinity to HS, serglycin, perlecan, dermatan sulfate, keratan sulfate, and/or GPIIb/IIIa.

In embodiments, the GAG-binding peptide remains bound to a CS-containing column when exposed to about 1N NaCl. In embodiments, the GAG-binding peptide remains bound to a CS-containing column when exposed to about 2N NaCl. In embodiments, the GAG-binding peptide is unbound to a CS-containing column when exposed to about 3N NaCl.

In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of between about 0.001N and about 0.01N. In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 0.1N. In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 1N.

In embodiments, the GAG-binding peptide is between about 8 amino acids and about 14 amino acids in length.

In embodiments, the GAG-binding peptide comprises at least one charged amino acid.

In embodiments, the GAG-binding peptide comprises at least one proline, arginine, and/or isoleucine.

In embodiments, the GAG-binding peptide comprises an amino acid sequence that is at least about 70% identical to one of SEQ ID NO: 1 to SEQ ID NO: 13, is at least about 80% identical to one of SEQ ID NO: 1 to SEQ ID NO: 13, or is at least about 90% identical to one of SEQ ID NO: 1 to SEQ ID NO: 13.

In embodiments, the GAG-binding peptide comprises a charged amino acid at position 1, position 4, position 7, or position 9 with respect to any one of SEQ ID NO: 1 to SEQ ID NO: 13.

In embodiments, the GAG-binding peptide comprises a proline, arginine, and/or isoleucine at position 1, position 4, position 7, and/or position 9 with respect to any one of SEQ ID NO: 1 to SEQ ID NO: 13.

In embodiments, the GAG-binding peptide comprises at least 10 amino acids. In embodiments, the GAG-binding peptide comprises 11 amino acids. In embodiments, the GAG-binding peptide consists of 11 amino acids.

In embodiments, the GAG-binding peptide comprises an amino acid sequence that is at least about 90% identical to SEQ ID NO: 1 or to SEQ ID NO:2.

In embodiments, the GAG-binding peptide comprises an amino acid sequence of one of SEQ ID NO: 1 to SEQ ID NO: 13.

In embodiments, the GAG-binding peptide comprises the amino acid sequence of SEQ ID NO: 1 or SEQ ID NO:2.

In embodiments, the GAG-binding peptide consists of the amino acid sequence of one of SEQ ID NO: 1 to SEQ ID NO: 13.

In embodiments, the first polypeptide consists of the GAG-binding peptide.

Alternately, the first polypeptide may include amino acids other than the GAG-binding peptide; in some embodiments, the additional amino acids in the polypeptide do not increase affinity of the GAG-binding peptide to a GAG.

In embodiments, the N-terminal of the first polypeptide is directly or indirectly linked to the first agent. In embodiments, the C-terminal of the first polypeptide is directly or indirectly linked to the first agent. In embodiments, the first agent is indirectly linked to the first polypeptide via at least one linker. In embodiments, the at least one linker comprises one or more atoms. In embodiments, the at least one linker comprises a polymer of repeating units. In embodiments, the at least one linker comprises a chain of amino acids.

In embodiments, the first agent is directly linked to the first polypeptide.

In embodiments, the first agent is directly or indirectly linked to the first polypeptide using a maleimide reaction, succinimidyl ester reaction, an enzymatic reaction, or another conjugation systems that does not affect protein structure or activity.

In embodiments, the first agent comprises an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet. In embodiments, the first agent comprises an antibody. In embodiments, the first agent comprises a fluorescent moiety.

In embodiments, the first agent is harmful to mammalian cells and/or is toxic to a subject.

In embodiments, the first agent is susceptible to degradation when administered directly into the bloodstream of a subject.

In embodiments, the compound further comprises a fluorescent moiety.

Another aspect of the present disclosure is an isolated platelet comprising at least one copy of any herein disclosed compound.

In embodiments, the platelet is a synthetic, an allogeneic, an autologous, or a modified heterologous platelet. In embodiments, the platelet is an autologous platelet. In embodiments, the platelet is an allogeneic platelet. In embodiments, the platelet is obtained from platelet rich plasma.

In embodiments, the platelet comprises 1 to 1000 copies of the compound. In embodiments, the 1 to 1000 copies of the compound are loaded into an alpha granule of the platelet.

In embodiments, the isolated platelet further comprises an at least second compound in which the at least second compound comprises an at least second agent and an at least second polypeptide and the at least second polypeptide comprises an at least second glycosaminoglycan (GAG)-binding peptide which is capable of binding a GAG in an alpha granule of a platelet.

In embodiments, the at least second GAG-binding peptide preferentially binds to chondroitin sulfate (CS) and/or to heparan sulfate (HS).

In embodiments, the at least second GAG-binding peptide is between about 8 amino acids and about 14 amino acids in length.

In embodiments, the at least second GAG-binding peptide comprises an amino acid sequence that is at least about 70%, at least about 80%, or at least about 90% identical to one of SEQ ID NO: 1 to SEQ ID NO: 13.

In embodiments, the at least second GAG-binding peptide comprises a proline, arginine and/or isoleucine at position 1, position 4, position 7, and/or position 9 with respect to any one of SEQ ID NO: 1 to SEQ ID NO: 13.

In embodiments, the at least second GAG-binding peptide comprises or consist 10 amino acids or 11 amino acids.

In embodiments, the at least second GAG-binding peptide comprises an amino acid sequence that is at least about 90% identical to SEQ ID NO: 1 or to SEQ ID NO:2.

In embodiments, the at least second GAG-binding peptide comprises an amino acid sequence of one of SEQ ID NO: 1 to SEQ ID NO: 13.

In embodiments, the at least second GAG-binding peptide comprises an amino acid sequence of SEQ ID NO: 1 or SEQ ID NO:2.

In embodiments, the at least second GAG-binding peptide consists of the amino acid sequence of one of SEQ ID NO: 1 to SEQ ID NO: 13.

In embodiments, the GAG-binding peptide comprises an amino acid sequence that is at least about 90% identical to SEQ ID NO: 1 and the at least second GAG-binding peptide comprises an amino acid sequence that is at least about 90% identical to SEQ ID NO: 2. In embodiments, the GAG-binding peptide comprises an amino acid sequence of SEQ ID NO: 1 and the at least second GAG-binding peptide comprises an amino acid sequence of SEQ ID NO: 2.

In embodiments, the at least second agent comprises an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet.

In embodiments, the first agent is different from the at least second agent. Alternately, the first agent is the same as the at least second agent.

In embodiments, the at least second agent is indirectly linked to the at least second polypeptide via at least one linker. In embodiments, the at least second agent is directly linked to the at least second polypeptide.

In embodiments, the platelet comprises 1 to 1000 copies of the at least second compound, e.g., in an alpha granule of the platelet.

In embodiments, the compound is loaded into a first alpha granule in the platelet and the at least second compound is loaded into an at least second alpha granule in the platelet.

In embodiments, the compound and the at least second compound are both loaded into the same alpha granule.

Yet another aspect of the present disclosure is a pharmaceutical composition comprising the isolated platelet of comprising at least one copy of any herein disclosed compound and one or more pharmaceutically-acceptable excipients.

In an aspect, the present disclosure provides a pharmaceutical composition comprising the isolated platelet of comprising at least one copy of any herein disclosed first compound, at least one copy of any herein disclosed second compound, and one or more pharmaceutically-acceptable excipients In another aspect, the present disclosure provides a pharmaceutical composition comprising a first isolated platelet, an at least second isolated platelet, and one or more pharmaceutically-acceptable excipients. The first isolated platelet comprising a first compound comprising a first agent and a first polypeptide in which the first polypeptide comprises a first glycosaminoglycan (GAG)-binding peptide which is capable of binding a first GAG in an alpha granule of the platelet. The at least second isolated platelet comprising an at least second compound comprising an at least second agent and an at least second polypeptide in which the at least second polypeptide comprises an at least second GAG-binding peptide which is capable of binding an at least second GAG in an alpha granule of the platelet.

In embodiments, the first and/or the at least second GAG-binding peptide preferentially binds to chondroitin sulfate (CS) and/or to heparan sulfate (HS). In embodiments, the first and/or the at least second GAG-binding peptide preferentially binds to chondroitin sulfate A (CSA).

In embodiments, the first and/or the at least second GAG-binding peptide bind to heparan sulfate (HS), serglycin, perlecan, dermatan sulfate, keratan sulfate, and/or GPIIb/IIIa. In embodiments, the first and/or the at least second GAG-binding peptide does not preferentially bind to heparan sulfate (HS), serglycin, perlecan, dermatan sulfate, keratan sulfate, and/or GPIIb/IIIa. In embodiments, the first and/or the at least second GAG-binding peptide does not bind, does not detectably bind, does not substantially bind, or binds with low affinity to HS, serglycin, perlecan, dermatan sulfate, keratan sulfate, and/or GPIIb/IIIa.

In embodiments, the first and/or the at least second GAG-binding peptide remains bound to a CS-containing column when exposed to about 1N NaCl. In embodiments, the first and/or the at least second GAG-binding peptide remains bound to a CS-containing column when exposed to about 2N NaCl. In embodiments, the first and/or the at least second GAG-binding peptide is unbound to a CS-containing column when exposed to about 3N NaCl.

In embodiments, the first and/or the at least second GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of between about 0.001N and about 0.01N. In embodiments, the first and/or the at least second GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 0.1N. In embodiments, the first and/or the at least second GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 1N.

In embodiments, the first and/or the at least second GAG-binding peptide is between about 8 amino acids and about 14 amino acids in length.

In embodiments, the first and/or the at least second GAG-binding peptide comprises at least one charged amino acid.

In embodiments, the first and/or the at least second GAG-binding peptide comprises at least one proline, arginine, and/or isoleucine.

In embodiments, the first and/or the at least second GAG-binding peptide comprises an amino acid sequence that is at least about 70% identical to one of SEQ ID NO: 1 to SEQ ID NO: 13, is at least about 80% identical to one of SEQ ID NO: 1 to SEQ ID NO: 13, or is at least about 90% identical to one of SEQ ID NO: 1 to SEQ ID NO: 13.

In embodiments, the first and/or the at least second GAG-binding peptide comprises a charged amino acid at position 1, position 4, position 7, and/or position 9 with respect to any one of SEQ ID NO: 1 to SEQ ID NO: 13.

In embodiments, the first and/or the at least second GAG-binding peptide comprises a proline, arginine and/or isoleucine at position 1, position 4, position 7, and/or position 9 with respect to any one of SEQ ID NO: 1 to SEQ ID NO: 13.

In embodiments, the first and/or the at least second GAG-binding peptide comprises at least 10 amino acids. In embodiments, the first and/or the at least second GAG-binding peptide comprises 11 amino acids. In embodiments, the first and/or the at least second GAG-binding peptide consists of 11 amino acids.

In embodiments, the first and/or the at least second GAG-binding peptide comprises an amino acid sequence that is at least about 90% identical to SEQ ID NO: 1 or to SEQ ID NO:2.

In embodiments, the first and/or the at least second GAG-binding peptide comprises an amino acid sequence of one of SEQ ID NO: 1 to SEQ ID NO: 13.

In embodiments, the first and/or the at least second GAG-binding peptide comprises an amino acid sequence of SEQ ID NO: 1 or SEQ ID NO:2.

In embodiments, the first and/or the at least second GAG-binding peptide consists of the amino acid sequence of one of SEQ ID NO: 1 to SEQ ID NO: 13.

In embodiments, the first and/or the at least second polypeptide consists, respectively, of the first and/or the at least second GAG-binding peptide.

In embodiments, the N-terminal of the first and/or the at least second polypeptide is, respectively, directly or indirectly linked to the first and/or the at least second agent. In embodiments, the C-terminal of the first and/or the at least second polypeptide is, respectively, directly or indirectly linked to the first and/or the at least second agent. In embodiments, the first and/or the at least second agent is, respectively, indirectly linked to the first and/or the at least second polypeptide via at least one linker. In embodiments, the at least one linker comprises one or more atoms. In embodiments, the at least one linker comprises a polymer of repeating units. In embodiments, the at least one linker comprises a chain of amino acids. In embodiments, the first and/or the at least second agent is, respectively, directly linked to the first and/or the at least second polypeptide.

In embodiments, the first agent is directly or indirectly linked to the first polypeptide using a maleimide reaction, succinimidyl ester reaction, an enzymatic reaction, or another conjugation systems that does not affect protein structure or activity.

In embodiments, the at least second agent is directly or indirectly linked to the at least second polypeptide using a maleimide reaction, succinimidyl ester reaction, an enzymatic reaction, or another conjugation systems that does not affect protein structure or activity.

In embodiments, the first and/or the at least second agent are independently selected from the group consisting of an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), and a factor that inhibits cellular proliferation, angiogenesis, inflammation, immunity, or another physiological process mediated by or associated with a platelet. In embodiments, the first and/or the at least second agent comprises an antibody. In embodiments, the first and/or the at least second agent comprises a fluorescent moiety.

In embodiments, the first and/or the at least second agent is harmful to mammalian cells and/or is toxic to a subject.

In embodiments, the first and/or the at least second agent is susceptible to degradation when administered directly into the bloodstream of a subject.

In embodiments, the first and/or the at least second compound further comprises a fluorescent moiety.

In embodiments, the first and the at least second polypeptides are different. In embodiments, the first and the at least second polypeptide are the same.

In embodiments, the first and the at least second agents are different. In embodiments, the first and the at least second agents are the same.

In embodiments, the first and/or the at least second isolated platelet is independently selected from a synthetic, an allogeneic, an autologous, and a modified heterologous platelet. In embodiments, the first and/or the at least second isolated platelet is an autologous platelet. In embodiments, the first and/or the at least second isolated platelet is an allogeneic platelet. In embodiments, the first and/or the at least second isolated platelet is obtained from platelet rich plasma.

In embodiments, the first isolated platelet comprises 1 to 1000 copies of the first compound. In embodiments, the at least second isolated platelet comprises 1 to 1000 copies of the at least second compound. In embodiments, the 1 to 1000 copies of the first and/or the at least second compound are loaded into an alpha granule of the platelet.

An aspect of the present disclosure is a use of any herein-disclosed pharmaceutical composition for treating a disease or a disorder. In embodiments, the disease or disorder is a cancer.

Another aspect of the present disclosure is a use of any herein-disclosed pharmaceutical composition in the manufacture of a medicament for treating a disease or disorder. In embodiments, the disease or disorder is a cancer.

Yet another aspect of the present disclosure is a method for treating a disease or disorder in a subject in need thereof. The method comprises a step of administering to the subject a therapeutically-effective amount of any herein-disclosed pharmaceutical composition.

In an aspect, the present disclosure provides a method for treating a disease or disorder in a subject in need thereof. The method comprises a step of administering to the subject a therapeutically-effective amount of a pharmaceutical composition in which pharmaceutical composition comprises any herein-disclosed compound and one or more pharmaceutically-acceptable excipients.

In embodiments, the method further comprises a step of administering to the subject a second pharmaceutical composition comprising one or more of heparanase, thrombin and its fragment peptides, a protease-activated receptor 1 (PAR1) agonist or antagonist peptide, a protease-activated receptor 4 (PAR4) agonist or antagonist peptide, plasmin and its fragments, a metalloproteinase, a peroxidase, and/or a phosphohydrolase.

In embodiments, the second pharmaceutical composition promotes release of a compound from a platelet.

In embodiments, the second pharmaceutical composition is administered after the pharmaceutical composition is administered. In embodiments, the pharmaceutical composition is administered at least twice before the second pharmaceutical composition is administered.

In embodiments, the disease or disorder is a cancer. In embodiments, the disease of disorder is an injury. In embodiments, the disease of disorder is inflammation. In embodiments, the disease of disorder is a side effect of an implant, graft, stent, or prosthesis. In embodiments, the disease of disorder is caused by a defective gene.

In another aspect, the present disclosure provides a method for manufacturing a loaded platelet. The method comprises steps of: obtaining a platelet; contacting the platelet in vitro or ex vivo with any herein-disclosed compound; and allowing contact between the platelet and the compound to progress until the compound is internalized by an alpha granule of the platelet, thereby producing a loaded platelet.

In embodiments, the method further comprises a step of contacting the platelet in vitro or ex vivo with an at least second compound in which the at least second compound comprises an at least second agent and an at least second polypeptide and the at least second polypeptide comprises an at least second glycosaminoglycan (GAG)-binding peptide which is capable of binding a GAG in an alpha granule of a platelet; and a step of allowing contact between the platelet and the at least second compound to progress until the at least second compound is internalized by an alpha granule of the platelet.

In embodiments, the step of contacting the platelet in vitro or ex vivo with the compound and the step of contacting the platelet in vitro or ex vivo with the at least second compound are sequential. In embodiments, the step of contacting the platelet in vitro or ex vivo with the compound and the step of contacting the platelet in vitro or ex vivo with the at least second compound are contemporaneous.

An aspect of the present disclosure is a kit for treating a disease or disorder. The kit comprising any herein-disclosed isolated platelet and instructions for use.

Another aspect of the present disclosure is a kit for treating a disease or disorder. The kit comprising any herein-disclosed pharmaceutical composition and instructions for use.

In embodiments, the kit further comprises an at least second pharmaceutical composition comprising one or more of heparanase, thrombin and its fragment peptides, a protease-activated receptor 1 (PAR1) agonist or antagonist peptide, a protease-activated receptor 4 (PAR4) agonist or antagonist peptide, plasmin and its fragments, a metalloproteinase, a peroxidase, and/or a phosphohydrolase.

Yet another aspect of the present disclosure is a kit for manufacturing a loaded platelet. The kit comprising any herein-disclosed compound and instructions for use.

Any aspect or embodiment disclosed herein can be combined with any other aspect or embodiment as disclosed herein.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1A:
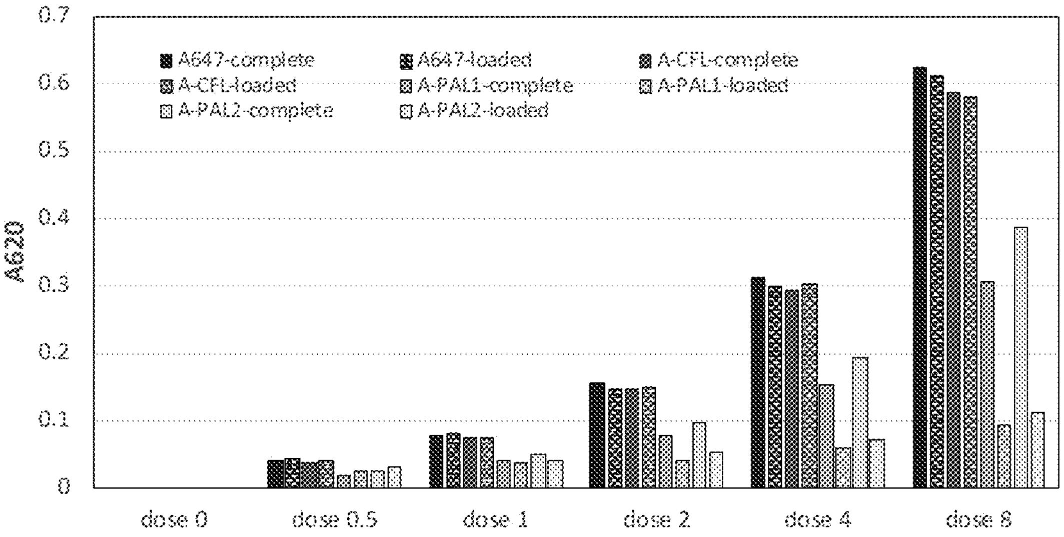
FIG. 1A and FIG. 1B are graphs showing the ability of illustrative glycosaminoglycan (GAG)-binding peptides to sequester attached cargos into platelets.

The present invention is based, in part, on the creation of platelets loaded with agents that provide directed therapeutics to sites of injury, pathological inflammation, and/or angiogenesis. Such agents sequestered within platelets, e.g., platelet alpha granules, are generally protected from degradation, which may occur upon systemic administration. This benefit, coupled with platelets' natural ability to home to sites of injury, inflammation, and/or angiogenesis helps to ensure that a therapeutically-effective amount of the agent is delivered to a target site. Additionally, platelets useful in the present invention can be loaded with a plurality of different agents; the different agents can be released from alpha granules in a spatially- and temporally-controlled fashion. Accordingly, the present invention provides directed and controlled therapeutics to sites of injury (e.g., for treating chronic wounds), pathological inflammation (e.g., for treating injury to joints or lungs), and/or angiogenesis (e.g., for treating cancer).

Prior to the present invention, it was counterintuitive that agents could be internalized into platelets by being anchored to specific glycosaminoglycans (GAG) in alpha granules and that a specific GAG-binding peptide can be used to facilitate the process of internalization. Indeed, previously, there was no known method for loading agents into platelet alpha granules. Moreover, it was unknown that subpopulations of alpha granules could be loaded with different agents, thereby allowing spatially- and/or temporally-controlled release of the different agents. Such controlled release allows sequential delivery of different agents, which could result in a synergistic therapeutic effect that may not be observed when the different agents are administered simultaneously.

The present invention provides numerous benefits, including, but not limited to:

(1) Targeted delivery of an agent to the site of a primary tumor or metastatic growth, which avoids the need for systemic administration of high doses of the agent; thus, lower doses of the agent are needed to achieve therapeutically effective concentrations of the agent at the target site;

(2) Agents sequestered in platelet alpha granules are unable to bind off-target receptors; thus, side effects (e.g., toxicity) associated with systemic administration of the agent alone is avoided; and (3) Agents sequestered in platelet alpha granules are protected from degradation by natural processes (e.g., tissue proteases); thus, the agent's half-life is extended relative to the agent when systemically administered alone.

Platelets, Platelet Granules, and Glycosaminoglycans

The present invention provides compounds, pharmaceutical compositions, and methods for treating diseases, disorders, or injuries in which platelets are naturally first responders and in which platelets ameliorate, at least, the initial symptoms of the disease, disorder, or injury. Illustrative diseases, disorders, or injuries include, but are not limited to, cancer, rheumatoid arthritis, diabetic retinopathy, obesity, atherosclerosis, ischemic heart and limb disease, ulcerative colitis, stroke, burns, and other wounds. Under physiological conditions, circulating platelets maintain the health and stability of tissues.

New information about the role of platelets in wound and tumor microenvironment has emerged; see, e.g., Klement et al., "Platelets actively sequester angiogenesis regulators", Blood. 2009; 113: 2835-42 and Klement et al., "The Role of Platelets in Angiogenesis. In: Michelson A, editor. Platelets. Third ed. Philadelphia, PA: Mosby Elsevier; 2013. p. 487-503. However, an understanding of the complexity of platelet/tissue interaction and the role of platelets in modulating tissue growth and angiogenesis has been slow to emerge. It is known that platelets contain different types of granules, including alpha granules, dense granules, and lysosomes, which perform different functions. The alpha granules, which normally contain growth factors, are the most prevalent type of granule. See, Blair and Flaumenhaft, "Platelet alpha-granules: basic biology and clinical correlates". Blood Reviews. 2009, 23 (4): 177-89 and Harrison and Cramer, "Platelet alpha-granules". Blood Reviews. 1993, 7 (1): 52-62. Normally, an alpha granule's cargo predominantly comprises inhibitors of angiogenesis; see, e.g., Peterson et al., "Normal ranges of angiogenesis regulatory proteins in human plate-lets." American journal of hematology. 2010; 85: 487-93. However, when a subject has cancer, platelet cargoes change and the alpha granules become predominantly loaded with stimulators; see, Peterson et al., American journal of hematology. 2010; 85: 487-93 and Peterson et al., "VEGF, PF4 and PDGF are elevated in platelets of colorectal cancer patients." Angiogenesis. 2012; 15: 265-73.

The present invention is based, in part, on the discovery that cargo can be loaded in alpha granules and that this loading is not receptor-mediated. Instead, cargo loading into platelets, and specifically into their alpha granules, relies on the binding to glycosaminoglycans (GAG) in the alpha granules of the platelets. When platelets are contacted with a non-specific GAG inhibitor (i.e., Surfen), reduced amounts of cargos are loaded into platelets.

The present invention is further based, in part, on the discovery that a platelet's cargo is organized by function, with stimulators and inhibitors of angiogenesis taken up into distinct subsets of platelet alpha granules; this distinction is based on the cargo's binding affinities to chondroitin sulfate or heparan sulfate. Moreover, the P selectin-defined subset of alpha granules attracts GAG-binding compounds with weaker affinities (i.e., a higher Kd) for GAG and the von Willebrand factor (VWF)-defined subset of alpha granules houses proteins with strong affinity (i.e., higher Kd) interactions with chondroitin sulfate.

Additionally, the present invention is based, in part, on the surprising discovery that an alpha granules' cargo is not released en mass upon aggregation and coagulation. Instead, angiogenesis growth stimulators or inhibitors are released in a spatially- and temporally-controlled manner, in response to specific stimuli, such as the local level of thrombin. For this, the early reacting subset of alpha granules, which are labeled with P-selectin, release their contents immediately upon vascular injury (e.g., low thrombin conditions) and when PAR1 (the high-affinity thrombin receptor) was engaged; in contrast, the late reacting subset of alpha granules, which are labeled with vWF factor, release their contents when engaged by PAR4 (i.e., the low affinity thrombin receptor).

Accordingly, the present invention takes advantage of platelets' natural ability to target a breach in a blood vessel's endothelial layer. In the context of cancers, this allows a platelet's cargo to be delivered to a tumor site. Importantly, according to the present disclosure, a platelet's alpha granules are beforehand loaded with an agent and this agent is delivered, with specificity, to the provisional matrix formed at the tumor site. Thus, the present invention provides platelet-associated agent that are released from the provisional matrix by tissue proteases in a meticulous—temporally and spatially controlled—enzymatic action.

There are two main GAGs in platelets: heparan sulfate and chondroitin sulfate.

Heparan sulfate (HS) is a linear copolymer of uronic acid 1→4 linked to glucosamine but with a highly variable structure. The d-glucuronic acid predominates in HS, although substantial amounts of 1-iduronic acid can be present. In comparison to heparin, HS is much less substituted in sulfo groups.

Heparin is highly heterogeneous linear, polydisperse polysaccharide consisting of repeating units of 1→4-linked pyranosyluronic acid and 2-amino-2-deoxyglucopyranose (glucosamine) residues. The uronic acid residues typically consist of 90%1-idopyranosyluronic acid (1-iduronic acid) and 10% d-glucopyranosyluronic acid (d-glucuronic acid). The amino group of the glucosamine residue may be substituted with an acetyl or sulfo group or unsubstituted. The 3 and 6 positions of the glucosamine residues can either be substituted with an O-sulfo group or unsubstituted. The uronic acid, which can either be 1-iduronic or d-glucuronic acid, may also contain a 2-O-sulfo group Most heparin-binding proteins bind both heparin and heparan sulfate. Both are polydisperse polysaccharides with a heterogeneous saccharide sequences that bind a large number of proteins to a wide range of possible binding sites. Whereas heparin is primarily intracellular, HS proteoglycans (HSPGs) are localized to many cell surfaces and contribute to functions of the extracellular matrix (ECM), e.g., by stabilizing growth factors and protein ligands.

Chondroitin sulfate (CS) is a linear polymer of random sequences of repeated disaccharide units of: 2-acetylamino-2-deoxy-4-0-sulfate-3-0-~-D-glucopyranurosyl-D-galactose; 2-acetylamino-2-deoxy-6-0-sulfate-3-0-~-D-glucopyranurosyl-D-galactose; 2-acetylamino-2-deoxy-4,6-0-~-disulfate-3-0-D-glucopyranurosyl-D-galactose; and 2-acetylamino-2-deoxy-6-0-sulfate-3-0-~-2'-0-sulfate-D-glucopyranurosyl-D-galactose. Each Monosulfated disaccharide unit has a molecular weight of 500-600 g/mol and its total weight is 5-50 kDa. The volume of a molecule of chondroitin sulfate is much larger in solution than in dehydrated solid because it has large number of negative charges; in solution, the negative charges on the variable branches repel each other and force the molecule into an extended conformation. As such, there are numerous ligand-binding sites on a CS molecule.

Novel, non-natural, GAG-binding peptides are useful in the compounds and methods of the present disclosure, as they are essential for the loading of cargo into the alpha granules of platelets. The GAG-binding peptides of the present disclosure are chemically or enzymatically linked (directly or indirectly) to an agent or genetically expressed to produce a fusion protein containing the agent and the -binding peptide. The GAG-binding peptide and the coupled agent retain their function in the new compound or fusion product. Thus, the new compound or fusion product is capable of being selectively loaded into alpha granules of platelets.

Glycosaminoglycan (GAG)-Binding Peptide

The glycosaminoglycan (GAG)-binding peptide of the present disclosure are characterized by the presence of positively charged basic amino acids that form ion pairs with spatially defined negatively charged sulfo or carboxyl groups on a GAG chain. For example, Heparan sulfate (HS) has an average of two negative charges per disaccharide provided by sulfo and carboxyl groups; thus, the most common type of interaction between HS and proteins is ionic, even though some other non-electrostatic interactions such as hydrogen bonding and hydrophobic interactions may also contribute to the stability of the complexes. It was believed that the highly anionic nature of GAGs leads to nonspecific binding. However, in the alpha granules of platelets, a GAG-binding peptide's binding to HS or chondroitin sulfate (CS) in the specific alpha granule subsets occurs at high specificity. This interaction is facilitated by matching the GAG binding affinity and the GAG-binding peptide. The GAG-peptide interaction depends, in part, on the defined patterns and orientations of the sulfo and carboxyl groups along the polysaccharide sequence in the polymer, and a correct pattern of basic amino acids in the GAG-binding peptide to ensure the appropriate affinity and specificity of the complex.

Electrostatic interactions play a major role in the GAG-peptide interaction, and the position of basic amino acids such as arginine and lysine within the GAG-binding peptide's binding sequence is relevant. A number of studies have been undertaken to determine whether there is a consensus sequence of basic amino acids arranged in a specific way in the GAG-binding sites. For example, a comparison of heparin-binding sites from four proteins: apolipoprotein B, apolipoprotein E, vitronectin, and platelet factor 4 showed that these regions are characterized by two consensus sequences of amino acids: XBBXBX and XBBBXXBX, where B is a basic residue and X is a hydropathic residue. Molecular modeling studies showed that the sequence XBBXBX modeled in a β-strand conformation orients the basic amino acids on one face of the β-strand and the hydropathic residues pointing back into the protein core. Similarly, when the sequence XBBBXXBX is folded into an α-helix, the basic amino acids are displayed on one side of the helix. While some heparin-binding proteins include this consensus sequence, there are others that do not. As such, a structural motif in which the basic residues are close in space, but not necessarily close in the primary amino acid sequence, may also bind heparin.

Heparin-binding sites frequently contain clusters of one, two, or three basic amino acids (XBnX, where n=1, 2, or 3). Spacing of such clusters with one or two non-basic residues (BXmB, where m=1 or 2) is observed in natural proteins; this is consistent with the observation that heparin-binding proteins usually bind HS in biological systems. Because the charge density of HS is lower, optimal protein binding may involve spaced clusters of basic amino acids. Arginine and lysine are the most frequent residues in heparin- and HS-binding proteins. Although both amino acids have a positive charge at physiological pH, arginine binds heparin ~2.5× more tightly. Arginine forms more stable hydrogen bonds as well as stronger electrostatic interactions with sulfo groups. Non-basic residues might also play an important role in heparin-protein interactions. Among them, serine and glycine have been found to be the most frequent non-basic residues in heparin-binding peptides. Both have small side chains, providing minimal steric constrains and good flexibility for peptide interaction with GAG.

The present invention is based, in part, on a novel, non-natural, glycosaminoglycan (GAG)-binding peptides. The GAG-binding peptides of the present disclosure are capable of binding a GAG in an alpha granule of a platelet.

In embodiments, a GAG-binding peptide binds a GAG through electrostatic interactions.

In embodiments, the GAG-binding peptide binds to chondroitin sulfate (CS) and/or heparan sulfate (HS). In embodiments, the GAG-binding peptide preferentially binds to CS. In embodiments, the GAG-binding peptide preferentially binds to chondroitin sulfate A (CSA).

In embodiments, the GAG-binding peptide binds to heparan sulfate (HS), serglycin, perlecan, dermatan sulfate, keratan sulfate, and/or GPIIb/IIIa. In embodiments, the GAG-binding peptide does not preferentially bind to heparan sulfate (HS), serglycin, perlecan, dermatan sulfate, keratan sulfate, and/or GPIIb/IIIa. In embodiments, the GAG-binding peptide does not bind, does not detectably bind, does not substantially bind, or binds with low affinity to HS, serglycin, perlecan, dermatan sulfate, keratan sulfate, and/or GPIIb/IIIa.

In embodiments, the GAG-binding peptide remains bound to a CS-containing column when exposed to about 1N NaCl. In embodiments, the GAG-binding peptide remains bound to a CS-containing column when exposed to about 2N NaCl. In embodiments, the GAG-binding peptide is unbound to a CS-containing column when exposed to about 3N NaCl.

In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of between about 0.001N and about 0.01N. In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 0.1N. In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 1N.

In embodiments, the GAG-binding peptide is between about 8 amino acids and about 14 amino acids in length.

In embodiments, the GAG-binding peptide comprises at least one charged amino acid.

In embodiments, the GAG-binding peptide comprises at least one proline, arginine, and/or isoleucine.

Illustrative GAG-binding peptides comprise one of the following amino acid sequences: ERRIWFPYRRF (SEQ ID NO: 1); RFRWPYRIREF (SEQ ID NO: 2); ARRIWFPYRRF (SEQ ID NO: 3); EARIWFPYRRF (SEQ ID NO: 4); ERAIWFPYRRF (SEQ ID NO: 5); ERRAWFPYRRF (SEQ ID NO: 6); ERRIAFPYRRF (SEQ ID NO: 7); ERRIWAPYRRF (SEQ ID NO: 8); ERRIWFAYRRF (SEQ ID NO: 9); ERRIWFPARRF (SEQ ID NO: 10); ERRIWFPYARF (SEQ ID NO: 11); ERRIWFPYRAF (SEQ ID NO: 12); and ERRIWFPYRRA (SEQ ID NO: 13).

In embodiments, the GAG-binding peptide comprises an amino acid sequence that is at least about 70% identical to one of SEQ ID NO: 1 to SEQ ID NO: 13, is at least about 80% identical to one of SEQ ID NO: 1 to SEQ ID NO: 13, or is at least about 90% identical to one of SEQ ID NO: 1 to SEQ ID NO: 13.

Without wishing to be bound to theory, it appears that the basic residues (e.g., arginines) are important in defining the GAG-binding peptide's properties and the hydropathic residues provide stabilization.

In embodiments, the GAG-binding peptide comprises a charged amino acid at position 1, position 4, position 7, or position 9 with respect to any one of SEQ ID NO: 1 to SEQ ID NO: 13.

In embodiments, the GAG-binding peptide comprises a proline, arginine, and/or isoleucine at position 1, position 4, position 7, and/or position 9 with respect to any one of SEQ ID NO: 1 to SEQ ID NO: 13. As examples, the GAG-binding peptide comprises a proline, arginine and/or isoleucine at position 1, position 4, position 7, and position 9; the GAG-binding peptide comprises a proline, arginine and/or isoleucine at position 1; the GAG-binding peptide comprises a proline, arginine and/or isoleucine at position 1 and position 4; the GAG-binding peptide comprises a proline, arginine and/or isoleucine at position 1, position 4, and position 7, and/or position 9; the GAG-binding peptide comprises a proline, arginine and/or isoleucine at position 1, position 4, position 7, and position 9; the GAG-binding peptide comprises a proline, arginine and/or isoleucine at position 1 and position 7; the GAG-binding peptide comprises a proline, arginine and/or isoleucine at position 1 and position 4 and position 9; the GAG-binding peptide comprises a proline, arginine and/or isoleucine at position 1 and position 9; and any combination therebetween. The GAG-binding peptide may comprise a proline at position 1, position 4, position 7, and position 9; the GAG-binding peptide may comprise an arginine at position 1, position 4, position 7, and position 9; the GAG-binding peptide may comprise an isoleucine at position 1, position 4, position 7, and position 9; the GAG-binding peptide may comprise a proline at position 1, and argenines at position 4, position 7, and position 9; the GAG-binding peptide may comprise a proline at position 1, argenines at position 4 and position 7, and an isoleucine at position 9; the GAG-binding peptide may comprise a proline at position 1, an argenine at position 4, and an isoleucine at position 9; or the GAG-binding peptide may comprise an argenine at position 4 and an proline at position 9. Any combinations of proline, arginine, and/or isoleucine at position 1, position 4, position 7, and/or position 9 is encompassed by the present disclosure.

In embodiments, the GAG-binding peptide comprises at least 10 amino acids. In embodiments, the GAG-binding peptide comprises 11 amino acids. In embodiments, the GAG-binding peptide consists of 11 amino acids.

In embodiments, the GAG-binding peptide comprises an amino acid sequence that is at least about 90% identical to SEQ ID NO: 1 or to SEQ ID NO:2.

In embodiments, the GAG-binding peptide comprises an amino acid sequence of one of SEQ ID NO: 1 to SEQ ID NO: 13.

In embodiments, the GAG-binding peptide comprises an amino acid sequence of SEQ ID NO: 1 or SEQ ID NO:2.

In embodiments, the GAG-binding peptide consists of the amino acid sequence of one of SEQ ID NO: 1 to SEQ ID NO: 13.

The invention provides methods for optimizing GAG-binding peptides by producing a variant GAG-binding peptides, e.g., by including deletions, mutations, insertions, or post-translational modifications, in a herein disclosed GAG-binding peptide's amino acid sequence.

A variant may differ from a GAG-binding peptide of SEQ ID NO: 1 to SEQ ID NO: 13 at one amino acid position, as long as the variant GAG-binding peptide retains its function.

A variant may differ from a GAG-binding peptide of SEQ ID NO: 1 to SEQ ID NO: 13 at two amino acid positions, as long as the variant GAG-binding peptide retains its function.

A variant may differ from a GAG-binding peptide of SEQ ID NO: 1 to SEQ ID NO: 13 at three amino acid positions, as long as the variant GAG-binding peptide retains its function.

A variant may differ from a GAG-binding peptide of SEQ ID NO: 1 to SEQ ID NO: 13 at four amino acid positions, as long as the variant GAG-binding peptide retains its function.

A variant may differ from a GAG-binding peptide of SEQ ID NO: 1 to SEQ ID NO: 13 at five amino acid positions, as long as the variant GAG-binding peptide retains its function.

A variant may differ from a GAG-binding peptide of SEQ ID NO: 1 to SEQ ID NO: 13 at more than five amino acid positions, as long as the variant GAG-binding peptide retains its function.

In embodiments, the amino acid differences may include conservative and/or non-conservative substitutions. "Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. As used herein, "non-conservative substitutions" are defined as exchanges of an amino acid by another amino acid listed in a different group of the six standard amino acid groups (1) to (6) shown above. A GAG-binding peptide may be modified by including chemical alterations such as acetylation, carboxylation, phosphorylation, or glycosylation.

Accordingly, the present disclosure provides methods for characterizing and optimizing (e.g., increasing affinity) GAG-binding peptides directed against various glycosaminoglycans. The optimized GAG-binding peptides provided by the present disclosure may be directed to glycosaminoglycans present in alpha granules of platelets. Illustrative glycosaminoglycans which are present in alpha granules of platelets include chondroitin sulfate, heparan sulfate, serglycin, perlecan, dermatan sulfate, keratan sulfate, and GPIIb/IIIa. Any of the optimized GAG-binding peptides may be included in a compostions of the present disclosure; any of the compositions may be loaded into a platelet, e.g., for inclusion in a pharmaceutical composition and/or for treating a disease or disorder.

Compounds and Agents

As disclosed herein, platelets can selectively and actively (i.e., against a concentration gradient) sequester angiogenesis, growth, and inflammation regulating proteins. The present disclosure is based on the discovery that proteins are taken up by platelets and segregated into subsets of alpha granules based on their affinity for glycosaminoglycans (GAGs): predominantly heparan sulfate (HS) and chondroitin sulfate (CS). The long, linear, negatively charged chains of these GAGs provide not only structural support to the alpha granules but also explain the functional subsets of alpha granules. The two main GAGs present in platelets (i.e., HS and CS) differ mainly in the number of disaccharides found in the individual chains. Heparan sulfate is small (15-30 disaccharides/side chain), whereas chondroitin sulfate has many binding sites and has up to 250 disaccharides/side chain. Both are distinct from the large, stiff, GAGs such as hyaluronate (up to 50,000 disaccharides/GAG side chain), which functions to maintain the structure and integrity of cartilage and bone. The diversity of the GAGs in platelets is crucial for their function, with the shorter side chains of the heparan sulfate and the weaker binding allowing for early release of P-selectin granules; whereas, the tighter, longer chain binding allows for late release of vWF granules. These features are exploited in the present invention for sequential release of compounds.

The present invention comprises novel, non-naturally occurring platelet anchoring glycosaminoglycan (GAG)-binding peptide which bind CS, at least, and with a very high affinity and bind HS with, at least, moderate affinity. When linked to an agent in a compound of the present disclosure, the GAG-binding peptide facilitates the "loading" of the agents into the alpha granules of platelets. Because platelets continuously circulate and adhere to sites of abnormal endothelium, the compounds of the present disclosure are widely applicable to a variety of pathological conditions.

An aspect of the present disclosure is a compound comprising a first agent and a first polypeptide. The first polypeptide comprises a glycosaminoglycan (GAG)-binding peptide which is capable of binding a GAG in an alpha granule of a platelet.

In embodiments, the GAG-binding peptide binds to chondroitin sulfate (CS) and/or heparan sulfate (HS). In embodiments, the GAG-binding peptide preferentially binds to CS. In embodiments, the GAG-binding peptide preferentially binds to chondroitin sulfate A (CSA).

In embodiments, the GAG-binding peptide binds to heparan sulfate (HS), serglycin, perlecan, dermatan sulfate, keratan sulfate, and/or GPIIb/IIIa. In embodiments, the GAG-binding peptide does not preferentially bind to heparan sulfate (HS), serglycin, perlecan, dermatan sulfate, keratan sulfate, and/or GPIIb/IIIa. In embodiments, the GAG-binding peptide does not bind, does not detectably bind, does not substantially bind, or binds with low affinity to HS, serglycin, perlecan, dermatan sulfate, keratan sulfate, and/or GPIIb/IIIa.

In embodiments, the GAG-binding peptide remains bound to a CS-containing column when exposed to about 1N NaCl. In embodiments, the GAG-binding peptide remains bound to a CS-containing column when exposed to about 2N NaCl. In embodiments, the GAG-binding peptide is unbound to a CS-containing column when exposed to about 3N NaCl.

In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of between about 0.001N and about 0.01N. In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 0.1N. In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 1N.

In embodiments, the GAG-binding peptide is between about 8 amino acids and about 14 amino acids in length.

In embodiments, the GAG-binding peptide comprises at least one charged amino acid.

In embodiments, the GAG-binding peptide comprises at least one proline, arginine, and/or isoleucine.

In embodiments, the GAG-binding peptide comprises an amino acid sequence that is at least about 70% identical to one of SEQ ID NO: 1 to SEQ ID NO: 13, is at least about 80% identical to one of SEQ ID NO: 1 to SEQ ID NO: 13, or is at least about 90% identical to one of SEQ ID NO: 1 to SEQ ID NO: 13.

In embodiments, the GAG-binding peptide comprises a charged amino acid at position 1, position 4, position 7, or position 9 with respect to any one of SEQ ID NO: 1 to SEQ ID NO: 13.

In embodiments, the GAG-binding peptide comprises a proline, arginine, and/or isoleucine at position 1, position 4, position 7, and/or position 9 with respect to any one of SEQ ID NO: 1 to SEQ ID NO: 13. As examples, the GAG-binding peptide comprises a proline, arginine and/or isoleucine at position 1, position 4, position 7, and position 9; the GAG-binding peptide comprises a proline, arginine and/or isoleucine at position 1; the GAG-binding peptide comprises a proline, arginine and/or isoleucine at position 1 and position 4; the GAG-binding peptide comprises a proline, arginine and/or isoleucine at position 1, position 4, and position 7, and/or position 9; the GAG-binding peptide comprises a proline, arginine and/or isoleucine at position 1, position 4, position 7, and position 9; the GAG-binding peptide comprises a proline, arginine and/or isoleucine at position 1 and position 7; the GAG-binding peptide comprises a proline, arginine and/or isoleucine at position 1 and position 4 and position 9; the GAG-binding peptide comprises a proline, arginine and/or isoleucine at position 1 and position 9; and any combination therebetween. The GAG-binding peptide may comprise a proline at position 1, position 4, position 7, and position 9; the GAG-binding peptide may comprise an arginine at position 1, position 4, position 7, and position 9; the GAG-binding peptide may comprise an isoleucine at position 1, position 4, position 7, and position 9; the GAG-binding peptide may comprise a proline at position 1, and argenines at position 4, position 7, and position 9; the GAG-binding peptide may comprise a proline at position 1, argenines at position 4 and position 7, and an isoleucine at position 9; the GAG-binding peptide may comprise a proline at position 1, an argenine at position 4, and an isoleucine at position 9; or the GAG-binding peptide may comprise an argenine at position 4 and an proline at position 9. Any combinations of proline, arginine, and/or isoleucine at position 1, position 4, position 7, and/or position 9 is encompassed by the present disclosure.

In embodiments, the GAG-binding peptide comprises at least 10 amino acids. In embodiments, the GAG-binding peptide comprises 11 amino acids. In embodiments, the GAG-binding peptide consists of 11 amino acids.

In embodiments, the GAG-binding peptide comprises an amino acid sequence that is at least about 90% identical to SEQ ID NO: 1 or to SEQ ID NO:2.

In embodiments, the GAG-binding peptide comprises an amino acid sequence of one of SEQ ID NO: 1 to SEQ ID NO: 13.

In embodiments, the GAG-binding peptide comprises an amino acid sequence of SEQ ID NO: 1 or SEQ ID NO:2.

In embodiments, the GAG-binding peptide consists of the amino acid sequence of one of SEQ ID NO: 1 to SEQ ID NO: 13.

In embodiments, the first polypeptide consists of the GAG-binding peptide. Alternately, the first polypeptide includes amino acids other than the GAG-binding peptide; in some embodiments, the additional amino acids in the polypeptide do not increase affinity of the GAG-binding peptide to a GAG.

In embodiments, the N-terminal of the first polypeptide is directly or indirectly linked to the first agent. In embodiments, the C-terminal of the first polypeptide is directly or indirectly linked to the first agent. In embodiments, the first agent is indirectly linked to the first polypeptide via at least one linker. In embodiments, the at least one linker comprises one or more atoms. In embodiments, the at least one linker comprises a polymer of repeating units. In embodiments, the at least one linker comprises a chain of amino acids.

In any herein disclosed aspect or embodiment, an agent and GAG-binding peptide may be directly linked or they may be linked via a moiety referred to as a linker. A linker refers to a chemical moiety comprising a covalent bond or a chain of atoms that covalently attaches an agent to a GAG-binding peptide. Linkers include a divalent radical such as an alkylene, an arylene, a heteroarylene, moieties such as: —(CR2)nO(CR2)n-, a polymer of repeating units of alkyloxy (e.g., polyethylenoxy, polyethylene glycol (PEG), polymethyleneoxy) and alkylamino (e.g., polyethyleneamino, Jeffamine™); and diacid ester and amides including succinate, succinamide, diglycolate, malonate, and caproamide. In embodiments, the linker comprises a chain of amino acids. In embodiments, the amino acid chain linker is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the amino acid chain linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In embodiments, the amino acid chain linker is between about 15 amino acids and about 3 amino acids, e.g., between about 10 and 5 amino acids.

In embodiments, the first agent is directly linked to the first polypeptide.

In embodiments, the first agent is directly or indirectly linked to the first polypeptide using a maleimide reaction, succinimidyl ester reaction, an enzymatic reaction, or another conjugation systems that does not affect protein structure or activity.

In embodiments, the first agent comprises an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet. In embodiments, the first agent comprises an antibody. In embodiments, the first agent comprises a fluorescent moiety.

Illustrative antibodies (or fragments thereof) useful in the present invention include 3F8, 8H9, Abagovomab, Abciximab, Abituzumab, Abrezekimab, Abrilumab, Actoxumab, Adalimumab, Adecatumumab, Aducanumab, Afasevikumab, Afelimomab, Alacizumab pegol, Alemtuzumab, Alirocumab, Altumomab pentetate, Amatuximab, Anatumomab mafenatox, Andecaliximab, Anetumab ravtansine, Anifrolumab, Anrukinzumab (IMA-638), Apolizumab, Aprutumab ixadotin, Arcitumomab, Ascrinvacumab, Aselizumab, Atezolizumab, Atidortoxumab, Atinumab, Atorolimumab, Avelumab, Azintuxizumab vedotin, Bapineuzumab, Basiliximab, Bavituximab, BCD-100, Bectumomab, Begelomab, Belantamab mafodotin, Belimumab, Bemarituzumab, Benralizumab, Berlimatoxumab, Bermekimab, Bersanlimab, Bertilimumab, Besilesomab, Bevacizumab, Bezlotoxumab, Biciromab, Bimagrumab, Bimekizumab, Birtamimab, Bivatuzumab mertansine, Bleselumab, Blinatumomab, Blontuvetmab, Blosozumab, BMS 936559, Bococizumab, Brazikumab, Brentuximab vedotin, Briakinumab, Brodalumab, Brolucizumab, Brontictuzumab, Burosumab, Cabiralizumab, Camidanlumab tesirine, Camrelizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cemiplimab, Cergutuzumab amunaleukin, Certolizumab pegol, Cetrelimab, Cetuximab, Cibisatamab, Cirmtuzumab, Citatuzumab bogatox, Cixutumumab, Clazakizumab, Clenoliximab, Clivatuzumab tetraxetan, Codrituzumab, Cofetuzumab pelidotin, Coltuximab ravtansine, Conatumumab, Concizumab, Cosfroviximab, CR6261, Crenezumab, Crizanlizumab, Crotedumab, Cusatuzumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dezamizumab, Dinutuximab, Diridavumab, Domagrozumab, Dorlimomab aritox, Dostarlimab, Drozitumab, DS-8201, Duligotuzumab, Dupilumab, Durvalumab, Dusigitumab, Duvortuxizumab, Ecromeximab, Eculizumab, Edobacomab, Edrecolomab, Efalizumab, Efungumab, Eldelumab, Elezanumab, Elgemtumab, Elotuzumab, Elsilimomab, Emactuzumab, Emapalumab, Emibetuzumab, Emicizumab, Enapotamab vedotin, Enavatuzumab, Enfortumab vedotin, Enlimomab pegol, Enoblituzumab, Enokizumab, Enoticumab, Ensituximab, Epitumomab cituxetan, Epratuzumab, Eptinezumab, Erenumab, Erlizumab, Ertumaxomab, Etaracizumab, Etigilimab, Etrolizumab, Evinacumab, Evolocumab, Exbivirumab, Fanolesomab, Faralimomab, Faricimab, Farletuzumab, Fasinumab, FBTA05, Felvizumab, Fezakinumab, Fibatuzumab, Ficlatuzumab, Figitumumab, Firivumab, Flanvotumab, Fletikumab, Flotetuzumab, Fontolizumab, Foralumab, Foravirumab, Fremanezumab, Fresolimumab, Frovocimab, Frunevetmab, Fulranumab, Futuximab, Galcanezumab, Galiximab, Gancotamab, Ganitumab, Gantenerumab, Gatipotuzumab, Gavilimomab, Gedivumab, Gemtuzumab ozogamicin, Gevokizumab, Gilvetmab, Gimsilumab, Girentuximab, Glembatumumab vedotin, Golimumab, Gomiliximab, Gosuranemab, Guselkumab, Ianalumab, Ibalizumab, IBI308, Ibritumomab tiuxetan and 90Y-Ibritumomab tiuxetan, Icrucumab, Idarucizumab, Ifabotuzumab, Igovomab, Iladatuzumab vedotin, IMAB362, Imalumab, Imaprelimab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Iomab-B, Ipilimumab, Iratumumab, Isatuximab, Iscalimab, Istiratumab, Itolizumab, Ixekizumab, Keliximab, Labetuzumab, Lacnotuzumab, Ladiratuzumab vedotin, Lampalizumab, Lanadelumab, Landogrozumab, Laprituximab emtansine, Larcaviximab, Lebrikizumab, Lemalesomab, Lendalizumab, Lenvervimab, Lenzilumab, Lerdelimumab, Leronlimab, Lesofavumab, Letolizumab, Lexatumumab, Libivirumab, Lifastuzumab vedotin, Ligelizumab, Lilotomab satetraxetan, Lintuzumab, Lirilumab, Lodelcizumab, Lokivetmab, Loncastuximab tesirine, Lorvotuzumab mertansine, Losatuxizumab vedotin, Lucatumumab, Lulizumab pegol, Lumiliximab, Lumretuzumab, Lupartumab amadotin, Lutikizumab, Mapatumumab, Margetuximab, Marstacimab, Maslimomab, Matuzumab, Mavrilimumab, Mepolizumab, Metelimumab, Milatuzumab, Minretumomab, Mirikizumab, Mirvetuximab soravtansine, Mitumomab, MK-3475, Modotuximab, Mogamulizumab, Monalizumab, Morolimumab, Mosunetuzumab, Motavizumab, Moxetumomab pasudotox, MPDL328OA, Muromonab-CD3, Nacolomab tafenatox, Namilumab, Naptumomab estafenatox, Naratuximab emtansine, Narnatumab, Natalizumab, Navicixizumab, Navivumab, Naxitamab, Nebacumab, Necitumumab, Nemolizumab, NEOD001, Nerelimomab, Nesvacumab, Netakimab, Nimotuzumab, Nirsevimab, Nivolumab, Nofetumomab merpentan, Obiltoxaximab, Obinutuzumab, Ocaratuzumab, Ocrelizumab, Odulimomab, Ofatumumab, Olaratumab, Oleclumab, Olendalizumab, Olokizumab, Omalizumab, Omburtamab, OMS721, Onartuzumab, Ontuxizumab, Onvatilimab, Opicinumab, Oportuzumab monatox, Oregovomab, Orticumab, Otelixizumab, Otilimab, Otlertuzumab, Oxelumab, Ozanezumab, Ozoralizumab, Pagibaximab, palivizumab, Pamrevlumab, Panitumumab, Pankomab, Panobacumab, Parsatuzumab, Pascolizumab, Pasotuxizumab, Pateclizumab, Patritumab, PDR001, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Porgaviximab, Prasinezumab, Prezalizumab, Priliximab, Pritoxaximab, Pritumumab, PRO 140, Quilizumab, Racotumomab, Radretumab, Rafivirumab, Ralpancizumab, Ramucirumab, Ranevetmab, Ranibizumab, Ravagalimab, Ravulizumab, Raxibacumab, Refanezumab, Regavirumab, Relatlimab, Remtolumab, Reslizumab, Rilotumumab, Rinucumab, Risankizumab, Rituximab, Rivabazumab pegol, Rmab, Robatumumab, Roledumab, Romilkimab, Romosozumab, Rontalizumab, Rosmantuzumab, Rovalpituzumab tesirine, Rovelizumab, Rozanolixizumab, Ruplizumab, SA237, Sacituzumab govitecan, Samalizumab, Samrotamab vedotin, Sarilumab, Satralizumab, Satumomab Pendetide, Secukinumab, Selicrelumab, Seribantumab, Setoxaximab, Setrusumab, Sevirumab, SGN-CD19A, SHP647, Sibrotuzumab, Sifalimumab, Siltuximab, Simtuzumab, Siplizumab, Sirtratumab vedotin, Sirukumab, Sofituzumab vedotin, Solanezumab, Solitomab, Sonepcizumab, Sontuzumab, Spartalizumab, Stamulumab, Sulesomab, Suptavumab, Sutimlimab, Suvizumab, Suvratoxumab, Tabalumab, Tacatuzumab tetraxetan, Tadocizumab, Talacotuzumab, Talizumab, Tamtuvetmab, Tanezumab, Taplitumomab paptox, Tarextumab, Tavolimab, Tefibazumab, Telimomab aritox, Telisotuzumab vedotin, Tenatumomab, Teneliximab, Teplizumab, Tepoditamab, Teprotumumab, Tesidolumab, Tetulomab, Tezepelumab, TGN1412, Tibulizumab, Tigatuzumab, Tildrakizumab, Timigutuzumab, Timolumab, Tiragotumab, Tislelizumab, Tisotumab vedotin, TNX-650, Tocilizumab, Tomuzotuximab, Toralizumab, Tosatoxumab, Tositumomab and 1311-tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vanalimab, Vandortuzumab vedotin, Vantictumab, Vanucizumab, Vapaliximab, Varisacumab, Varlilumab, Vatelizumab, Vedolizumab, Veltuzumab, Vepalimomab, Vesencumab, Visilizumab, Vobarilizumab, Volociximab, Vonlerolizumab, Vopratelimab, Vorsetuzumab mafodotin, Votumumab, Vunakizumab, Xentuzumab, XMAB-5574, Zalutumumab, Zanolimumab, Zatuximab, Zenocutuzumab, Ziralimumab, Zolbetuximab (IMAB362, Claudiximab), and Zolimomab aritox.

Illustrative antibodies (or fragments thereof) that have met or have pending regulatory approval and are useful in the present invention include Muromonab-CD3 (ORTHOCLONE OKT3), Efalizumab (RAPTIVA), Tositumomab-I131 (BEXXAR), Nebacumab (CENTOXIN), Edrecolomab (PANOREX), Catumaxomab (REMOVAB), Daclizumab (ZINBRYTA; ZENAPAX), Abciximab (REOPRO), Rituximab (MABTHERA, RITUXAN), Basiliximab (SIMULECT), palivizumab (SYNAGIS), Infliximab (REMICADE), Trastuzumab (HERCEPTIN), Adalimumab (HUMIRA), Ibritumomab tiuxetan (ZEVALIN), Omalizumab (XOLAIR), Cetuximab (ERBITUX), Bevacizumab (AVASTIN), Natalizumab (TYSABRI), Panitumumab (VECTIBIX), Ranibizumab (LUCENTIS), Eculizumab (SOLIRIS), Certolizumab pegol (CIMZIA), Ustekinumab (STELARA), Canakinumab (ILARIS), Golimumab (SIMPONI), Ofatumumab (ARZERRA), Tocilizumab (ROACTEMRA, ACTEMRA), Denosumab (PROLIA), Belimumab (BENLYSTA), Ipilimumab (YERVOY), Brentuximab vedotin (ADCETRIS), Pertuzumab (PERJETA), Ado-trastuzumab emtansine (KADCYLA), Raxibacumab), Obinutuzumab (GAZYVA, GAZYVARO), Siltuximab (SYLVANT), Ramucirumab (CYRAMZA), Vedolizumab (ENTYVIO), Nivolumab (OPDIVO), Pembrolizumab (KEYTRUDA), Blinatumomab (BLINCYTO), Alemtuzumab (LEMTRADA; MABCAMPATH, CAMPATH-1H), Evolocumab (REPATHA), Idarucizumab (PRAXBIND), Necitumumab (PORTRAZZA), Dinutuximab (UNITUXIN), Secukinumab (COSENTYX), Mepolizumab (NUCALA), Alirocumab (PRALUENT), Daratumumab (DARZALEX), Elotuzumab (EMPLICITI), Ixekizumab (TALTZ), Reslizumab (CINQAERO, CINQAIR), Olaratumab (LARTRUVO), Bezlotoxumab (ZINPLAVA), Atezolizumab (TECENTRIQ), Obiltoxaximab (ANTHIM), Brodalumab (SILIQ, LUMICEF), Dupilumab (DUPIXENT), Inotuzumab ozogamicin (BESPONSA), Guselkumab (TREMFYA), Sarilumab (KEVZARA), Avelumab (BAVENCIO), Emicizumab (HEMLIBRA), Ocrelizumab (OCREVUS), Benralizumab (FASENRA), Durvalumab (IMFINZI), Gemtuzumab ozogamicin (MYLOTARG), Erenumab, erenumab-aooe (AIMOVIG), Galcanezumab, galcanezumab-gnlm (EMGALITY), Burosumab, burosumab-twza (CRYSVITA), Lanadelumab, lanadelumab-flyo (TAKHZYRO), Mogamulizumab, mogamulizumab-kpkc (POTELIGEO), Tildrakizumab; tildrakizumab-asmn (ILUMYA), Fremanezumab, fremanezumab-vfrm (AJOVY), Ravulizumab, ravulizumab-cwvz (ULTOMIRIS), Cemiplimab, cemiplimab-rwlc (LIBTAYO), Ibalizumab, ibalizumab-uiyk (TROGARZO), Emapalumab, emapalumab-lzsg (GAMIFANT), Moxetumomab pasudotox, moxetumomab pasudotox-tdfk (LUMOXITI), Caplacizumab, caplacizumab-yhdp (CABLIVI), Risankizumab, risankizumab-rzaa (SKYRIZI), Polatuzumab vedotin, polatuzumab vedotin-piiq (POLIVY), Romosozumab, romosozumab-aqqg (EVENITY), Brolucizumab, brolucizumab-dbll (BEOVU), Crizanlizumab; crizanlizumab-tmca (ADAKVEO), Enfortumab vedotin, enfortumab vedotinejfv (PADCEV), [fam-]trastuzumab deruxtecan, fam-trastuzumab deruxtecan-nxki (ENHERTU), Teprotumumab, teprotumumab-trbw (TEPEZZA), Eptinezumab, eptinezumab-jjmr (VYEPTI), Isatuximab, isatuximab-irfc (SARCLISA), Sacituzumab govitecan; sacituzumab govitecan-hziy (TRODELVY), Inebilizumab; inebilizumab-cdon (UPLIZNA), Satralizumab (ENSPRYNG), Dostarlimab (TSR-042), Sutimlimab (BIVV009), Leronlimab, Narsoplimab, Tafasitamab, REGNEB3, Naxitamab, Oportuzumab monatox, Belantamab mafodotin, Margetuximab, Tanezumab, Teplizumab, Aducanumab, Evinacumab, Tralokinumab, and Omburtamab.

A fragment of an antibody will comprise, at least, the antigen-binding domain of an above-mentioned antibody. In embodiments, the antigen-binding domain is an antibody, an antibody fragment, an scFv, a Fv, a Fab, a (Fab')2, a single domain antibody (SDAB), a VH or VL domain, or a camelid VHH domain, e.g., a human scFv, human Fv, human Fab, human (Fab')2, human single domain antibody (SDAB), or human VH or VL domain or a humanized scFv, humanized Fv, humanized Fab, humanized (Fab')2, humanized single domain antibody (SDAB), or humanized VH or VL domain.

Illustrative chemotherapeutic agents useful in the present invention include 2,3,4,5,6-pentafluoro-N-(3-fluoro-4-methoxyphenyl)benzene sulfonamide, 3',4'-didehydro-4'-deoxy-8'-norvin-caleukoblastine, 5-FU (Fluorouracil), Abemaciclib, Abiraterone Acetate, Abitrexate (Methotrexate), Abraxane (Paclitaxel Albumin-stabilized Nanoparticle Formulation), ABVD, ABVE, ABVE-PC, AC, Acalabrutinib, AC-T, ADE, Adriamycin (Doxorubicin), Afatinib Dimaleate, Afinitor (Everolimus), Afinitor Difsperz (Everolimus), Akynzeo (Netupitant and palonosetron), Aldara (Imiquimod), Aldesleukin, Alecensa (Alectinib), Alectinib, Alimta (PEMETREXED), Aliqopa (Copanlisib Hydrochloride), Alkeran (Melphalan), Aloxi (palonosetron Hydrochloride), Altretamine, Alunbrig (Brigatinib), Ambochlorin (Chlorambucil), Amboclorin (Chlorambucil), Amifostine, Aminolevulinic Acid, Anastrozole, Anhydrovinblastine, Aprepitant, Aredia (Pamidronate), Arimidex (Anastrozole), Aromasin (Exemestane), Arranon (Nelarabine), Arsenic Trioxide, Asparaginase *Erwinia chrysanthemi*, Auristatin, Axicabtagene Ciloleucel, Axitinib, Azacitidine, BEACOPP, Becenum (Carmustine), Beleodaq (Belinostat), Belinostat, Bendamustine Hydrochloride, BEP, Bexarotene, Bicalutamide, BiCNU (Carmustine), Blenoxane (Bleomycin), BMS184476, Bortezomib, Bosulif (Bosutinib), Bosutinib, Brigatinib, BuMel, Busulfan, Busulfex (Busulfan)C, Cabazitaxel, Cabometyx (Cabozantinib), Cabozantinib-S-Malate, CAF, Calquence (Acalabrutinib), Camptosar (Irinotecan Hydrochloride), Capecitabine, CAPDX, Caprelsa (Vandetanib), Carac (Fluorouracil—Topical), Carboplatin, Carboplatin-Taxol, Carfilzomib, Carmubris (Carmustine), Carmustine, Casodex (Bicalutamide), Cachectin, CeeNU (Lomustine), CEM, Cemadotin, Ceritinib, Cerubidine (Daunorubicin), Cervarix (Recombinant HPV Bivalent Vaccine), CEV, Chlorambucil, Chlorambucil-Prednisone, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib), Copanlisib Hydrochloride, COPDAC, COPP, COPP-ABV, Cosmegen (Dactinomycin), Cotellic (Cobimetinib), Cryptophycin, Crizotinib, CVP, Cyclophosphamide, Cyfos (Ifosfamide), Cytarabine, Cytarabine Liposome, Cytosar-U (Cytarabine), Cytoxan (Cyclophosphamide), Cytoxan (Cytoxan), Dabrafenib, Dacarbazine, Dacogen (Decitabine), Dactinomycin, Dasatinib, Daunorubicin Hydrochloride, Daunorubicin Hydrochloride and Cytarabine Liposome, DaunoXome (Daunorubicin Lipid Complex), Decadron (Dexamethasone), Decitabine, Defibrotide Sodium, Defitelio (Defibrotide Sodium), Degarelix, Denileukin Diftitox, DepoCyt (Cytarabine Liposome), Dexamethasone, Dexamethasone Intensol (Dexamethasone), Dexpak Taperpak (Dexamethasone), Dexrazoxane Hydrochloride, Docefrez (Docetaxel), Docetaxel, Docetaxol, Dolastatin, Doxetaxel, Doxil (Doxorubicin Hydrochloride Liposome), Doxorubicin Hydrochloride, Doxorubicin Hydrochloride Liposome, Dox-SL (Doxorubicin Hydrochloride Liposome), Droxia (Hydroxyurea), DTIC (Decarbazine), DTIC-Dome (Dacarbazine), Efudex (Fluorouracil—Topical), Eligard (Leuprolide), Elitek (Rasburicase), Ellence (Ellence (epirubicin)), Eloxatin (Oxaliplatin), Elspar (Asparaginase), Eltrombopag Olamine, Emcyt (Estramustine), Emend (Aprepitant), Enasidenib Mesylate, Enzalutamide, Epirubicin Hydrochloride, EPOCH, Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide, Etoposide Phosphate, Eulexin (Flutamide), Evacet (Doxorubicin Hydrochloride Liposome), Everolimus, Evista (Raloxifene Hydrochloride), Evomela (Melphalan Hydrochloride), Exemestane, Fareston (Toremifene), Farydak (Panobinostat), Faslodex (Fulvestrant), FEC, Femara (Letrozole), Filgrastim, Firmagon (Degarelix), Finasteride, FloPred (Prednisolone), Fludara (Fludarabine), Fludarabine Phosphate, Fluoroplex (Fluorouracil), Fluorouracil, Flutamide, Folex (Methotrexate), Folex PFS (Methotrexate), FOLFIRI, FOLFIRINOX, FOLFOX, Folotyn (Pralatrexate), FUDR (FUDR (floxuridine)), FU-LV, Fulvestrant, Gardasil (Recombinant HPV Quadrivalent Vaccine), Gardasil 9 (Recombinant HPV Nonavalent Vaccine), Gefitinib, Gemcitabine Hydrochloride, GEMCITABINE-CISPLATIN, GEMCITABINE-OXALIPLATIN, Gemzar (Gemcitabine), Gilotrif (Afatinib Dimaleate), Gilotrif (Afatinib), Gleevec (Imatinib Mesylate), Gliadel (Carmustine), Glucarpidase, Goserelin Acetate, Halaven (Eribulin Mesylate), Hemangeol (Propranolol Hydrochloride), Hexalen (Altretamine), HPV Bivalent Vaccine, Recombinant, HPV Nonavalent Vaccine, Recombinant, HPV Quadrivalent Vaccine, Recombinant, Hycamtin (Topotecan Hydrochloride), Hycamtin (Topotecan), Hydrea (Hydroxyurea), Hydroxyurea, Hydroxyureataxanes, Hyper-CVAD, Ibrance (palbociclib), Ibrutinib, ICE, Iclusig (Ponatinib), Idamycin PFS (Idarubicin), Idarubicin Hydrochloride, Idelalisib, Idhifa (Enasidenib), Ifex (Ifosfamide), Ifosfamide, Ifosfamidum (Ifosfamide), Imatinib Mesylate, Imbruvica (Ibrutinib), Imiquimod, Imlygic (Talimogene Laherparepvec), Inlyta (Axitinib), Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), Jakafi (Ruxolitinib), JEB, Jevtana (Cabazitaxel), Keoxifene (Raloxifene Hydrochloride), Kepivance (palifermin), Kisqali (Ribociclib), Kyprolis (Carfilzomib), Lanreotide Acetate, Lanvima (Lenvatinib), Lapatinib Ditosylate, Lenalidomide, Lenvatinib Mesylate, Lenvima (Lenvatinib Mesylate), Letrozole, Leucovorin Calcium, Leukeran (Chlorambucil), Leukine (Sargramostim), Leuprolide Acetate, Leustatin (Cladribine), Levulan (Aminolevulinic Acid), Liarozole, Linfolizin (Chlorambucil), LipoDox (Doxorubicin Hydrochloride Liposome), Lomustine, Lonidamine, Lonsurf (Trifluridine and Tipiracil), Lupron (Leuprolide), Lynparza (Olaparib), Lysodren (Mitotane), Marqibo (Vincristine Sulfate Liposome), Marqibo Kit (Vincristine Lipid Complex), Matulane (Procarbazine), Mechlorethamine Hydrochloride, Megace (Megestrol), Megestrol Acetate, Mekinist (Trametinib), Melphalan, Melphalan Hydrochloride, Mercaptopurine, Mesnex (Mesna), Metastron (Strontium-89 Chloride), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), Mivobulin isethionate, MOPP, Mostarina (Prednimustine), Mozobil (Plerixafor), Mustargen (Mechlorethamine), Mutamycin (Mitomycin), Myleran (Busulfan), Mylosar (Azacitidine), Nanoparticle Paclitaxel (Paclitaxel Albumin-stabilized Nanoparticle Formulation), Navelbine (Vinorelbine), Nelarabine, Neosar (Cyclophosphamide), Neratinib Maleate, Nerlynx (Neratinib), Netupitant and palonosetron Hydrochloride, Neulasta (filgrastim), Neulasta (pegfilgrastim), Neupogen (filgrastim), Nexavar (Sorafenib), Nilandron (Nilutamide), Nilotinib, Nilutamide, Ninlaro (Ixazomib), Nipent (Pentostatin), Niraparib Tosylate Monohydrate, N,n-dimethyl-l-valyl-l-valyl-n-methyl-l-valyl-l-proly-l-lproline-t-butylamide, Nolvadex (Tamoxifen), Novantrone (Mitoxantrone), Nplate (Romiplostim), Odomzo (Sonidegib), OEPA, OFF, Olaparib, Omacetaxine Mepesuccinate, Onapristone, Oncaspar (Pegaspargase), Oncovin (Vincristine), Ondansetron Hydrochloride, Onivyde (Irinotecan Hydrochloride Liposome), Ontak (Denileukin Diftitox), Onxol (Paclitaxel), OPPA, Orapred (Prednisolone), Osimertinib, Oxaliplatin, Paclitaxel, Paclitaxel Albumin-stabilized Nanoparticle Formulation, PAD, palbociclib, palifermin, palonosetron Hydrochloride, palonosetron Hydrochloride and Netupitant, Pamidronate Disodium, Panobinostat, Panretin (Alitretinoin), Paraplat (Carboplatin), Pazopanib Hydrochloride, PCV, PEB, Pediapred (Prednisolone), Pegaspargase, Pegfilgrastim, Pemetrexed Disodium, Platinol (Cisplatin), PlatinolAQ (Cisplatin), Plerixafor, Pomalyst (Pomalidomide), Ponatinib Hydrochloride, Pralatrexate, Prednimustine, Prednisone, Procarbazine Hydrochloride, Proleukin (Aldesleukin), Promacta (Eltrombopag Olamine), Propranolol Hydrochloride, Purinethol (Mercaptopurine), Purixan (Mercaptopurine), Radium 223 Dichloride, Raloxifene Hydrochloride, Rasburicase, R-CHOP, R-CVP, Reclast (Zoledronic acid), Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Regorafenib, Relistor (Methylnaltrexone Bromide), R-EPOCH, Revlimid (Lenalidomide), Rheumatrex (Methotrexate), Rhizoxin, Ribociclib, R-ICE, Rolapitant Hydrochloride, Romidepsin, Romiplostim, Rpr109881, Rubex (Doxorubicin), Rubidomycin (Daunorubicin Hydrochloride), Rubraca (Rucaparib), Rucaparib Camsylate, Ruxolitinib Phosphate, Rydapt (Midostaurin), Sandostatin (Octreotide), Sandostatin LAR Depot (Octreotide), Sclerosol Intrapleural Aerosol (Talc), Sertenef, Soltamox (Tamoxifen), Somatuline Depot (Lanreotide Acetate), Sonidegib, Sorafenib Tosylate, Sprycel (Dasatinib), STANFORD V, Sterapred (Prednisone), Sterapred DS (Prednisone), Sterile Talc Powder (Talc), Steritalc (Talc), Sterecyst (Prednimustine), Stivarga (Regorafenib), Stramustine phosphate, Streptozocin, Sunitinib Malate, Supprelin LA (Histrelin), Sutent (Sunitinib Malate), Sutent (Sunitinib), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib), Targretin (Bexarotene), Tasigna (Decarbazine), Tasigna (Nilotinib), Tasonermin, Taxol (Paclitaxel), Taxotere (Docetaxel), Temodar (Temozolomide), Temozolomide, Temsirolimus, Tepadina (Thiotepa), Thalidomide, Thalomid (Thalidomide), TheraCys BCG (BCG), Thioguanine, Thioplex (Thiotepa), Thiotepa, TICE BCG (BCG), Tisagenlecleucel, Tolak (Fluorouracil—Topical), Toposar (Etoposide), Topotecan Hydrochloride, Toremifene, Torisel (Temsirolimus), Totect (Dexrazoxane Hydrochloride), TPF, Trabectedin, Trametinib, Treanda (Bendamustine hydrochloride), Trelstar (Triptorelin), Tretinoin, Trexall (Methotrexate), Trifluridine and Tipiracil Hydrochloride, Trisenox (Arsenic trioxide), Tykerb (lapatinib), Uridine Triacetate, VAC, Valrubicin, Valstar (Valrubicin Intravesical), Valstar (Valrubicin), VAMP, Vandetanib, Vantas (Histrelin), Varubi (Rolapitant), VeIP, Velban (Vinblastine), Velcade (Bortezomib), Velsar (Vinblastine Sulfate), Vemurafenib, Venclexta (Venetoclax), Vepesid (Etoposide), Verzenio (Abemaciclib), Vesanoid (Tretinoin), Viadur (Leuprolide Acetate), Vidaza (Azacitidine), Vinblastine, Vincasar PFS (Vincristine), Vincrex (Vincristine), Vincristine Sulfate, Vincristine Sulfate Liposome, Vindesine sulfate, Vinflunine, Vinorelbine Tartrate, VIP, Vismodegib, Vistogard (Uridine Triacetate), Voraxaze (Glucarpidase), Vorinostat, Votrient (Pazopanib), Vumon (Teniposide), Vyxeos (Daunorubicin Hydrochloride and Cytarabine Liposome), W, Wellcovorin (Leucovorin Calcium), Wellcovorin IV (Leucovorin), Xalkori (Crizotinib), XELIRI, Xeloda (Capecitabine), XELOX, Xofigo (Radium 223 Dichloride), Xtandi (Enzalutamide), Yescarta (Axicabtagene Ciloleucel), Yondelis (Trabectedin), Zaltrap (Ziv-Aflibercept), Zanosar (Streptozocin), Zarxio (Filgrastim), Zejula (Niraparib), Zelboraf (Vemurafenib), Zinecard (Dexrazoxane Hydrochloride), Ziv-Aflibercept, Zofran (Ondansetron Hydrochloride), Zoladex (Goserelin), Zoledronic Acid, Zolinza (Vorinostat), Zometa (Zoledronic acid), Zortress (Everolimus), Zydelig (Idelalisib), Zykadia (Ceritinib), Zytiga (Abiraterone Acetate), and Zytiga (Abiraterone). Other examples of chemotherapeutic agents can be found in Cancer Principles and Practice of Oncology by V. T. Devita and S. Hellman (editors), 6th edition (Feb. 15, 2001), Lippincott Williams & Wilkins Publishers, the contents of which is incorporated herein by reference in its entirety.

In embodiments, a chemotherapeutic agent, e.g., from the above list, may be included as an agent in a compound of the present disclosure. Alternately, or additionally, a chemotherapeutic agent, e.g., from the above list, may be used in conjunction with a compound of the present disclosure, i.e., in a combination therapy. As examples, a subject may be administered platelets loaded with one or both of a compound comprising a multikinase inhibitor (e.g., regorafenib) as agent and a compound comprising fumagillin as agent, and also administered a chemotherapeutic agent; this combination may be used for treating pancreatic cancer, lung cancer, or colon cancer. A subject may be administered platelets loaded with one or both of a compound comprising an EGFR inhibitor (e.g., Cetuximab) as agent and a compound comprising a multikinase inhibitor (e.g., regorafenib) as an active agent and also administered a chemotherapeutic agent; this may be used for treating lung cancer. Also, subject may be administered platelets loaded with one or both or all three of a compound comprising an EGFR inhibitor (e.g., Cetuximab) as agent, a compound comprising a multikinase inhibitor (e.g., regorafenib) as agent, and a compound comprising an ALK/ROS1/NTRK inhibitor (e.g., crizotinib) as agent and also administered a chemotherapeutic agent; this may be used for treating non-small cell lung cancer.

Illustrative immune checkpoint inhibitors useful in the present invention include full-length or fragments of ligands or receptors for A2AR, B7-H3, B7-H4, BTLA, CD122, CD137, CD27, CD28, CD28, CD40, CTLA-4, GITR, ICOS, ICOS, IDO, KIR, KIR., LAG3, NOX2, OX40, PD-1, SIGLEC7, SIGLEC9, TIM-3, and VISTA.

Illustrative growth factors useful in the present invention include vascular endothelial growth factor (VEGF), basic fibroblast growth factor (bFGF), and platelet-derived growth factor (PDGF), Epidermal Growth Factor (EGF), Hepatocyte Growth Factor (HGF), Insulin-Like Growth Factor (IGF), and an Angiopoietin.

Illustrative growth inhibitors useful in the present invention include angiostatin, endostatin, tumstatin, Thrombospondin-1 (TSP1), Platelet Factor 4 (PF4, CXCL4), and Tissue inhibitors of Metalloproteinases (TIMPs).

Illustrative proteases/proteinases useful in the present invention include Matrix Metalloproteinases (MMPs), thrombin, tissue plasminogen activator (tPA), urokinase, and streptokinase.

Illustrative coagulation factors useful in the present invention include Factor II (thrombin), Antithrombin III (ATIII), Kallikrein, tissue factor (TF), Factor V, Factor VII, Factor VIII, Factor IX, Factor X, Factor XI, and Factor XII, Factor XIII, Fibrinogen, Protein S, Protein C, thrombomodulin, plasminogen, and tissue factor pathway inhibitor (TFPI).

Illustrative lipids or phospholipids useful in the present invention include apolipoprotein E (ApoE), platelet phospholipids, and Sphingosine-1-phosphate (SIP).

Illustrative extracellular matrix proteins useful in the present invention include integrins, fibronectin, laminin, focal adhesion proteins (FAK), vinculin, talin, actin filaments, and collagen.

Illustrative hormones useful in the present invention include insulin, steroid (e.g., estrogen, progesterone, and testosterone, and variants thereof), erythropoietin, thrombopoietin, and thyroid hormone.

Illustrative enzymes useful in the present invention include Heparanase or a Matrix Metalloproteinase (MMP).

Illustrative chemokines/chemoattractants useful in the present invention include Connective Tissue Growth Factor (CTGF), Stromal Cell-derived Factor-1 (SDF-1) (CXCL12), interleukins (ILL 2, 6, 8), and CD40 Ligand (CD40L, CD154).

Illustrative neurotrophins useful in the present invention include nerve growth factor (NGF), brain-derived neurotrophic factor (BDNF), Neurotrophin-3 (NT-3), and Neurotrophin 4/5 (NT-4/5).

In embodiments, an agent is selected from the following non-exhaustive list which includes useful agents of various classifications: 3-4-(1-formylpiperazin-4-yl)-benzylidenyl-2-indolinone, Abatacept, ABT-869, Acalabrutinib, Afatinib, Aflibercept, Alectinib, Alefacept, AMG 108, Antilymphocyte immunoglobulin (horse), Antithymocyte immunoglobulin (rabbit), Apomab, Asfotase alfa, Asunercept, AVE9633, Axitinib, Belatacept, Bevacizumab zirconium Zr-89, BIIB015, Bivatuzumab, Bosutinib, Brigatinib, Cabozantinib, Canertinib, Capmatinib, Cediranib, Ceritinib, CR002, Crenolanib, Crizotinib, CT-011, Dacomitinib, Dasatinib, Depatuxizumab, Dovitinib, Edratide, Entrectinib, Erdafitinib, Erlotinib, Etanercept, Famitinib, Fedratinib, Firategrast, Flumatinib, Foretinib, Fostamatinib, Gefitinib, Geldanamycin, Genistein, Gilteritinib, Glesatinib, GMA-161, Gremubamab, GS-5745, Human cytomegalovirus immune globulin, Human immunoglobulin G, Human Varicella-Zoster Immune Globulin, Ibritumomab tiuxetan, Ibrutinib, Icotinib, IGN311, Imatinib, Indium In-111 satumomab pendetide, IPH 2101, Labetuzumab govitecan, Lapatinib, Larotrectinib, Lecanemab, Lenvatinib, Lestaurtinib, Lorukafusp alfa, Midostaurin, Mirvetuximab Soravtansine, Mitazalimab, Motesanib, Muromonab, Naptumomab Estafenatox, NAV 1800, Neratinib, Nilotinib, Nintedanib, Osimertinib, Pacritinib, Pazopanib, PD173955, Pexidartinib, Piceatannol, Ponatinib, Radicicol, Radotinib, Regorafenib, RI 624, Rovalpituzumab Tesirine, Rozrolimupab, Ruxolitinib, Saracatinib, Savolitinib, SB-1578, Selpercatinib, Selumetinib, Sorafenib, Sunitinib, Tafasitamab, Tandutinib, TB-402, Technetium Tc-99m arcitumomab, Tesevatinib, TNX-901, Tomaralimab, Tositumomab, Trastuzumab deruxtecan, Tucatinib, Vadastuximab Talirine, Valanafusp alfa, Vandetanib, Vatalanib, Vemurafenib, VS-4718, XmAb 2513, XTL-001, and Zolbetuximab.

In embodiments, the agent is an EGFR inhibitor (e.g., Cetuximab).

In embodiments, the agent is a VEGF inhibitor (e.g., Bevacizumab).

In embodiments, the agent is a PDL1 inhibitor (e.g., Pembrolizumab).

In embodiments, the agent is an FN1 inhibitor (e.g., Ocriplasmin).

In embodiments, the agent is a multikinase inhibitor (e.g., regorafenib).

In embodiments, the agent is a FGFR2 antagonist (e.g., thalidomide).

In embodiments, the agent is thrombin and its analogues.

In embodiments, the agent is a CSF3R agonist (e.g., Filgrastim).

In embodiments, the agent is a PSMB5 inhibitor (e.g., Bortezomib).

In embodiments, the agent is fumagillin.

In embodiments, the agent is an ALK/ROS1/NTRK inhibitor (e.g., crizotinib).

In embodiments, the first agent is harmful to mammalian cells and/or is toxic to a subject.

In embodiments, the first agent is susceptible to degradation when administered directly into the bloodstream of a subject.

In embodiments, the compound further comprises a fluorescent moiety.

In embodiments, the first agent is harmful to human cells and/or is toxic to a subject.

Any of the above-mentioned agents may be used in an at least second compound. An at least second compound comprises an at least second agent and an at least second polypeptide and the at least second polypeptide comprises an at least second glycosaminoglycan (GAG)-binding peptide which is capable of binding a GAG in an alpha granule of a platelet. Accordingly, any herein-disclosed agent may be a first agent or an at least second agent.

Isolated Platelets

Often an agent useful for treating disease or disorders, can be harmful to human cells and/or is toxic to a subject, and especially when administered systemically to the subject. Loading platelets with a compound comprising the harmful agent avoids the unintended and undesirable cellular, tissue, and/or organ damage in the subject. Additionally, certain agents are susceptible to degradation when administered directly into the bloodstream of a subject. Loading platelets with a compound comprising the degradable agent avoids a reduction is concentration of the agent which would occur when administered directly into the bloodstream of a subject; thus, the loaded platelets avoid a reduction in dose (e.g., below an effective dose) when administered to the subject. Together, the loaded platelets provide enrichment of the agent localized to the target site, at a desirable dose and with fewer adverse effects.

The technique of platelet-facilitated delivery of agents has numerous advantages over other targeted delivery systems. Unlike nanoparticle-facilitate delivery, no foreign substances are provided to the subject. Similarly, while liposomal preparations have short shelf life, poor stability, and short in vivo half-life due to phagocytosis by the reticuloendothelial system (RES), the platelet delivery system of the present disclosure extends the in vivo half-life and does not change the stability and preparation of the original compound. Also, most synthetic homing mechanisms, such as RGD peptides, which target abnormal vasculature, have not achieved the specificity of native platelets. Finally, the use of autologous platelets in the present invention eliminates the risk of another's infectious agents; this increases the safety of the procedure, and the speed of platelet loading (seconds to minutes) without needing to thaw and/or prepare donated and stored platelets. Together, the platelets-facilitated delivery of agents of the present disclosure can readily and easily be translated into the clinic.

Another aspect of the present disclosure is an isolated platelet comprising at least one copy of any herein disclosed compound.

In embodiments, the platelet is a synthetic, an allogeneic, an autologous, or a modified heterologous platelet. In embodiments, the platelet is an autologous platelet. In embodiments, the platelet is an allogeneic platelet. In embodiments, the platelet is obtained from platelet rich plasma.

In embodiments, the platelet comprises 1 to 1000 copies of the compound. In embodiments, the 1 to 1000 copies of the compound are loaded into an alpha granule of the platelet.

In embodiments, the compound comprises a first agent and a first polypeptide. The first polypeptide comprises a glycosaminoglycan (GAG)-binding peptide which is capable of binding a GAG in an alpha granule of a platelet.

In embodiments, the GAG-binding peptide binds to chondroitin sulfate (CS) and/or heparan sulfate (HS). In embodiments, the GAG-binding peptide preferentially binds to CS. In embodiments, the GAG-binding peptide preferentially binds to chondroitin sulfate A (CSA).

In embodiments, the GAG-binding peptide binds to heparan sulfate (HS), serglycin, perlecan, dermatan sulfate, keratan sulfate, and/or GPIIb/IIIa. In embodiments, the GAG-binding peptide does not preferentially bind to heparan sulfate (HS), serglycin, perlecan, dermatan sulfate, keratan sulfate, and/or GPIIb/IIIa. In embodiments, the GAG-binding peptide does not bind, does not detectably bind, does not substantially bind, or binds with low affinity to HS, serglycin, perlecan, dermatan sulfate, keratan sulfate, and/or GPIIb/IIIa.

In embodiments, the GAG-binding peptide remains bound to a CS-containing column when exposed to about 1N NaCl. In embodiments, the GAG-binding peptide remains bound to a CS-containing column when exposed to about 2N NaCl. In embodiments, the GAG-binding peptide is unbound to a CS-containing column when exposed to about 3N NaCl.

In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of between about 0.001N and about 0.01N. In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 0.1N. In embodiments, the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 1N.

In embodiments, the GAG-binding peptide is between about 8 amino acids and about 14 amino acids in length.

In embodiments, the GAG-binding peptide comprises at least one charged amino acid.

In embodiments, the GAG-binding peptide comprises at least one proline, arginine, and/or isoleucine.

In embodiments, the GAG-binding peptide comprises an amino acid sequence that is at least about 70% identical to one of SEQ ID NO: 1 to SEQ ID NO: 13, is at least about 80% identical to one of SEQ ID NO: 1 to SEQ ID NO: 13, or is at least about 90% identical to one of SEQ ID NO: 1 to SEQ ID NO: 13.

In embodiments, the GAG-binding peptide comprises a charged amino acid at position 1, position 4, position 7, or position 9 with respect to any one of SEQ ID NO: 1 to SEQ ID NO: 13.

In embodiments, the GAG-binding peptide comprises a proline, arginine, and/or isoleucine at position 1, position 4, position 7, and/or position 9 with respect to any one of SEQ ID NO: 1 to SEQ ID NO: 13. As examples, the GAG-binding peptide comprises a proline, arginine and/or isoleucine at position 1, position 4, position 7, and position 9; the GAG-binding peptide comprises a proline, arginine and/or isoleucine at position 1; the GAG-binding peptide comprises a proline, arginine and/or isoleucine at position 1 and position 4; the GAG-binding peptide comprises a proline, arginine and/or isoleucine at position 1, position 4, and position 7, and/or position 9; the GAG-binding peptide comprises a proline, arginine and/or isoleucine at position 1, position 4, position 7, and position 9; the GAG-binding peptide comprises a proline, arginine and/or isoleucine at position 1 and position 7; the GAG-binding peptide comprises a proline, arginine and/or isoleucine at position 1 and position 4 and position 9; the GAG-binding peptide comprises a proline, arginine and/or isoleucine at position 1 and position 9; and any combination therebetween. The GAG-binding peptide may comprise a proline at position 1, position 4, position 7, and position 9; the GAG-binding peptide may comprise an arginine at position 1, position 4, position 7, and position 9; the GAG-binding peptide may comprise an isoleucine at position 1, position 4, position 7, and position 9; the GAG-binding peptide may comprise a proline at position 1, and argenines at position 4, position 7, and position 9; the GAG-binding peptide may comprise a proline at position 1, argenines at position 4 and position 7, and an isoleucine at position 9; the GAG-binding peptide may comprise a proline at position 1, an argenine at position 4, and an isoleucine at position 9; or the GAG-binding peptide may comprise an argenine at position 4 and an proline at position 9. Any combinations of proline, arginine, and/or isoleucine at position 1, position 4, position 7, and/or position 9 is encompassed by the present disclosure.

In embodiments, the GAG-binding peptide comprises at least 10 amino acids. In embodiments, the GAG-binding peptide comprises 11 amino acids. In embodiments, the GAG-binding peptide consists of 11 amino acids.

In embodiments, the GAG-binding peptide comprises an amino acid sequence that is at least about 90% identical to SEQ ID NO: 1 or to SEQ ID NO:2.

In embodiments, the GAG-binding peptide comprises an amino acid sequence of one of SEQ ID NO: 1 to SEQ ID NO: 13.

In embodiments, the GAG-binding peptide comprises an amino acid sequence of SEQ ID NO: 1 or SEQ ID NO:2.

In embodiments, the GAG-binding peptide consists of the amino acid sequence of one of SEQ ID NO: 1 to SEQ ID NO: 13.

In embodiments, the first polypeptide consists of the GAG-binding peptide. Alternately, the first polypeptide includes amino acids other than the GAG-binding peptide; in some embodiments, the additional amino acids in the polypeptide do not increase affinity of the GAG-binding peptide to a GAG.

In embodiments, the N-terminal of the first polypeptide is directly or indirectly linked to the first agent. In embodiments, the C-terminal of the first polypeptide is directly or indirectly linked to the first agent. In embodiments, the first agent is indirectly linked to the first polypeptide via at least one linker. In embodiments, the at least one linker comprises one or more atoms. In embodiments, the at least one linker comprises a polymer of repeating units. In embodiments, the at least one linker comprises a chain of amino acids.

In embodiments, the first agent comprises an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet.

In embodiments, the isolated platelet further comprises an at least second compound in which the at least second compound comprises an at least second agent and an at least second polypeptide and the at least second polypeptide comprises an at least second glycosaminoglycan (GAG)-binding peptide which is capable of binding a GAG in an alpha granule of a platelet.

In embodiments, the at least second GAG-binding peptide preferentially binds to chondroitin sulfate (CS) and/or to heparan sulfate (HS).

In embodiments, the at least second GAG-binding peptide is between about 8 amino acids and about 14 amino acids in length.

In embodiments, the at least second GAG-binding peptide comprises an amino acid sequence that is at least about 70%, at least about 80%, or at least about 90% identical to one of SEQ ID NO: 1 to SEQ ID NO: 13.

In embodiments, the at least second GAG-binding peptide comprises a proline, arginine and/or isoleucine at position 1, position 4, position 7, and/or position 9 with respect to any one of SEQ ID NO: 1 to SEQ ID NO: 13.

In embodiments, the at least second GAG-binding peptide comprises or consist 10 amino acids or 11 amino acids.

In embodiments, the at least second GAG-binding peptide comprises an amino acid sequence that is at least about 90% identical to SEQ ID NO: 1 or to SEQ ID NO:2.

In embodiments, the at least second GAG-binding peptide comprises an amino acid sequence of one of SEQ ID NO: 1 to SEQ ID NO: 13.

In embodiments, the at least second GAG-binding peptide comprises an amino acid sequence of SEQ ID NO: 1 or SEQ ID NO:2.

In embodiments, the at least second GAG-binding peptide consists of the amino acid sequence of one of SEQ ID NO: 1 to SEQ ID NO: 13.

In embodiments, the GAG-binding peptide comprises an amino acid sequence that is at least about 90% identical to SEQ ID NO: 1 and the at least second GAG-binding peptide comprises an amino acid sequence that is at least about 90% identical to SEQ ID NO: 2. In embodiments, the GAG-binding peptide comprises an amino acid sequence of SEQ ID NO: 1 and the at least second GAG-binding peptide comprises an amino acid sequence of SEQ ID NO: 2.

In embodiments, the at least second agent comprises an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet.

In embodiments, the first agent is different from the at least second agent. Alternately, the first agent is the same as the at least second agent.

In embodiments, the at least second agent is indirectly linked to the at least second polypeptide via at least one linker. In embodiments, the at least second agent is directly linked to the at least second polypeptide.

In embodiments, the platelet comprises 1 to 1000 copies of the at least second compound.

In embodiments, the compound is loaded into a first alpha granule in the platelet and the at least second compound is loaded into an at least second alpha granule in the platelet.

In embodiments, the compound and the at least second compound are both loaded into the same alpha granule.

Pharmaceutical Compositions

Loaded platelets of the present disclosure can be formulated into pharmaceutical compositions which enhance stability and effectiveness of the platelets, at least, once administered to a subject. Moreover, such pharmaceutical compositions enhance stability of the platelets prior to administration to the subject.

Yet another aspect of the present disclosure is a pharmaceutical composition comprising the isolated platelet of comprising at least one copy of any herein disclosed compound and one or more pharmaceutically-acceptable excipients.

In an aspect, the present disclosure provides a pharmaceutical composition comprising the isolated platelet of comprising at least one copy of any herein disclosed first compound, at least one copy of any herein disclosed second compound, and one or more pharmaceutically-acceptable excipients.

In another aspect, the present disclosure provides a pharmaceutical composition comprising a first isolated platelet, an at least second isolated platelet, and one or more pharmaceutically-acceptable excipients. The first isolated platelet comprising a first compound comprising a first agent and a first polypeptide in which the first polypeptide comprises a first glycosaminoglycan (GAG)-binding peptide which is capable of binding a first GAG in an alpha granule of the platelet. The at least second isolated platelet comprising an at least second compound comprising an at least second agent and an at least second polypeptide in which the at least second polypeptide comprises an at least second GAG-binding peptide which is capable of binding an at least second GAG in an alpha granule of the platelet.

In embodiments, the first and/or the at least second GAG-binding peptide preferentially binds to chondroitin sulfate (CS) and/or to heparan sulfate (HS). In embodiments, the first and/or the at least second GAG-binding peptide preferentially binds to chondroitin sulfate A (CSA).

In embodiments, the first and/or the at least second GAG-binding peptide bind to heparan sulfate (HS), serglycin, perlecan, dermatan sulfate, keratan sulfate, and/or GPIIb/IIIa. In embodiments, the first and/or the at least second GAG-binding peptide does not preferentially bind to heparan sulfate (HS), serglycin, perlecan, dermatan sulfate, keratan sulfate, and/or GPIIb/IIIa. In embodiments, the first and/or the at least second GAG-binding peptide does not bind, does not detectably bind, does not substantially bind, or binds with low affinity to HS, serglycin, perlecan, dermatan sulfate, keratan sulfate, and/or GPIIb/IIIa.

In embodiments, the first and/or the at least second GAG-binding peptide remains bound to a CS-containing column when exposed to about 1N NaCl. In embodiments, the first and/or the at least second GAG-binding peptide remains bound to a CS-containing column when exposed to about 2N NaCl. In embodiments, the first and/or the at least second GAG-binding peptide is unbound to a CS-containing column when exposed to about 3N NaCl.

In embodiments, the first and/or the at least second GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of between about 0.001N and about 0.01N. In embodiments, the first and/or the at least second GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 0.1N. In embodiments, the first and/or the at least second GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of at least about 1N.

In embodiments, the first and/or the at least second GAG-binding peptide is between about 8 amino acids and about 14 amino acids in length.

In embodiments, the first and/or the at least second GAG-binding peptide comprises at least one charged amino acid.

In embodiments, the first and/or the at least second GAG-binding peptide comprises at least one proline, arginine, and/or isoleucine.

In embodiments, the first and/or the at least second GAG-binding peptide comprises an amino acid sequence that is at least about 70% identical to one of SEQ ID NO: 1 to SEQ ID NO: 13, is at least about 80% identical to one of SEQ ID NO: 1 to SEQ ID NO: 13, or is at least about 90% identical to one of SEQ ID NO: 1 to SEQ ID NO: 13.

In embodiments, the first and/or the at least second GAG-binding peptide comprises a charged amino acid at position 1, position 4, position 7, or position 9 with respect to any one of SEQ ID NO: 1 to SEQ ID NO: 13.

In embodiments, the first and/or the at least second GAG-binding peptide comprises a proline, arginine and/or isoleucine at position 1, position 4, position 7, and/or position 9 with respect to any one of SEQ ID NO: 1 to SEQ ID NO: 13.

As examples, the first and/or the at least second GAG-binding peptide comprises a proline, arginine and/or isoleucine at position 1, position 4, position 7, and position 9; the first and/or the at least second GAG-binding peptide comprises a proline, arginine and/or isoleucine at position 1; the first and/or the at least second GAG-binding peptide comprises a proline, arginine and/or isoleucine at position 1 and position 4; the first and/or the at least second GAG-binding peptide comprises a proline, arginine and/or isoleucine at position 1, position 4, and position 7, and/or position 9; the first and/or the at least second GAG-binding peptide comprises a proline, arginine and/or isoleucine at position 1, position 4, position 7, and position 9; the first and/or the at least second GAG-binding peptide comprises a proline, arginine and/or isoleucine at position 1 and position 7; the first and/or the at least second GAG-binding peptide comprises a proline, arginine and/or isoleucine at position 1 and position 4 and position 9; the first and/or the at least second GAG-binding peptide comprises a proline, arginine and/or isoleucine at position 1 and position 9; and any combination therebetween. The first and/or the at least second GAG-binding peptide may comprise a proline at position 1, position 4, position 7, and position 9; the first and/or the at least second GAG-binding peptide may comprise an arginine at position 1, position 4, position 7, and position 9; the first and/or the at least second GAG-binding peptide may comprise an isoleucine at position 1, position 4, position 7, and position 9; the first and/or the at least second GAG-binding peptide may comprise a proline at position 1, and argenines at position 4, position 7, and position 9; the first and/or the at least second GAG-binding peptide may comprise a proline at position 1, argenines at position 4 and position 7, and an isoleucine at position 9; the first and/or the at least second GAG-binding peptide may comprise a proline at position 1, an argenine at position 4, and an isoleucine at position 9; or the first and/or the at least second GAG-binding peptide may comprise an argenine at position 4 and an proline at position 9. Any combinations of proline, arginine, and/or isoleucine at position 1, position 4, position 7, and/or position 9 is encompassed by the present disclosure.

In embodiments, the first and/or the at least second GAG-binding peptide comprises at least 10 amino acids. In embodiments, the first and/or the at least second GAG-binding peptide comprises 11 amino acids. In embodiments, the first and/or the at least second GAG-binding peptide consists of 11 amino acids.

In embodiments, the first and/or the at least second GAG-binding peptide comprises an amino acid sequence that is at least about 90% identical to SEQ ID NO: 1 or to SEQ ID NO:2.

In embodiments, the first and/or the at least second GAG-binding peptide comprises an amino acid sequence of one of SEQ ID NO: 1 to SEQ ID NO: 13.

In embodiments, the first and/or the at least second GAG-binding peptide comprises an amino acid sequence of SEQ ID NO: 1 or SEQ ID NO:2.

In embodiments, the first and/or the at least second GAG-binding peptide consists of the amino acid sequence of one of SEQ ID NO: 1 to SEQ ID NO: 13.

In embodiments, the first and/or the at least second polypeptide consists, respectively, of the first and/or the at least second GAG-binding peptide.

In embodiments, the N-terminal of the first and/or the at least second polypeptide is, respectively, directly or indirectly linked to the first and/or the at least second agent. In embodiments, the C-terminal of the first and/or the at least second polypeptide is, respectively, directly or indirectly linked to the first and/or the at least second agent. In embodiments, the first and/or the at least second agent is, respectively, indirectly linked to the first and/or the at least second polypeptide via at least one linker. In embodiments, the at least one linker comprises one or more atoms. In embodiments, the at least one linker comprises a polymer of repeating units. In embodiments, the at least one linker comprises a chain of amino acids. In embodiments, the first and/or the at least second agent is, respectively, directly linked to the first and/or the at least second polypeptide.

In embodiments, the first agent is directly or indirectly linked to the first polypeptide using a maleimide reaction, succinimidyl ester reaction, an enzymatic reaction, or another conjugation systems that does not affect protein structure or activity.

In embodiments, the at least second agent is directly or indirectly linked to the at least second polypeptide using a maleimide reaction, succinimidyl ester reaction, an enzymatic reaction, or another conjugation systems that does not affect protein structure or activity.

In embodiments, the first and/or the at least second agent are independently selected from the group consisting of an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), and a factor that inhibits cellular proliferation, angiogenesis, inflammation, immunity, or another physiological process mediated by or associated with a platelet. In embodiments, the first and/or the at least second agent comprises an antibody. In embodiments, the first and/or the at least second agent comprises a fluorescent moiety.

In embodiments, the first and/or the at least second agent is harmful to mammalian cells and/or is toxic to a subject.

In embodiments, the first and/or the at least second agent is susceptible to degradation when administered directly into the bloodstream of a subject.

In embodiments, the first and/or the at least second compound further comprises a fluorescent moiety.

In embodiments, the first and the at least second polypeptides are different. In embodiments, the first and the at least second polypeptide are the same.

In embodiments, the first and the at least second agents are different. In embodiments, the first and the at least second agents are the same.

In embodiments, the first and/or the at least second isolated platelet is independently selected from a synthetic, an allogeneic, an autologous, and a modified heterologous platelet. In embodiments, the first and/or the at least second isolated platelet is an autologous platelet. In embodiments, the first and/or the at least second isolated platelet is an allogeneic platelet. In embodiments, the first and/or the at least second isolated platelet is obtained from platelet rich plasma.

In embodiments, the first isolated platelet comprises 1 to 1000 copies of the first compound. In embodiments, the at least second isolated platelet comprises 1 to 1000 copies of the at least second compound. In embodiments, the 1 to 1000 copies of the first and/or the at least second compound are loaded into an alpha granule of the platelet.

Pharmaceutical compositions comprise a pharmaceutically acceptable carrier or vehicle. Such pharmaceutical compositions can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In embodiments, the pharmaceutically acceptable excipients are sterile when administered to a subject. Water is a useful excipient when any agent disclosed herein is administered intravenously. Saline solutions and aqueous dextrose and glycerol solutions can also be employed as liquid excipients, specifically for injectable solutions. Suitable pharmaceutical excipients also include starch, glucose (i.e., dextrose), lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent disclosed herein, if desired, can also comprise minor amounts of wetting or emulsifying agents, or pH buffering agents. Examples of suitable pharmaceutical excipients are described in Remington's Pharmaceutical Sciences 1447-1676 (Alfonso R. Gennaro eds., 19th ed. 1995), incorporated herein by reference.

In embodiments, the pharmaceutical composition disclosed herein comprises a saline buffer (including, without limitation a NaCl solution, TBS, PBS, Ringer's solution, and the like).

In embodiments, the pharmaceutical compositions disclosed herein in the form suitable for sterile injection that is approximate isotonic to blood and that has a pH of between about 7.3 and 7.5 (i.e., the pH of blood).

In embodiments, the pharmaceutical composition disclosed herein is formulated in accordance with routine procedures as a pharmaceutical composition adapted for a mode of administration disclosed herein.

An aspect of the present disclosure is a use of any herein-disclosed pharmaceutical composition for treating a disease or a disorder. In embodiments, the disease or disorder is a cancer.

Another aspect of the present disclosure is a use of any herein-disclosed pharmaceutical composition in the manufacture of a medicament for treating a disease or disorder. In embodiments, the disease or disorder is a cancer.

Treatment Methods

As disclosed previously, platelets loaded with a compound comprising an agent avoids a reduction in concentration of the agent (e.g., below an effective dose) which occurs when the agent is administered to the subject without loading into platelets. Additionally, platelets loaded with a compound comprising a harmful (e.g., toxic) agent avoids the unintended and undesirable cellular, tissue, and/or organ damage in the subject. Finally, platelets naturally home to sites of injury, inflammation, and/or angiogenesis. Together, the loaded platelets help ensure that a therapeutically-effective amounts of one or more agent is delivered to a target site and with fewer adverse effects.

Diseases and disorders characterized by tissue inflammation or tissue damage and characterized by platelets being a first responders, can all be treated according to the disclosed methods. These diseases and disorders include, but are not limited to, neoplasia, hematologic malignancies, rheumatoid arthritis, ulcerative colitis, stroke, ischemic heart disease, atherosclerosis, burns, and graft epithelization.

An advantage provided by the present invention is the prolonged half-life (in a subject's bloodstream) of an agent when loaded into a platelet relative to the agent directly administered to the bloodstream. The present invention slows the natural elimination of the agent is reduced significantly. Normally, an agent is eliminated from the circulation by renal filtration, enzymatic degradation, uptake by the reticulo-endothelial system (RES), and accumulation in non-targeted organs and tissues. However, in the present invention, the agent is protected within the platelet for the life-span of the platelet (typically 4-7 days) or until delivered to the target site. In addition, the present invention limits exposure of the agent systemically by avoiding widespread distribution of the agent to non-target sites (e.g., tissues and organs). The benefits allow use of lower dosages of the agents (relative to administrations the agents that are not loaded into platelets). Such use of lower doses, at least, helps reduce unwanted side-effects and reduces economic costs.

Also, platelets useful in the present invention can be loaded with a plurality of different agents; the different agents can be released from alpha granules in a spatially- and temporally-controlled fashion. Accordingly, the present invention provides directed and controlled therapeutics to sites of injury (e.g., for treating chronic wounds), pathological inflammation (e.g., for treating injury to joints or lungs), and/or angiogenesis (e.g., for treating cancer).

An aspect of the present disclosure is a method for treating a disease or disorder in a subject in need thereof. The method comprises a step of administering to the subject a therapeutically-effective amount of a herein-disclosed pharmaceutical composition. The herein-disclosed pharmaceutical composition comprises a first isolated platelet, an at least second isolated platelet, and one or more pharmaceutically-acceptable excipients. The first isolated platelet comprising a first compound comprising a first agent and a first polypeptide in which the first polypeptide comprises a first glycosaminoglycan (GAG)-binding peptide which is capable of binding a first GAG in an alpha granule of the platelet. The at least second isolated platelet comprising an at least second compound comprising an at least second agent and an at least second polypeptide in which the at least second polypeptide comprises an at least second GAG-binding peptide which is capable of binding an at least second GAG in an alpha granule of the platelet.

In another aspect, the present disclosure provides a method for treating a disease or disorder in a subject in need thereof. The method comprises a step of administering to the subject a therapeutically-effective amount of a pharmaceutical composition in which pharmaceutical composition comprises a herein-disclosed compound and one or more pharmaceutically-acceptable excipients. The herein-disclosed compound comprises a first agent and a first polypeptide. The first polypeptide comprises a glycosaminoglycan (GAG)-binding peptide which is capable of binding a GAG in an alpha granule of a platelet.

In embodiments, the method further comprises a step of administering to the subject a second pharmaceutical composition comprising one or more of heparanase, thrombin and its fragment peptides, a protease-activated receptor 1 (PAR1) agonist or antagonist peptide, a protease-activated receptor 4 (PAR4) agonist or antagonist peptide, plasmin and its fragments, a metalloproteinase, a peroxidase, and/or a phosphohydrolase.

In embodiments, the second pharmaceutical composition promotes release of a compound from a platelet.

In embodiments, the second pharmaceutical composition is administered after the pharmaceutical composition is administered. In embodiments, the pharmaceutical composition is administered at least twice before the second pharmaceutical composition is administered.

In embodiments, the disease or disorder is a cancer. A cancer is generally disease caused by inappropriately high proliferation rate and/or inappropriately low rate of apoptosis.

In embodiments, the cancer is selected from acoustic neuroma; acute erythroleukemia; acute leukemia; acute lymphoblastic leukemia; acute lymphocytic leukemia; acute monocytic leukemia; acute myeloblastic leukemia; acute myelocytic leukemia; acute myelomonocytic leukemia; acute promyelocytic leukemia; adenocarcinoma; AIDS-related lymphoma; angiosarcoma; astrocytoma; basal cell carcinoma; B-cell lymphoma (including low grade/follicular non-Hodgkin's lymphoma); biliary tract cancer; bladder cancer; bone cancer; brain and central nervous system cancer; breast cancer; bronchogenic carcinoma; bulky disease non-Hodgkin's lymphoma; cancer of the digestive system; cancer of the head and neck; cancer of the peritoneum; cancer of the respiratory system; cancer of the urinary system; cervical cancer; chondrosarcoma; chordoma; choriocarcinoma; chronic leukemia; chronic lymphocytic leukemia; chronic myeloblastic leukemia; chronic myelocytic leukemia; colon and rectum cancer; connective tissue cancer; craniopharyngioma; cystadenocarcinoma; embryonal carcinoma; endometrial cancer; endotheliosarcoma; ependymoma; epithelial carcinoma; esophageal cancer; Ewing's tumor; eye cancer; fibrosarcoma; gastric cancer (including gastrointestinal cancer); glioblastoma; glioma; hairy cell leukemia; heavy chain disease; hemangioblastoma; hepatic carcinoma; hepatoma; high grade immunoblastic non-Hodgkin's lymphoma; high grade lymphoblastic non-Hodgkin's lymphoma; high grade small non-cleaved cell non-Hodgkin's lymphoma; Hodgkin's and non-Hodgkin's lymphoma; intermediate grade diffuse non-Hodgkin's lymphoma; intermediate grade/follicular non-Hodgkin's lymphoma; intra-epithelial neoplasm; kidney or renal cancer; larynx cancer; leiomyosarcoma; liposarcoma; liver cancer; lung cancer (e.g., small-cell lung cancer, non-small cell lung cancer, adenocarcinoma of the lung, and squamous carcinoma of the lung); lung carcinoma; lymphangioendotheliosarcoma; lymphangiosarcoma; lymphoma (Hodgkin's disease, non-Hodgkin's disease); mantle cell lymphoma; medullary carcinoma; medulloblastoma; Meigs' syndrome; melanoma; meningioma; mesothelioma; myeloma; myxosarcoma; neuroblastoma; nile duct carcinoma; oligodenroglioma; oral cavity cancer (lip, tongue, mouth, and pharynx); osteogenic sarcoma; ovarian cancer; pancreatic cancer; papillary adenocarcinomas; papillary carcinoma; pinealoma; polycythemia vera; post-transplant lymphoproliferative disorder (PTLD), as well as abnormal vascular proliferation associated with phakomatoses, edema (such as that associated with brain tumors); prostate cancer; rectal cancer; retinoblastoma; rhabdomyosarcoma; salivary gland carcinoma; sarcoma; schwannoma; sebaceous gland carcinoma; seminoma; skin cancer; small lymphocytic (SL) non-Hodgkin's lymphoma; squamous cell cancer; stomach cancer; sweat gland carcinoma; synovioma; testicular cancer; thyroid cancer; uterine or endometrial cancer; vulval cancer; Waldenstrom's Macroglobulinemia; and Wilm's tumor.

In embodiments, the disease or disorder the cancer is a proliferative disorder, e.g., a lymphoproliferative disease.

In embodiments, the disease of disorder is an injury, e.g., a burn, a spinal injury, an orthopedic injury, and wound.

In embodiments, the disease of disorder is hemophilia hemarthrosis.

In embodiments, the disease of disorder is inflammation, e.g., acute or chronic inflammation, including joint inflammation and lung inflammation.

In embodiments, the disease of disorder is a diabetic ulcer.

In embodiments, the disease of disorder is a side effect of an implant, graft, stent, or prosthesis.

In embodiments, a disease of disorder treated by methods of the present disclosure is caused by a defective gene. In these embodiments, the agent may be a recombinant polypeptide that replaces a missing or dysfunctional protein. Alternately, or additionally, the recombinant protein may be any one of the herein disclosed polypeptide-based agents, i.e., an antibody (or antigen-binding fragment thereof), a chemotherapeutic agent, an immune checkpoint inhibitor, a growth factor, a growth inhibitor, a protease/proteinase, a coagulation factor, an extracellular matrix protein, a hormone, an enzyme, a chemokine/chemoattractant, or a neurotrophin.

Some diseases caused by defects in genes may affect the synthesis of GAGs. As examples a defect in the Chondroitin Sulfate Proteoglycan 5 (CSPGS) on the long arm of Chromosome 3 can cause brain dysmorphogenesis and a defect in the DBQD1 gene causes micromelic dwarfism also called "Desbuquois dysplasia with hand anomalies'" and the gene abnormality can affect the syntesis of GAGs in platelets.

Administration of a herein disclosed pharmaceutical composition results in delivery of the loaded platelets into the bloodstream via intravenous or intra-arterial injection or infusion. Alternately, a herein disclosed pharmaceutical composition is re administered directly to the site of active disease. Other routes of administration include, for example, subcutaneous, interperitoneally, intramuscular, or intradermal injections.

The dosage of a pharmaceutical composition comprising herein disclosed loaded platelets as well as the dosing schedule could depend on various parameters, including, but not limited to, the disease being treated, the subject's general health, and the administering physician's discretion.

The dosage can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

Generally, dosages of a pharmaceutical composition comprising a specific amount of the agent loaded into platelets will be in the range of those when the agent is administered without being loaded into platelets. In embodiments, the dosage of agent in a herein disclosed pharmaceutical composition will be lower than the dosage of the agent that is not loaded into platelets, since the present invention provides increased target specificity and resistance to degradation of the agent in the subject.

Any pharmaceutical composition comprising herein disclosed loaded platelets can be administered in a single daily dose, or the total daily dosage can be administered in divided doses of two, three or four times daily. Furthermore, any pharmaceutical composition comprising herein disclosed loaded platelets could be administered continuously rather than intermittently throughout the dosage regimen.

Recombinant Polypeptide Expression

The invention further provides fusion proteins comprising an amino acid sequence of a recombinant polypeptide agent coupled (directly or indirectly) to a polypeptide comprising a glycosaminoglycan (GAG)-binding peptide.

Recombinant polypeptides comprising a GAG-binding peptide may express as separate peptides and ligated together. Alternately, recombinant polypeptides comprising a GAG-binding peptide are expressed as a single fusion protein that includes the polypeptide agent operably linked to a GAG-binding peptide.

Recombinant polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to express the recombinant polypeptides. The precise host cell used is not critical to the invention. A recombinant polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., Current Protocol in Molecular Biology, New York: John Wiley and Sons, 1997). The method of transformation or transfection and the choice of expression vehicle will depend on the host system selected. Transformation and transfection methods are described, e.g., in Ausubel et al., expression vehicles may be chosen from those provided, e.g., in Cloning Vectors: A Laboratory Manual (P. H. Pouwels et al., 1985, Supp. 1987).

Once the recombinant polypeptide of the invention is expressed, it may be isolated, concentrated, and/or purified As an example, recombinant polypeptide may be isolated using affinity chromatography. In one example, an antibody raised against the recombinant polypeptide may be attached to a column and used to isolate the recombinant polypeptide. Lysis and fractionation of polypeptide-harboring cells prior to affinity chromatography may be performed by standard methods (see, e.g., Ausubel et al.,). Alternatively, the recombinant polypeptide is isolated using a sequence tag, such as a hexahistidine tag, that binds to nickel column.

Once isolated, the recombinant protein can, if desired, be further purified, e.g., by high performance liquid chromatography (see, e.g., Fisher, Laboratory Techniques In Biochemistry and Molecular Biology, eds., Work and Burdon, Elsevier, 1980).

Polypeptides of the invention, particularly short peptide fragments, can also be produced by chemical synthesis (e.g., by the methods described in Solid Phase Peptide Synthesis, 2nd ed., 1984 The Pierce Chemical Co., Rockford, Ill.).

These general techniques of polypeptide expression and purification can also be used to produce and isolate useful peptide fragments or analogs (described herein).

Combination Therapies

In embodiments, any herein disclosed pharmaceutical composition or method of treatment may further comprise an additional agent that is not linked to a glycosaminoglycan (GAG)-binding peptide and/or loaded into a platelet. In one example of a combination therapy, a pharmaceutical composition comprises loaded platelets and the additional agent. In another example of a combination therapy, a subject is administered a first pharmaceutical composition comprising loaded platelets and a second pharmaceutical composition comprising the additional agent. Combination therapies may also include a first pharmaceutical composition comprising loaded platelets and a first additional agent and a second pharmaceutical composition comprising a second additional agent; here, the first and second additional agents may be the same or may be different agents. Any agent disclosed herein may serve as an additional agent.

In embodiments combination therapy involving more than one pharmaceutical composition, a first pharmaceutical composition may be administered before a second pharmaceutical composition, a first pharmaceutical composition may be administered after a second pharmaceutical composition, or a first pharmaceutical composition may be administered simultaneous with a second pharmaceutical composition.

Additionally, a combination therapy may combine a pharmaceutical composition of the present disclosure with another treatment regimen. Examples of other treatment regimen include radiotherapy, hormonal therapy, surgery, and cryosurgery. The treatment therapy may comprise any of the herein-described agent.

In embodiments, of a combination therapy, a chemotherapeutic agent is used in conjunction with a compound of the present disclosure. As examples, a combination therapy may comprise platelets loaded with one or both of a compound comprising a multikinase inhibitor (e.g., regorafenib) as agent, a compound comprising fumagillin as agent, and a chemotherapeutic agent; this combination may be used for treating pancreatic cancer, lung cancer, or colon cancer. A combination therapy may comprise platelets loaded with one or both of a compound comprising an EGFR inhibitor (e.g., Cetuximab) as agent, a compound comprising a multikinase inhibitor (e.g., regorafenib) as an active agent, and a chemotherapeutic agent; this may be used for treating lung cancer. A combination therapy may comprise platelets loaded with one or both or all three of a compound comprising an EGFR inhibitor (e.g., Cetuximab) as agent, a compound comprising a multikinase inhibitor (e.g., regorafenib) as agent, a compound comprising an ALK/ROS1/NTRK inhibitor (e.g., crizotinib) as agent, and a chemotherapeutic agent; this may be used for treating non-small cell lung cancer.

In additional embodiments, a combination therapy comprises platelets loaded with a VEGF inhibitor (e.g., Bevacizumab) and the drug Remdesivir; this may be used to treat Acute respiratory distress syndrome (ARDS), perhaps associated with COVID.

In embodiments of a combination therapy, a pharmaceutical composition may be administered before another treatment regimen, a pharmaceutical composition may be administered after another treatment regimen, or a pharmaceutical composition may be administered simultaneous with another treatment regimen.

Manufacturing Methods

Another aspect of the present disclosure is a method for manufacturing a loaded platelet. The method comprises steps of: obtaining a platelet; contacting the platelet in vitro or ex vivo with any herein-disclosed compound; and allowing contact between the platelet and the compound to progress until the compound is internalized by an alpha granule of the platelet, thereby producing a loaded platelet.

An agent is directly or indirectly linked to glycosaminoglycan (GAG)-binding peptide or a recombinant composition is synthesized which comprises a GAG-binding peptide and a therapeutic polypeptide to form a compound of the present disclosure. The compound is incubated with either autologous platelet rich plasma or allogenic platelet rich plasma from a blood bank for at least about 15 minutes at 37° C. The platelets loaded with the compound are infused into the patient, e.g., once weekly, since the half-life of platelets is four to seven days. When an agent has significant systemic toxicity, the platelets are washed using a suitable buffer to prevent infusion of an agent that has not been loaded into a platelet.

In embodiments, the method further comprises a step of contacting the platelet in vitro or ex vivo with an at least second compound in which the at least second compound comprises an at least second agent and an at least second polypeptide and the at least second polypeptide comprises an at least second glycosaminoglycan (GAG)-binding peptide which is capable of binding a GAG in an alpha granule of a platelet; and a step of allowing contact between the platelet and the at least second compound to progress until the at least second compound is internalized by an alpha granule of the platelet.

In embodiments, the step of contacting the platelet in vitro or ex vivo with the compound and the step of contacting the platelet in vitro or ex vivo with the at least second compound are sequential. In embodiments, the step of contacting the platelet in vitro or ex vivo with the compound and the step of contacting the platelet in vitro or ex vivo with the at least second compound are contemporaneous.

Kits

An aspect of the present disclosure is a kit for treating a disease or disorder. The kit comprising any herein-disclosed isolated platelet and instructions for use.

Another aspect of the present disclosure is a kit for treating a disease or disorder. The kit comprising any herein-disclosed pharmaceutical composition and instructions for use.

In embodiments, the kit further comprises an at least second pharmaceutical composition comprising one or more of heparanase, thrombin and its fragment peptides, a protease-activated receptor 1 (PAR1) agonist or antagonist peptide, a protease-activated receptor 4 (PAR4) agonist or antagonist peptide, plasmin and its fragments, a metalloproteinase, a peroxidase, and/or a phosphohydrolase.

Yet another aspect of the present disclosure is a kit for manufacturing a loaded platelet. The kit comprising any herein-disclosed compound and instructions for use.

The invention provides kits for the treatment or prevention of diseases or disorders involving sites of injury, inflammation, or tumor angiogenesis. In one embodiment, the kit includes a therapeutic or prophylactic composition containing an effective amount of platelets loaded with an agent in unit dosage form. In some embodiments, the kit comprises a sterile container that contains a therapeutic or prophylactic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired, a pharmaceutical composition comprising an isolated platelet of the present disclosure is provided together with instructions for administering it to a subject having or at risk of developing a disease or disorder. The instructions may include information about the use of the pharmaceutical composition for the treatment or prevention of the disease or for delivery of an isolated platelet to a tissue in need thereof. In other embodiments, the instructions include at least one of the following: description of the agent; dosage schedule and administration for treatment or prevention of the disease or symptoms thereof precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Any aspect or embodiment disclosed herein can be combined with any other aspect or embodiment as disclosed herein.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

Definitions

The terminology used herein is for the purpose of describing particular cases only and is not intended to be limiting.

As used herein, unless otherwise indicated, the terms “a”, “an” and “the” are intended to include the plural forms as well as the single forms, unless the context clearly indicates otherwise.

The terms “comprise”, “comprising”, “contain,” “containing,” “including”, “includes”, “having”, “has”, “with”, or variants thereof as used in either the present disclosure and/or in the claims, are intended to be inclusive in a manner similar to the term “comprising.”

The term “about” or “approximately” means within an acceptable error range for the particular value as determined by one of ordinary skill in the art, which will depend in part on how the value is measured or determined, e.g., the limitations of the measurement system. For example, “about” can mean 10% greater than or less than the stated value. In another example, “about” can mean within 1 or more than 1 standard deviation, per the practice in the given value. Where particular values are described in the application and claims, unless otherwise stated the term “about” should be assumed to mean an acceptable error range for the particular value.

The term “substantially” is meant to be a significant extent, for the most part; or essentially. In other words, the term substantially may mean nearly exact to the desired attribute or slightly different from the exact attribute. Substantially may be indistinguishable from the desired attribute. Substantially may be distinguishable from the desired attribute but the difference is unimportant or negligible.

The term “at least second” means a second, a third, a fourth, a fifth, a sixth, a seventh, an eighth, a ninth, a tenth, a twentieth, a thirtieth, a fourteenth, a fiftieth, a sixtieth, a seventieth, an eightieth, a ninetieth, a hundredth, or more and any iteration therebetween. The term “one or more” includes one, two, three, four, five, six, seven, eight, nine, ten, twenty, thirty, forty, fifty, sixty, seventy, eighty, ninety, one hundred, or more and any number therebetween.

The term “cargo” is meant a compound or agent that can be loaded into a platelet, e.g., an alpha granule of a platelet. Such loading occurs via a glycosaminoglycan (GAG)-binding peptide of a compound. In some embodiments, the term “agent” and “cargo” can be synonyms.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

EXAMPLES

Example 1: Glycosaminoglycan (GAG)-Binding Peptides Sequester Attached Cargos Into Alpha Granules of Platelets In this example, the ability of illustrative glycosaminoglycan (GAG)-binding peptides to direct loading of a cargo into alpha granules of platelets was determined.

Figure 1B:
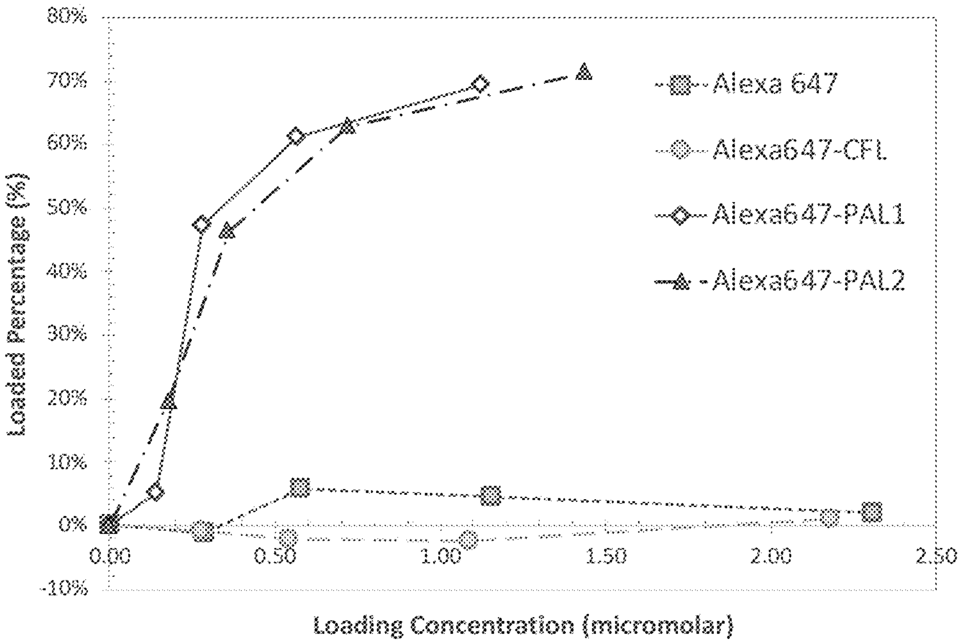

Alexa647-labeled GAG-binding peptides, identified in FIG. 1A and FIG. 1B as PAL1 and PAL2 and an Alexa647-labeled control peptide (a charge-free ligand (CFL) which served as a negative control), were tested for their binding affinity for glycosaminoglycans, such as chondroitin sulfate, and their abilities to enter platelets. PAL1 had an amino acid sequence of SEQ ID NO: 1, PAL2 had an amino acid sequence of SEQ ID NO: 2, CFL had an amino acid sequence of SEQ ID NO: 14.

A dose response curve of Alexa647-labeled peptides (or Alexa647 alone as a negative control) is shown in FIG. 1A. Alexa647-labeled peptides or Alexa647 alone were co-incubated with isolated platelets at 37° C. for one hour to allow for platelet loading. The respective platelet-loading ability was indicated by a decrease in fluorescence in supernatant following the incubation. For controls, identical experiments were performed without the incubation period (noted as "complete" in the figure). Platelets following co-incubation were then centrifuged at 800 g for 10-minutes to separate platelets from supernatant (noted as "loaded" in the figure).

As shown in FIG. 1A, there was a decrease in absorbance for PAL1 and PAL2 between the complete measurements and the loaded measurements. This reduction in absorbance from the supernatant indicates that these peptides had become sequestered from the supernatant and loaded into platelets. In contrast, absorbances of the Alexa647-labeled CFL conditions did not change after co-incubation with platelets; thus, the CFL peptides remained in the supernatant and were not loaded into platelets.

FIG. 1B represents the data in FIG. 1A normalized for each peptide experiment, i.e., normalization of a loaded condition to its complete condition. FIG. 1B shows that the illustrative GAG-binding peptides, PAL1 and PAL2, facilitates loading of an attached cargo into platelets whereas cargos attached to a charge-free ligand are unable to direct loading of the cargo into platelets.

To confirm that the Alexa647-labeled GAG-binding peptides were loaded into alpha granules of platelets, confocal microscopy was used. The platelets that were centrifuged in the experiments of FIG. 1A and FIG. 1B, were fixed in 2% paraformaldehyde and settled onto glass coverslips. After permeabilization, immunofluorescence staining was performed against PF4, which is a marker for alpha granules of platelets. Platelets were stained with Alexa568-secondary antibody. Images were collected through a Nikon-A1 laser-scanning microscope equipped with a 60× oil objective lens.

Figure 2A:
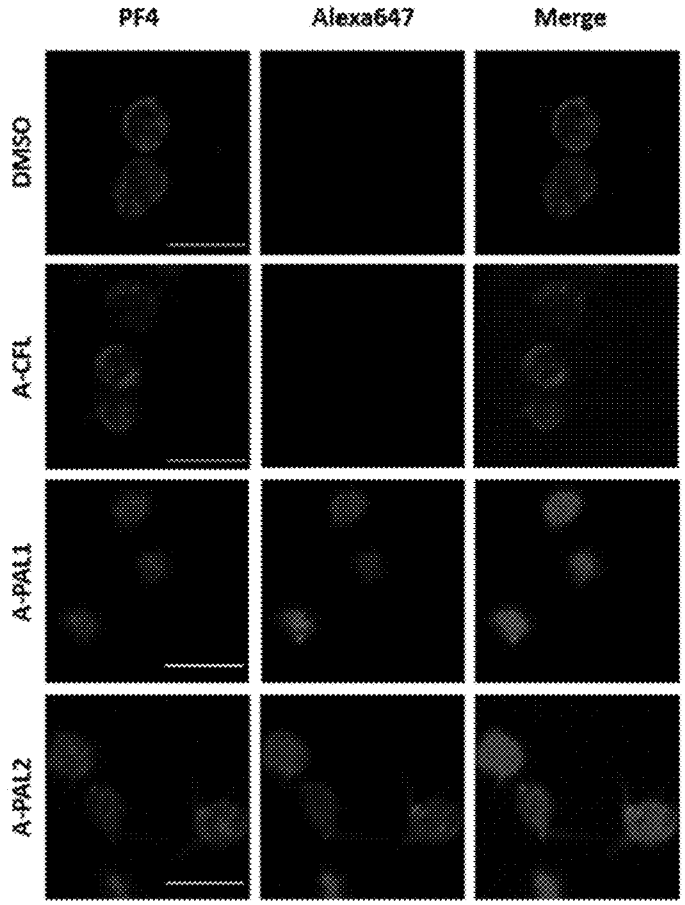
FIG. 2A are immunofluorescent images and FIG. 2B is a graph demonstrating the ability of illustrative glycosaminoglycan (GAG)-binding peptides to sequester attached cargos into alpha granules of platelets.

FIG. 2A are representative images with PF4 staining shown in red (left column) and the Alexa647 signal (from the free Alexa647, Alexa647-labeled GAG-binding peptide, or Alexa647-labeled CFL; middle column) shown in purple. Images were only adjusted for brightness and contrast for display. n>5 images were acquired for each experiment and regions of interest (ROIs) were selected based on PF4 intensity.

The merged images (right column) demonstrate colocalization of the alpha granule marker PF4 and the Alexa647 signal only when Alexa647 was the cargo for a GAG-binding peptide. Co-localization was not observed for free Alexa647 or when Alexa647 was the cargo of the CFL.

Figure 2B:
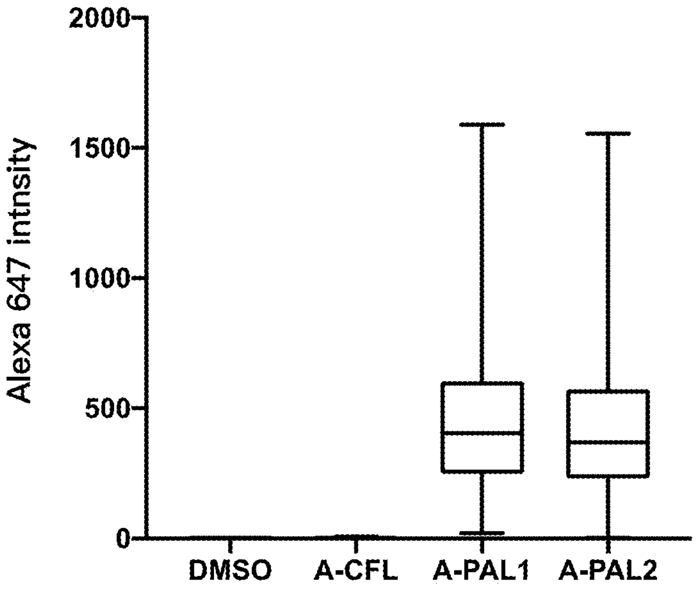

The Alexa647 intensities for each ROI were measured using ImageJ and plotted in box and whisker graph using Prism 8. FIG. 2B shows that the illustrative GAG-binding peptides, PAL1 and PAL2, facilitates loading of an attached cargo into alpha granules of platelets, whereas cargos attached to a charge-free ligand do not load into platelets, let alone into alpha granules of platelets.

These data demonstrate that the GAG-binding peptides of the present disclosure facilitate loading of any attached cargo into alpha granules of platelets.

Example 2: Glycosaminoglycan (GAG)-Binding Peptides Bind Glycosaminoglycans With High Affinities In this example, the binding affinities of illustrative glycosaminoglycan (GAG)-binding peptides to various glycosaminoglycans were determined.

Figure 3A:
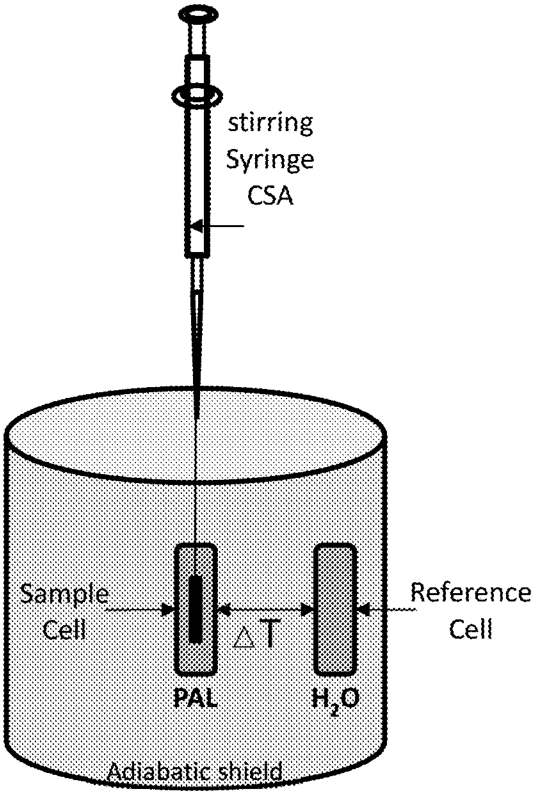
FIG. 3A is a schematic depicting isothermal titration calorimetry (ITC) experiments. Graphical representations of ITC dissociation kinetics for chondroitin sulfate A (CSA) titrated into cells withholding illustrative GAG-binding peptides are shown in FIG. 3B (for the GAG-binding peptide of SEQ ID NO: 1), FIG. 3C (for the GAG-binding peptide of SEQ ID NO: 2), and FIG. 3D for a charge-free ligand. The data of FIG. 3B is tabulated in FIG. 3E and the data of FIG. 3C is tabulated in FIG. 3F.

FIG. 3A is a schematic depicting the isothermal titration calorimetry (ITC) experiments performed in this example. Here, chondroitin sulfate A (CSA) was used to test affinities of illustrative GAG-binding peptides for glycosaminoglycan. 3 mM CSA was loaded into a syringe and CSA was titrated into the sample cell withholding a 0.25 mM solution of GAG-binding peptide or a charge-free ligand (CFL), which served as a negative control. Temperature was set at 22° C., the buffer was 5 mM Tris-HCl (pH 7.35), and 1% DMSO. Twenty-six injections of CSA were made, the first had a volume of 0.1 μl and the subsequent twenty-five had volumes of 1.5 μl each. In these experiments, the illustrative GAG-binding peptides were PAL1 and PAL2, respectively, having amino acid sequences of SEQ ID NO: 1 and SEQ ID NO: 2, and the CFL had an amino acid sequence of SEQ ID NO: 14.

Figure 3B:
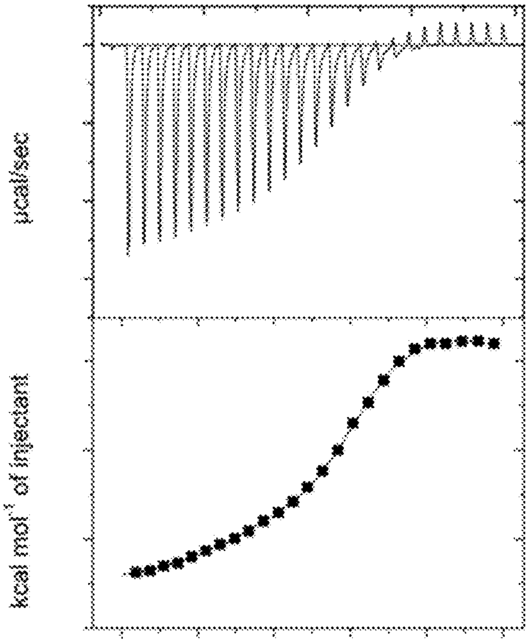
Figure 3C:
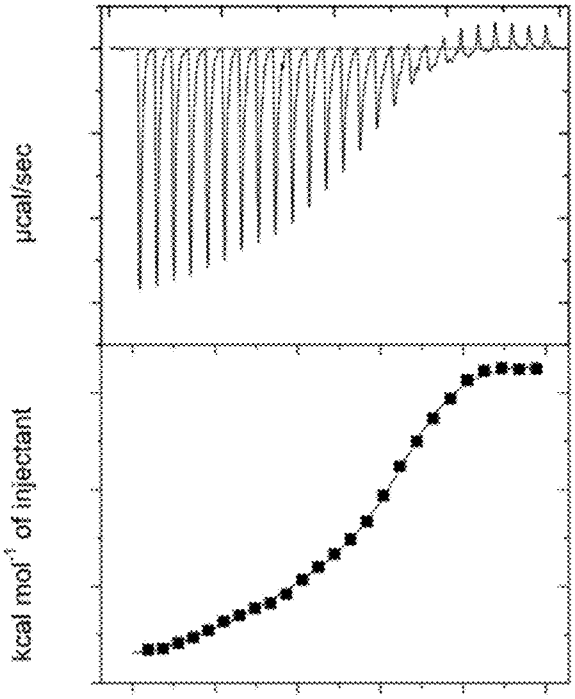
Figure 3D:
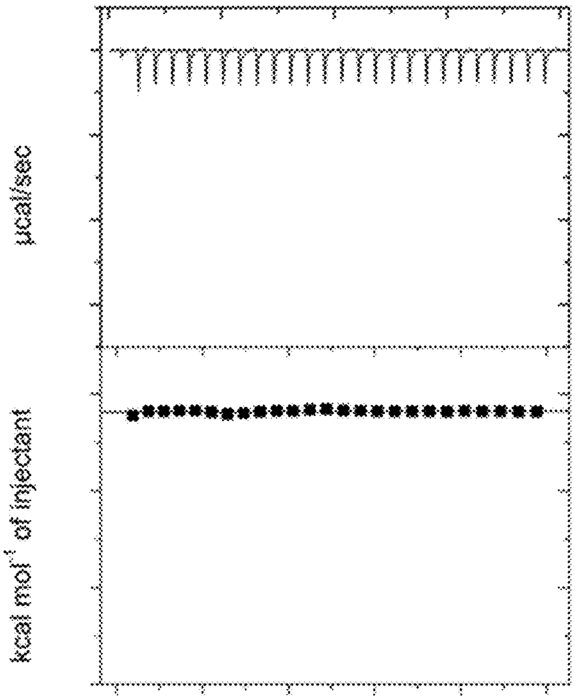

FIG. 3B to FIG. 3D show graphical representations of ITC dissociation kinetics for CSA titrated into cells withholding PAL1 (FIG. 3B), PAL2 (FIG. 3C), and CFL (FIG. 3D).

The data obtained during the experiments of FIG. 3B and FIG. 3C were used to determine dissociation constants for the CSA and GAG-binding peptide interactions; these were determined through titration curve fitting using sequential binding model. These data are shown in FIG. 3E (for PAL1) and FIG. 3F (for PAL2). These data show that the two illustrative GAG-binding peptides have high affinity for the glycosaminoglycan chondroitin sulfate A.

Figure 4:
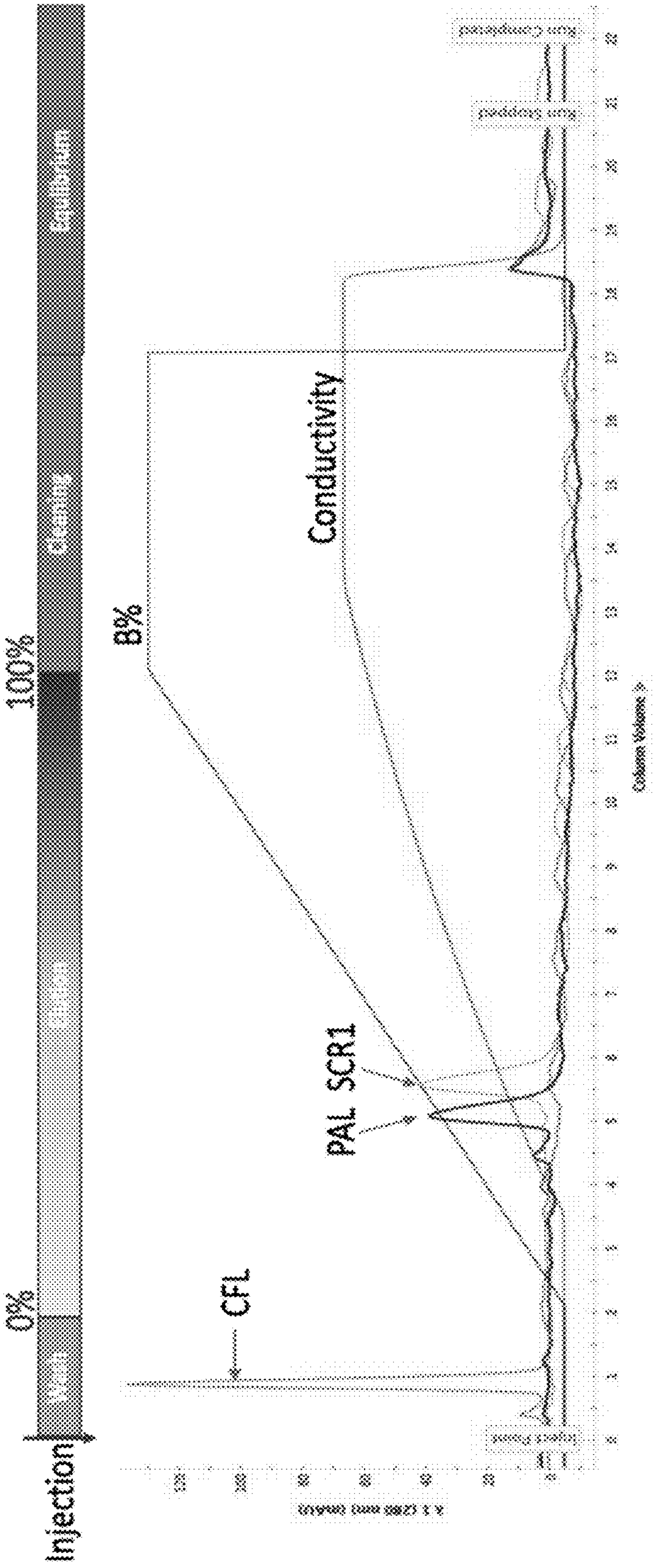
FIG. 4 shows affinity chromatography data for the three illustrative GAG-binding peptides of the previous figures albeit when binding to heparan sulfate (HS).

Additionally, the binding affinities for the two illustrative GAG-binding peptides and the CFL to heparan sulfate (HS) was determined using affinity chromatography. As shown in FIG. 4, CFL did not bind to HS whereas both illustrative GAG-binding peptides bind HS and with high affinity. Interestingly, the PAL2 peptide showed greater affinity for HS than PAL'.

These data demonstrate that the GAG-binding peptides of the present disclosure have high affinity for glycosaminoglycans which are present in alpha granules of platelets.

Example 3: Compounds Comprising a Glycosaminoglycan (GAG)-Binding Peptide and an Agent Load Into Alpha Granules of Platelets In this example, the ability of illustrative compounds comprising a glycosaminoglycan (GAG)-binding peptide and an agent to load into alpha granules of platelets was determined.

Two illustrative compounds of the present disclosure and two control compounds were constructed. The illustrative compounds included an agent (e.g., mNeonGreen) indirectly linked (via a nine amino acid linker) to a glycosaminoglycan (GAG)-binding peptide. In these experiments, the illustrative GAG-binding peptides were PAL1 and PAL2, respectively, having amino acid sequences of SEQ ID NO: 1 and SEQ ID NO: 2. The negative control compound included a charge-free ligand (CFL), having an amino acid sequence of SEQ ID NO: 14, indirectly linked (via the nine amino acid linker) to mNeonGreen. The positive control compound included PF4 (a natural platelet factor) indirectly linked (via the nine amino acid linker) to mNeonGreen. Prior to use, the compounds also included a His-tag for purification purposes, as well as a TEV-protease cleavage site, which facilitated removal of the His-tag. The compounds were identified as mCFL (for mNeon-L9-CFL), mPAL1 (for mNeon-L9-PAL1), mPAL2 (for mNeon-L9-PAL2), and PF4m (for PF4-L9-mNeon).

Platelets were co-incubated at 37° C. for an hour with one of the four compounds. After the incubation period, platelets were centrifuged at 800 g for 10-minutes. Then, the fluorescence absorbances of the "loaded" supernatants (at 505 nm) were measured and compared with the "complete" loading control, which was supernatants for each condition in which platelets were mixed with a compound and then immediately centrifuged, without an incubation period. The data were further normalized and the loading percentage for each group of experiments were plotted as shown in FIG. 5.

Figure 5:
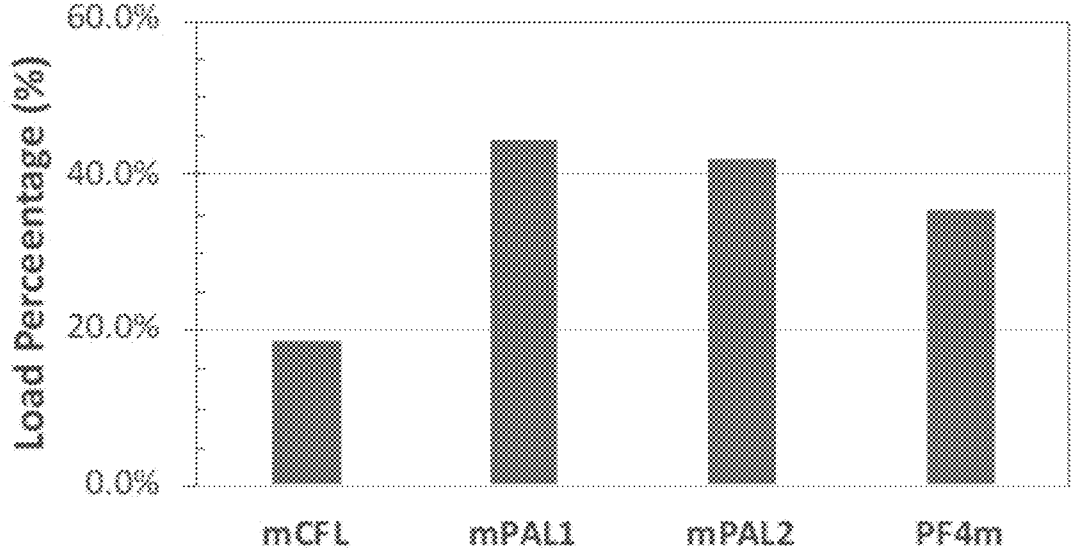
FIG. 5 is a graph demonstrating loading of an illustrative compound comprising a glycosaminoglycan (GAG)-binding peptide and an agent into platelets.

FIG. 5 shows that the two illustrative compounds had greater loading ability into platelets than the negative control and a slightly greater loading ability than the positive control PF4.

To confirm that the compounds comprising a GAG-binding peptide were loaded into alpha granules of platelets, confocal microscopy was used. The platelets that were centrifuged in the experiment of FIG. 5, were fixed in 2% paraformaldehyde and settled onto glass coverslips. After permeabilization, immunofluorescence staining was performed against PF4, which is a marker for alpha granules of platelets. Platelets were stained with Alexa568-secondary antibody. Images were collected through a Nikon-A1 laser-scanning microscope equipped with a 60× oil objective lens.

Figure 6A:
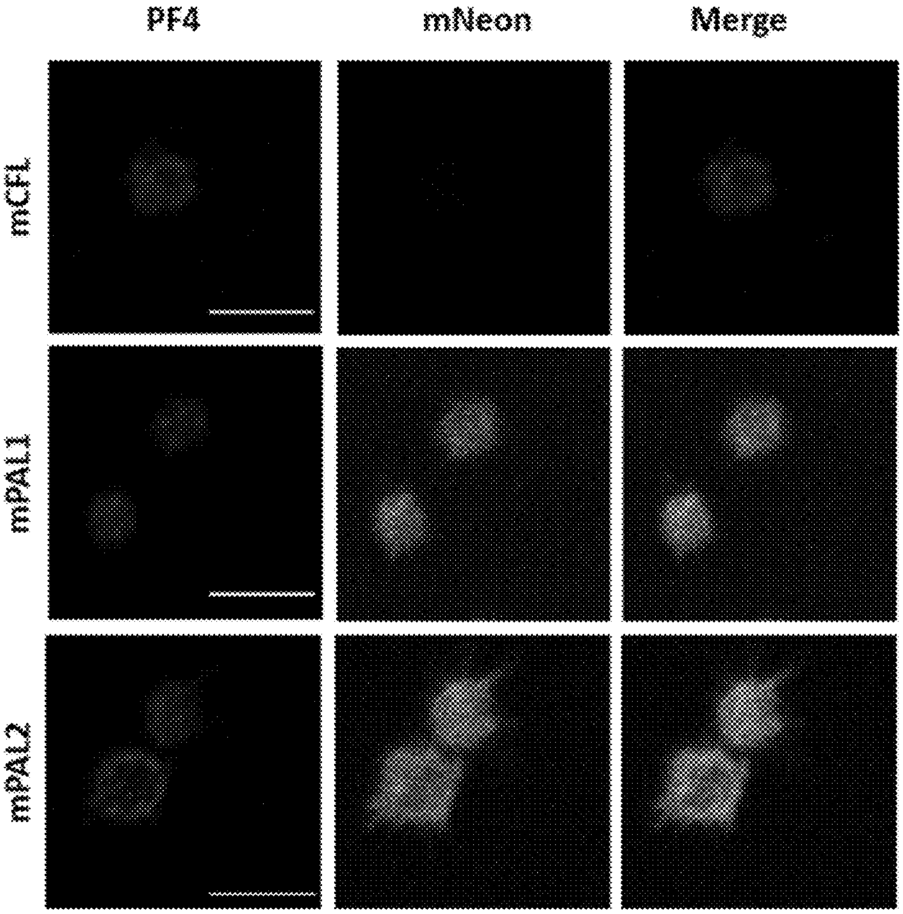
FIG. 6A are immunofluorescent images and FIG. 6B is a graph demonstrating the ability of illustrative compounds comprising a glycosaminoglycan (GAG)-binding peptide and an agent to load into alpha granules of platelets.

FIG. 6A are representative images with PF4 staining shown in red (left column) and the mNeon signal labeled green (middle column). Images were only adjusted for brightness and contrast for display. n>5 images were acquired for each experiment and regions of interest (ROIs) were selected based on PF4 intensity.

The merged images (right column) demonstrate colocalization of the alpha granule marker PF4 and the mNeon signal for the two illustrative compounds that comprise a GAG-binding peptide. Colocalization was not observed for the compound comprising the CFL.

Figure 6B:
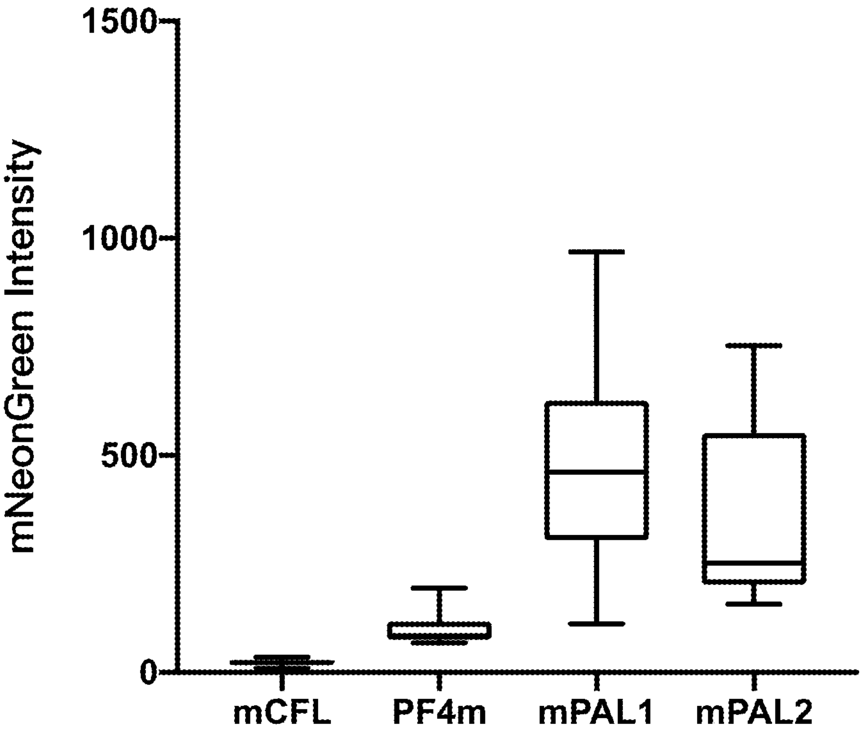

The mNeon intensities for each ROI were measured using ImageJ and plotted in box and whisker graph using Prism 8. FIG. 6B. shows that the illustrative compounds comprising the GAG-binding peptides load into alpha granules of platelets whereas compounds comprising a charge-free ligand do not load into platelets, let alone into alpha granules of platelets.

These data demonstrate that compounds of the present disclosure which comprise a GAG-binding peptide and an agent load into alpha granules of platelets.

Example 4: Compounds Comprising a Glycosaminoglycan (GAG)-Binding Peptide and an Agent Bind Glycosaminoglycans With High Affinities In this example, the binding affinities of illustrative compounds of the present disclosure (which comprise a glycosaminoglycan (GAG)-binding peptide and an agent) to various glycosaminoglycans were determined.

Isothermal titration calorimetry (ITC) experiments as depicted in FIG. 3A and as described in Example 2 were performed in this example, yet with illustrative compounds of the present disclosure, with a negative control compound. Like the experiments of Example 2, here, the titration buffer was 5 mM Tris-HCl (pH 7.35) and the temperature set at 22° C.; however, unlike the experiments of Example 2, the buffer lacked DMSO.

Figure 7A:
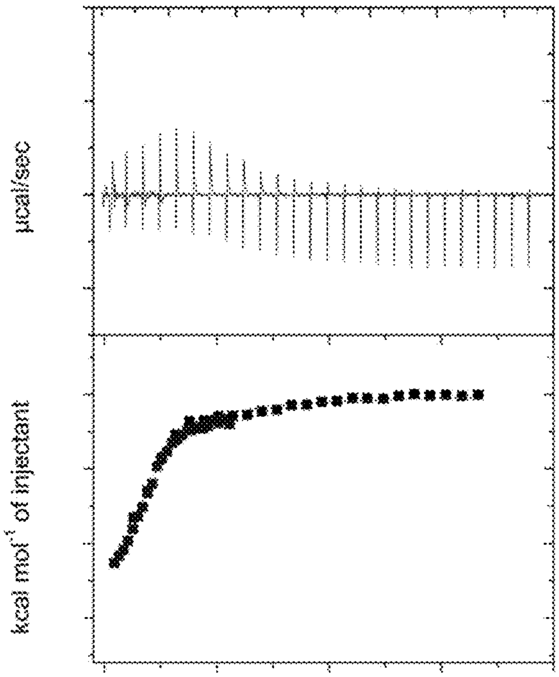
FIG. 7A to FIG. 7C include graphical representations of ITC dissociation kinetics for chondroitin sulfate A (CSA) titrated into cells withholding the illustrative compound comprising PAL1 (FIG. 7A), the illustrative compound comprising PAL2 (FIG. 7B), and the control compound comprising CFL (FIG. 7C). The data of FIG. 7A is tabulated in FIG. 7D, the data of FIG. 7B is tabulated in FIG. 7E, and the data of FIG. 7C is tabulated in FIG. 7F.
Figure 7B:
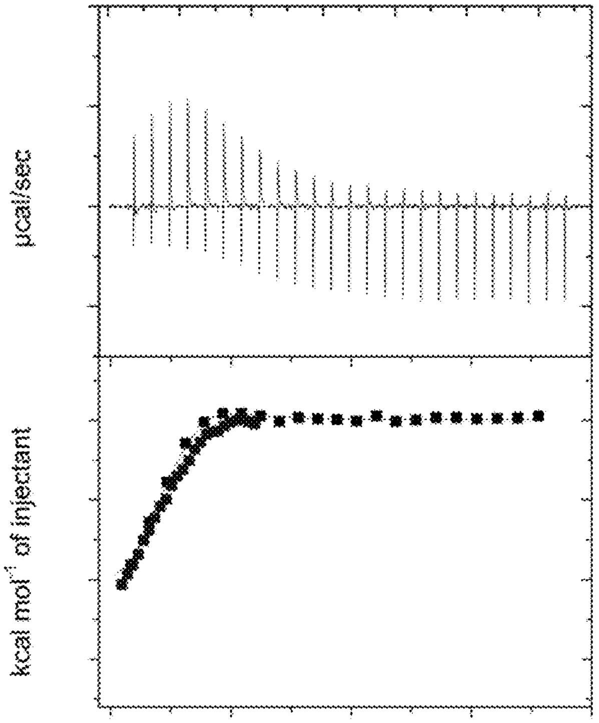
Figure 7C:
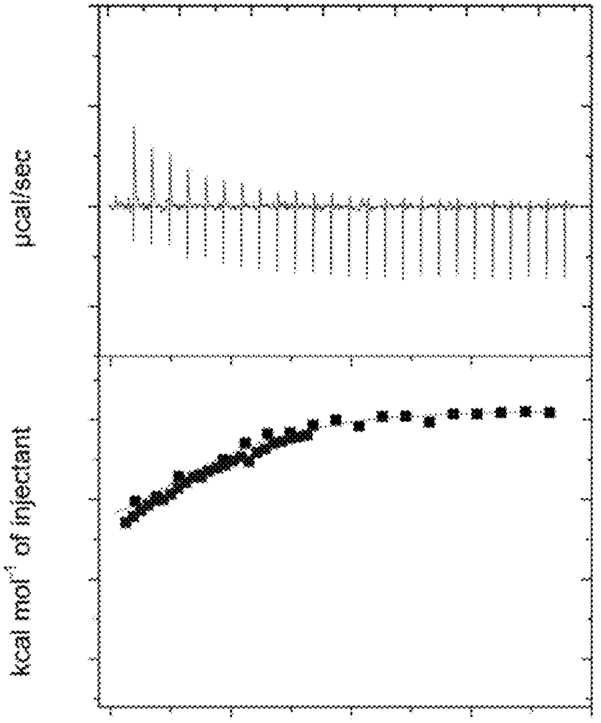

FIG. 7A to FIG. 7C show graphical representations of ITC dissociation kinetics for CSA titrated into cells withholding the illustrative compound comprising PAL1 (FIG. 7A), the illustrative compound comprising PAL2 (FIG. 7B), and the negative control compound comprising CFL (FIG. 7C). These compounds comprised mNeonGreen as its agent.

The data obtained during the experiments of FIG. 7B to FIG. 7C were used to determine dissociation constants for the CSA and compound interactions; these were determined through titration curve fitting using sequential binding model. These data are shown in FIG. 7C (for the illustrative compound comprising PAL1), FIG. 7D (for the illustrative compound comprising PAL2), and FIG. 7E (for the negative control compound comprising CFL). These data show that the two illustrative GAG-binding peptides have high affinity for the glycosaminoglycan chondroitin sulfate A.

Figure 8:
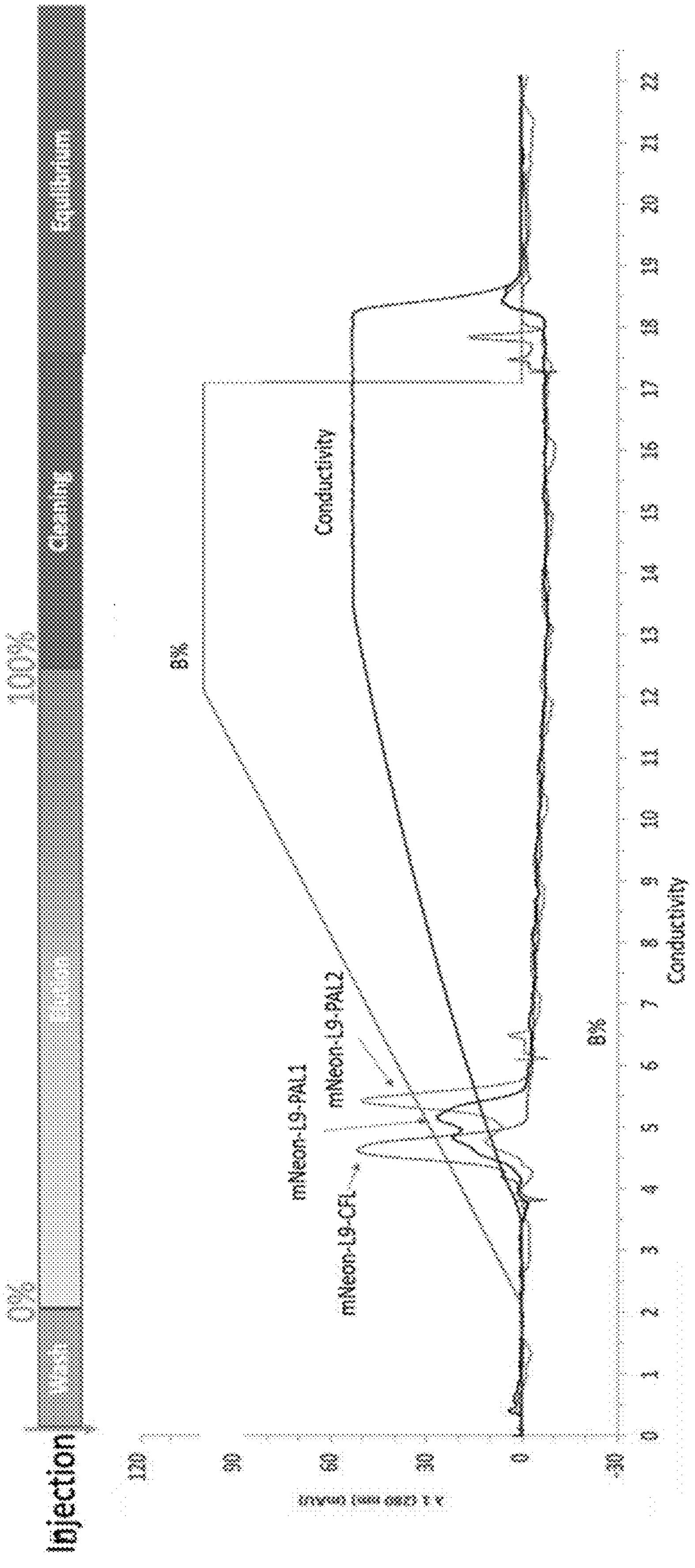
FIG. 8 shows affinity chromatography data for the three illustrative compounds of the previous figures albeit when binding to heparan sulfate (HS).

Additionally, the binding affinities for the two illustrative GAG-binding peptide containing compounds and the CFL to heparan sulfate (HS) was determined using affinity chromatography. As shown in FIG. 8, compounds comprising either GAG-binding peptide bind HS with high affinity. Notably, the relative binding affinities of the two illustrative GAG-binding peptides to HS were similar to that observed in prior experiments in that mPAL2 binds HS tighter than mPAL1 as PAL2 binds HS tighter than PALL Compounds comprising the control peptide (mCFL) has some residual binding ability and retained on the HS column which was eluted at a relatively low concentration of salt, perhaps due to charged character of the compound's agent (e.g., mNeonGreen).

These data demonstrate that the illustrative compounds of the present disclosure comprising glycosaminoglycan (GAG)-binding peptides and an agent have high affinity for glycosaminoglycans, which are in alpha granules of platelets.

Example 5: Identification of Sequence Specificity Important for a Glycosaminoglycan (GAG)-Binding Peptide's Ability to Bind Glycosaminoglycans In this example, the binding affinities of additional illustrative compounds comprising glycosaminoglycan (GAG)-binding peptides to a various glycosaminoglycan were determined. More specifically, alanine-scanning mutagenesis of the GAG-binding peptide (of SEQ ID NO: 1) produced additional illustrative GAG-binding peptides that differed by one amino acid, which were then indirectly linked to an agent (e.g., mNeonGreen), as described in Example 3.

Isothermal titration calorimetry (ITC) experiments as depicted in FIG. 3A and as described in Example 4 were performed in this example, yet with additional illustrative compounds of the present disclosure.

Figure 9A:
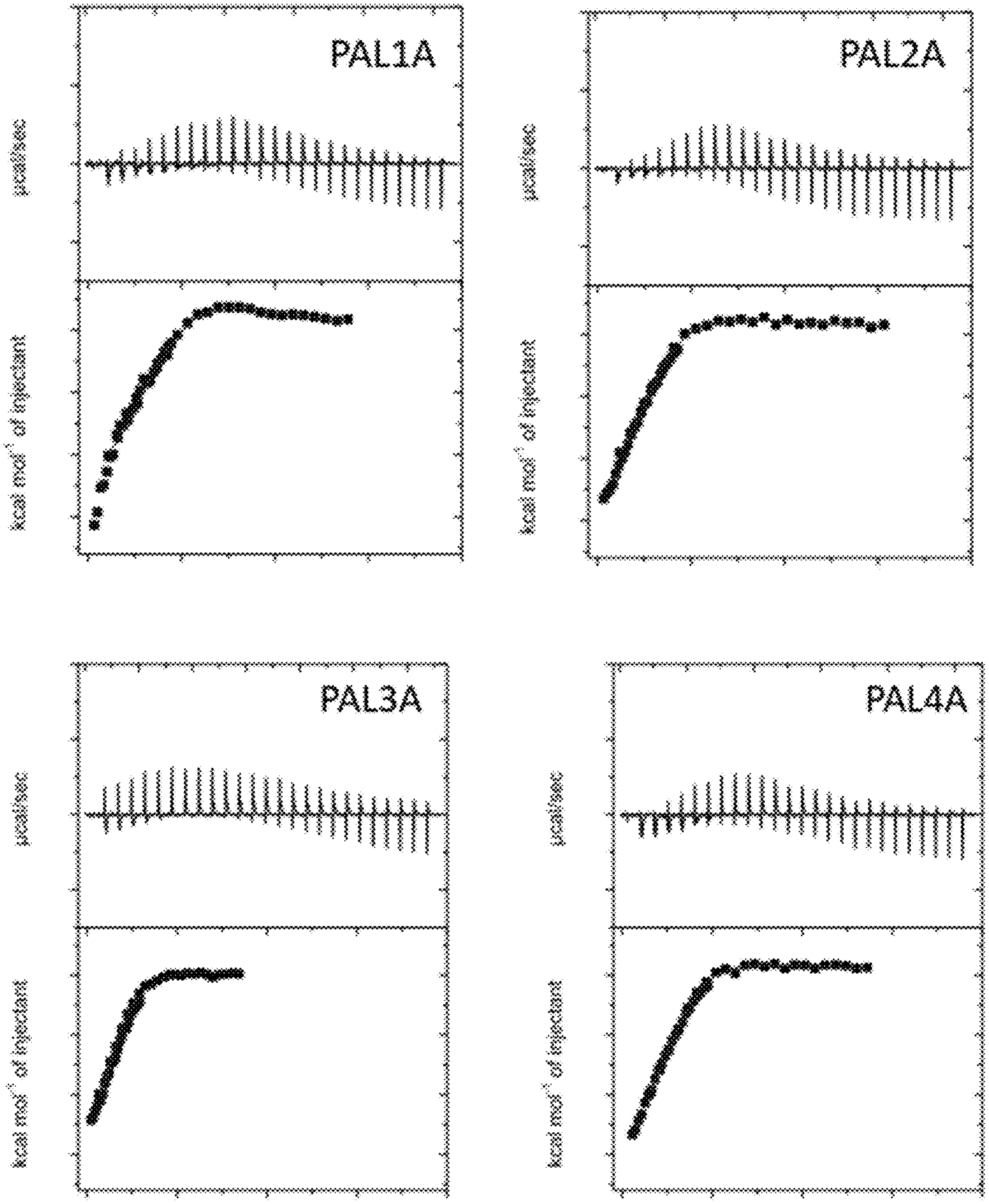
FIG. 9A include graphical representations of ITC dissociation kinetics for chondroitin sulfate A (CSA) titrated into cells withholding the additional illustrative compounds. These additional illustrative compounds are identified as PAL1A to PAL11A and, respectively, comprise GAG-binding peptides having amino acid sequences of SEQ ID NO: 3 to SEQ ID NO: 13. The data of FIG. 9A is tabulated in FIG. 9B to FIG. 9L.
Figure 9A:
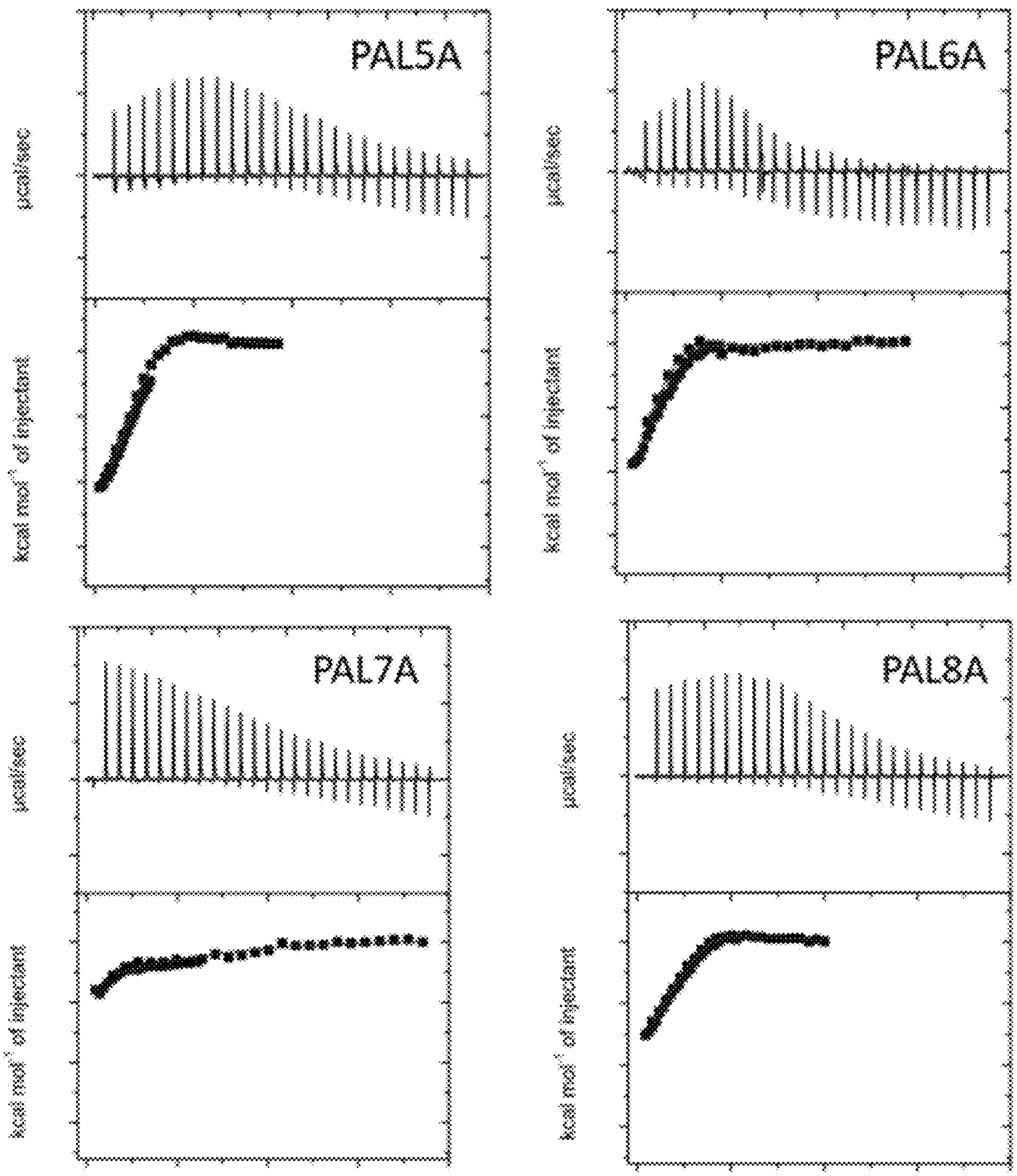
Figure 9A:
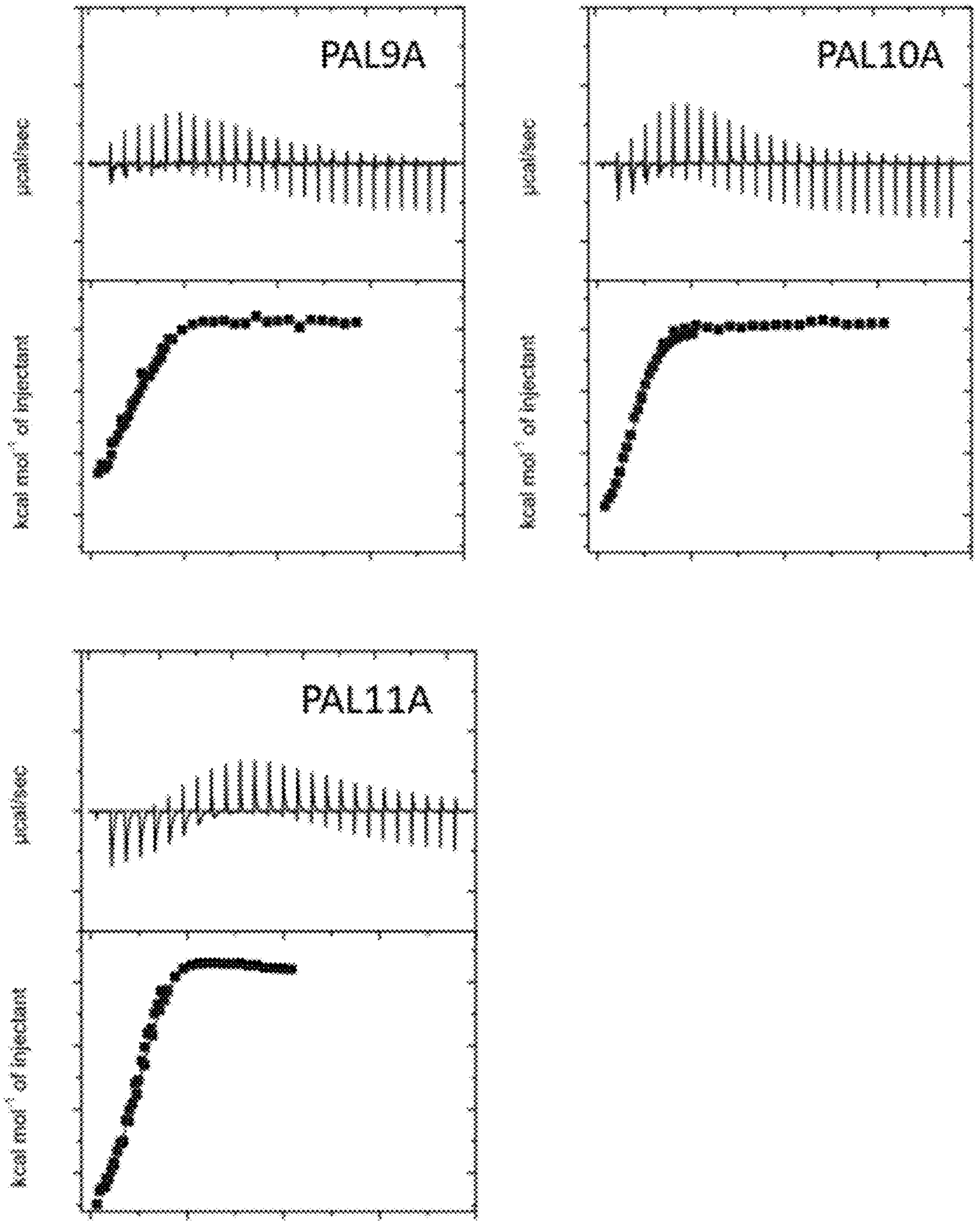

In FIG. 9A, the compounds are identified as PAL1A to PAL11A. These illustrative compounds have GAG-binding peptides having amino acid sequences of SEQ ID NO: 3 to SEQ ID NO: 13. In particular, the GAG-binding peptide of PAL1A differed from SEQ ID NO: 1 by having an alanine at position 1; the GAG-binding peptide of PAL2A differed from SEQ ID NO: 1 by having an alanine at position 2; and the GAG-binding peptide of PAL3A differed from SEQ ID NO: 1 by having an alanine at position 3.

FIG. 9A shows graphical representations of ITC dissociation kinetics for CSA titrated into cells withholding one of the illustrative compounds identified as PAL1A to PAL11A. As seen in the respective ITC curves generated by CSA titration into sample cells containing each listed compound, both charges and sequences are important in interacting with chondroitin sulfate A.

The data obtained during the experiments of FIG. 9A were used to determine dissociation constants for the CSA and additional illustrative compound interactions; these were determined through titration curve fitting using sequential binding model. These data are shown in FIG. 9B to FIG. 9L (respectively for PAL1A to PAL11A). These data show that the additional illustrative compounds have variable affinity for the glycosaminoglycan chondroitin sulfate A.

Figure 9M:
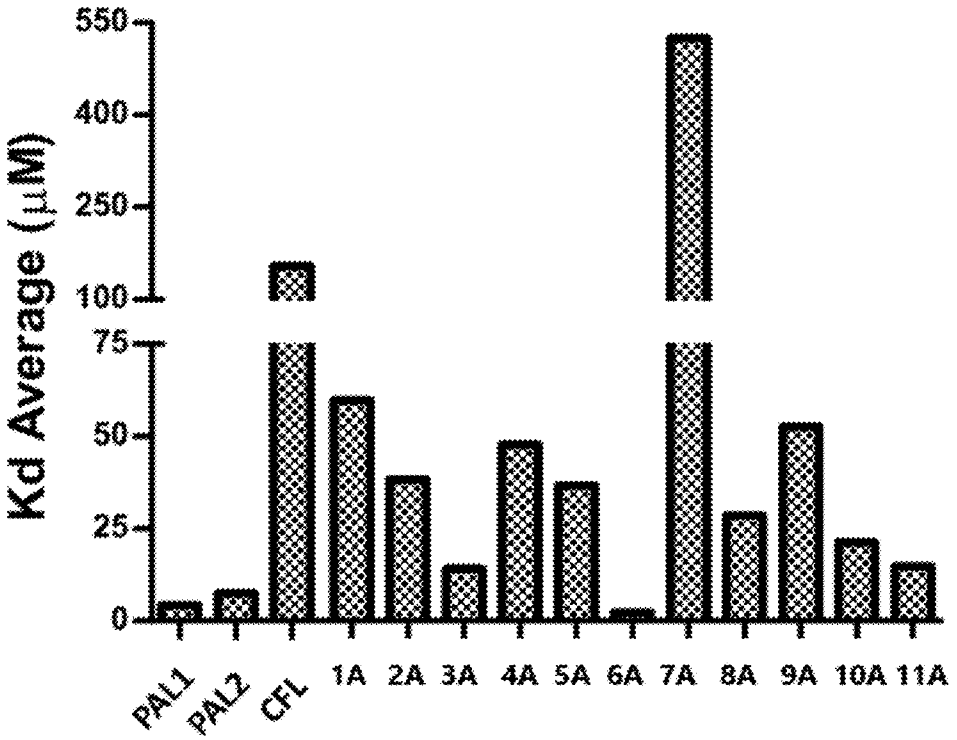
FIG. 9M is a graph depicting the average dissociation constant for the additional illustrative compounds and a negative control compound.

FIG. 9M is a graph depicting the average dissociation constants for the illustrative compounds and the control compound. This graph shows various magnitudes of CSA-binding affinities among the compounds. In the graph, to data identified as "1A" represents the "PAL1A" compound, to data identified as "2A" represents the "PAL2A" compound, and so forth.

Notably, those illustrative compounds having an alanine at its position 1, 4, 7, or 9 had the lowest, poorest affinity. Thereby demonstrating improvements in binding ability when a GAG-binding peptide has a proline, arginine, and/or isoleucine at those positions.

Critical amino acids such as proline, arginine, and isoleucine in positions affect the affinity of the binding. Interestingly, these amino acids include the positively charged arginine as expected and also non-charged proline and isoleucine that may contribute through maintain special conformation.

These data demonstrate that the additional compounds having GAG-binding peptides that differed in the position of a charged amino acid have variable affinity for glycosaminoglycans. And, critical residues (positions 1, 4, 7, and 9 with respect to SEQ ID NO: 1) and specific amino acids (such as proline, arginine, and isoleucine) affect the binding affinity of a GAG-binding peptide to a glycosaminoglycan, e.g., in an alpha granule of a platelet.

Example 6: Illustrative Methods for Conjugating a Glycosaminoglycan (GAG)-Binding Peptide to an Agent When Forming a Compound of the Present Disclosure In this example, an agent is conjugated to a glycosaminoglycan (GAG)-binding peptide to form an illustrative compound of the present disclosure.

Figure 10A:
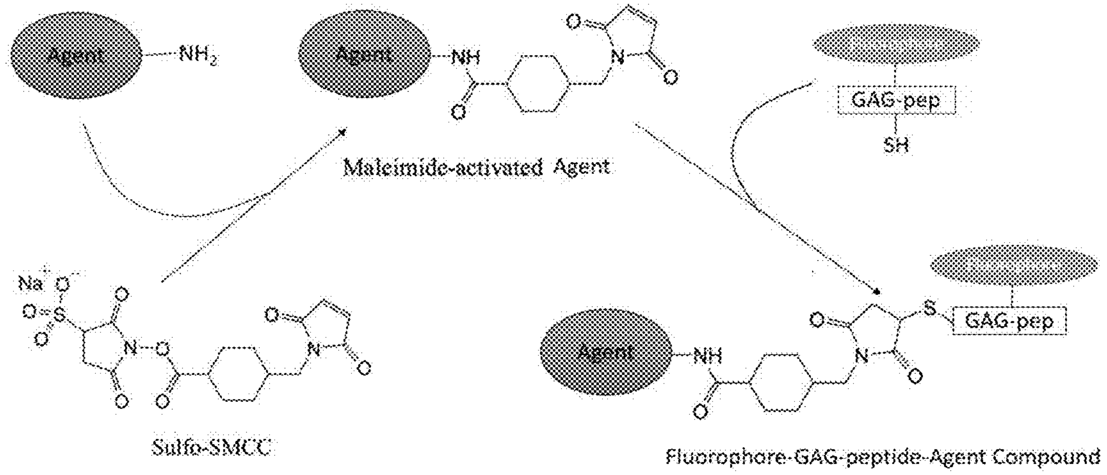
FIG. 10A is a diagram showing illustrative steps in conjugating a GAG-binding peptide to an agent when forming a compound of the present disclosure.

As shown in FIG. 10A, an agent is conjugated to a GAG-binding peptide using a maleimide reaction, thereby forming a compound of the present disclosure. Other conjugation reactions known in the art, e.g., succinimidyl ester reaction or an enzymatic reaction, may be used. In FIG. 10A, the GAG-binding peptide (shown in FIG. 10A as "GAG-pep") comprises a fluorescent moiety; in certain embodiments of the present disclosure, a fluorescent moiety is not included in a compound.

To further demonstrate the ability of a compound of the present disclosure to load its cargo into platelets (as described in the above examples), here, an illustrative compound comprising a GAG-binding peptide and a therapeutic antibody (DC101, a VEGFR2 inhibitor) was produced. Using similar methods, agents other than antibodies can be used to produce a compound of the present disclosure. As examples, the agent may be a chemotherapeutic agent, a cytotoxic compound, a small molecule, a fluorescent moiety, radioactive element, or a factor that inhibits cellular proliferation, angiogenesis, inflammation, immunity, or another physiological process mediated by or associated with a platelet.

The ability of the illustrative compound (comprising an antibody as agent) and further comprising a fluorescent moiety to be loaded into alpha granules of platelets was determined.

Figure 10B:
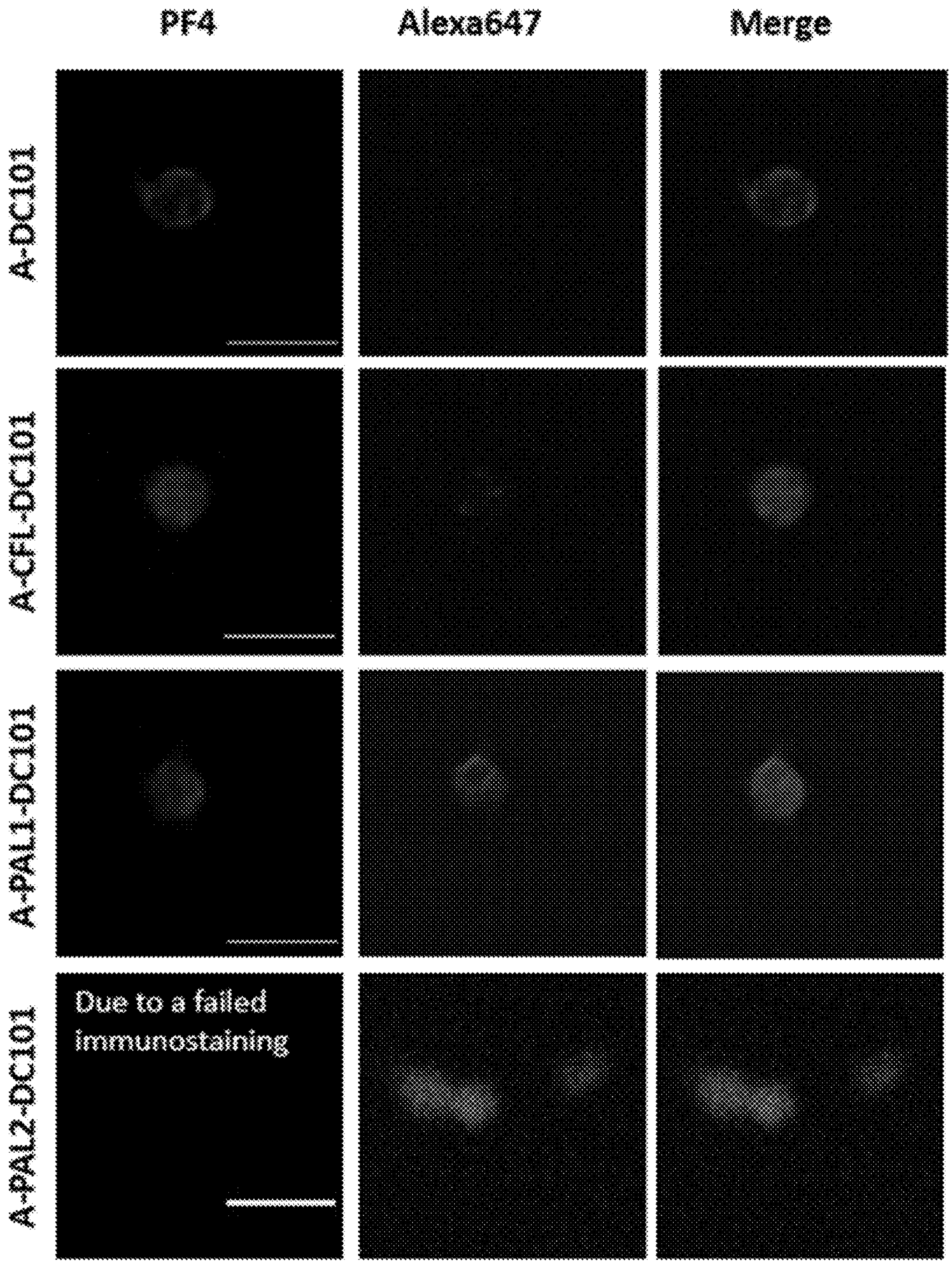
FIG. 10B are immunofluorescent images and FIG. 10C is a graph demonstrating the ability of illustrative compounds comprising a glycosaminoglycan (GAG)-binding peptide and an agent to load into alpha granules of platelets.

Four compounds were prepared: an Alexa647-labeled DC101 as a negative control (identified FIG. 10B as A-DC101), an Alexa647-labeled compound comprising the charge-free ligand (CFL) of SEQ ID NO: 14 and the DC101 antibody (identified FIG. 10B as A-CLF-DC101), an Alexa647-labeled compound comprising the GAG-binding peptide of SEQ ID NO: 1 and the DC101 antibody (identified FIG. 10B as A-PAL1-DC101), and Alexa647-labeled compound comprising the GAG-binding peptide of SEQ ID NO: 2 and the DC101 antibody (identified FIG. 10B as A-PAL2-DC101).

Platelets were co-incubated with each compound for one hour at 37° C. The platelets were then centrifuged for 10-minutes at 800 g, fixed in 2% paraformaldehyde, and settled onto glass coverslips. After permeabilization, immunofluorescence staining was performed against PF4 in platelets and further stained with Alexa568-secondary antibody. The images were collected through a Nikon-A1 laser-scanning microscope equipped with a 60× oil objective lens.

In the representative images of FIG. 10B, PF4 staining was displayed in red (left column) and the Alexa647 signal was shown in purple (middle column). Images were only adjusted for brightness and contrast for display. n>5 images were acquired for each experiment and regions of interest (ROIs) were selected based on PF4 intensity.

The merged images (right column) demonstrate colocalization of the alpha granule marker PF4 and the Alexa647 signal only when Alexa647 was associated with a GAG-binding peptide, but not when Alexa647 was associated with the CFL or with the DC101 antibody alone. Unfortunately, the PF4 immunostaining reaction failed for the platelets co-incubated with the A-PAL2-DC101 compound. Therefore, ROIs were selected based on Alexa647 intensity for this group.

Figure 10C:
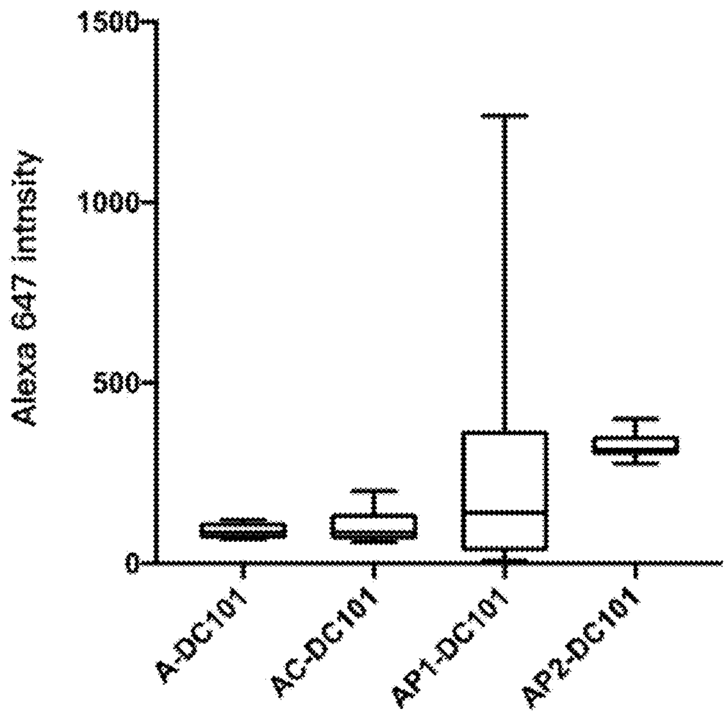

The Alexa647 intensities for each ROI were measured using ImageJ and plotted in box and whisker graph using Prism 8. As shown in FIG. 10C, the two illustrative compounds of the present disclosure load into alpha granules of platelets whereas the compound comprising a charge-free ligand or the compound comprising an antibody (without a GAG-binding peptide) do not load into platelets, let alone into alpha granules of platelets.

These data demonstrate that compounds of the present disclosure comprising a GAG-binding peptide and an agent load into alpha granules of platelets.

Example 7: Illustrative Methods for Manufacturing an Isolated Platelet Loaded With a Compound of the Present Disclosure In this example, an isolated platelet is loaded with a compound of the present disclosure.

An isolated platelet is obtained. The platelet may be a synthetic platelet, an allogeneic platelet, an autologous platelet, or a modified heterologous platelet. In embodiments, the platelet is obtained from platelet rich plasma.

The platelet is contacted in vitro or ex vivo with a compound of the present disclosure. The compound comprises a first agent and a first polypeptide. The first polypeptide comprises a glycosaminoglycan (GAG)-binding peptide which can bind a GAG in an alpha granule of a platelet. Preferably, the GAG-binding peptide preferentially binds, at least, to chondroitin sulfate (CS).

Contact continues at a suitable temperature, media composition (including salt concentration, pH, nutrients), and length of time until the compound is internalized by an alpha granule of the platelet. As such, a loaded platelet in obtained. Often the temperature is the body temperature from which a platelet is obtained or to be administered, e.g., 37° C. Similarly, the pH of the composition is near the pH of blood/plasma from which a platelet is obtained or to be administered, e.g., a pH of about 7.4.

Any agent listed in the present disclosure or known in the art may be used in this example. The agent may be an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet.

In some embodiments, the first agent may be one of an EGFR inhibitor (e.g., Cetuximab), a VEGF inhibitor (e.g., Bevacizumab), a PDL1 inhibitor (e.g., Pembrolizumab), an FN1 inhibitor (e.g., Ocriplasmin), a multikinase inhibitor (e.g., regorafenib), a FGFR2 antagonist (e.g., thalidomide), thrombin and its analogues, CSF3R agonist (e.g., Filgrastim), PSMB5 inhibitor (e.g., Bortezomib), fumagillin, or an ALK/ROS1/NTRK inhibitor (e.g., crizotinib).

In some cases, the loaded platelet is contacted in vitro or ex vivo with a second compound. The second compound comprises a second agent and a second polypeptide. The second polypeptide comprises a second glycosaminoglycan (GAG)-binding peptide which can bind a GAG in an alpha granule of a platelet. Contact continues at a suitable temperature, media composition, and length of time until the second compound is internalized by the alpha granule of the platelet.

The second agent may be one of an EGFR inhibitor (e.g., Cetuximab), a VEGF inhibitor (e.g., Bevacizumab), a PDL1 inhibitor (e.g., Pembrolizumab), an FN1 inhibitor (e.g., Ocriplasmin), a multikinase inhibitor (e.g., regorafenib), a FGFR2 antagonist (e.g., thalidomide), thrombin and its analogues, CSF3R agonist (e.g., Filgrastim), PSMB5 inhibitor (e.g., Bortezomib), fumagillin, or an ALK/ROS1/NTRK inhibitor (e.g., crizotinib).

The agent and the second agent may be the same or may be different; the first polypeptide and the second polypeptide may be the same or may be different; and/or the first GAG-binding peptide and the second GAG-binding peptide may be the same or may be different.

As examples, the first and second agents may be: a VEGF inhibitor (e.g., Bevacizumab) and a PDL1 inhibitor (e.g., Pembrolizumab); or an EGFR inhibitor (e.g., Cetuximab) and a multikinase inhibitor (e.g., regorafenib); or fumagillin and a multikinase inhibitor (e.g., regorafenib).

A third compound comprising a third polypeptide and a third agent, e.g., an EGFR inhibitor (e.g., Cetuximab) and a multikinase inhibitor (e.g., regorafenib), and an ALK/ROS1/NTRK inhibitor (e.g., crizotinib) may be combined.

In embodiments, the compound and the second compound are loaded sequentially, as described above. In alternate embodiments, the compound and the second compound are loaded simultaneously.

Preferably, an isolated platelet comprises 1 to 1000 copies of the compound and/or comprises 1 to 1000 copies of the second compound. In embodiments, the 1 to 1000 copies are loaded into an alpha granule of the platelet.

The loaded platelets thus manufactured may be combined with one or more pharmaceutically-acceptable excipients to produce a pharmaceutical composition.

Additionally, a pharmaceutical composition may be produced by combining a first isolated platelet loaded with a first compound of the present disclosure, a second isolated platelet loaded with a second (or third) compound of the present disclosure, and one or more pharmaceutically-acceptable excipients. Any first and/or second agents mentioned above and any combinations thereof may be used.

Example 8: Illustrative Methods for Treating a Disease or Disorder by Administering to a Subject Isolated Platelets Loaded With a Compound of the Present Disclosure In this example, isolated platelets loaded with a compound of the present disclosure are administered to a subject in need, e.g., who has a disease or a disorder.

Here, a subject in need is administered (e.g., by infusion or injection) a therapeutically-effective amount of one or more pharmaceutical compositions, each comprising platelets loaded with one or more compounds of the present disclosure.

Any agent listed in the present disclosure or known in the art may be used in this example. The agent may be an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet.

In some embodiments, the one or more compounds may comprise an agent selected from EGFR inhibitor (e.g., Cetuximab), a VEGF inhibitor (e.g., Bevacizumab), a PDL1 inhibitor (e.g., Pembrolizumab), an FN1 inhibitor (e.g., Ocriplasmin), a multikinase inhibitor (e.g., regorafenib), a FGFR2 antagonist (e.g., thalidomide), thrombin and its analogues, CSF3R agonist (e.g., Filgrastim), PSMB5 inhibitor (e.g., Bortezomib), fumagillin, and an ALK/ROS1/NTRK inhibitor (e.g., crizotinib).

The platelets may be loaded with a combination compounds of the present disclosure. As examples, a first and second agent may be a VEGF inhibitor (e.g., Bevacizumab) and a PDL1 inhibitor (e.g., Pembrolizumab); this may be used for treating pancreatic cancer. Also, a first and second agent may be an EGFR inhibitor (e.g., Cetuximab) and a multikinase inhibitor (e.g., regorafenib); this may be used for treating lung cancer. A first and second agent may be a multikinase inhibitor (e.g., regorafenib) and fumagillin; this may be used for treating pancreatic cancer, lung cancer, or colon Cancer.

Alternately, more than two compounds may be used, with a first, second, and third agent being an EGFR inhibitor (e.g., Cetuximab) and a multikinase inhibitor (e.g., regorafenib), and an ALK/ROS1/NTRK inhibitor (e.g., crizotinib); this may be used for treating non-small cell lung cancer.

The subject may further be administered a second pharmaceutical composition comprising one or more of heparanase, thrombin and its fragment peptides, a protease-activated receptor 1 (PAR1) agonist or antagonist peptide, a protease-activated receptor 4 (PAR4) agonist or antagonist peptide, plasmin and its fragments, and/or a metalloproteinase, a peroxidase, and/or a phosphohydrolase. The second pharmaceutical composition promotes release of the compound from a platelet.

The second pharmaceutical composition may be administered after the pharmaceutical composition is administered, e.g., at least twice before the second pharmaceutical composition is administered.

A subject may be administered additional therapeutic agents in conjunction with the pharmaceutical compositions comprising loaded platelets. As an example, a subject may be administered platelets loaded with a VEGF inhibitor (e.g., Bevacizumab) and also administered Remdesivir; this may be used to treat Acute respiratory distress syndrome (ARDS), perhaps associated with COVID. A subject may be administered platelets loaded with one or both of a multikinase inhibitor (e.g., regorafenib) and fumagillin, and also administered a low-dose chemotherapy; this may be used for treating pancreatic cancer, lung cancer, or colon cancer. A subject may be administered platelets loaded with one or both of an EGFR inhibitor (e.g., Cetuximab) and a multikinase inhibitor (e.g., regorafenib) and also administered a low-dose chemotherapy; this may be used for treating lung cancer. A subject may be administered platelets loaded with one or both or all three of an EGFR inhibitor (e.g., Cetuximab), a multikinase inhibitor (e.g., regorafenib), and an ALK/ROS1/NTRK inhibitor (e.g., crizotinib) and also administered a low-dose chemotherapy; this may be used for treating non-small cell lung cancer.

The platelets may be loaded with a combination of two or more compounds of the present disclosure. As examples, the compounds may have first and second agents being a VEGF inhibitor (e.g., Bevacizumab) and a PDL1 inhibitor (e.g., Pembrolizumab); this may be used for treating pancreatic cancer. Also, a first and second agent may be a multikinase inhibitor (e.g., regorafenib) and fumagillin; this may be used for treating pancreatic cancer, lung cancer, or colon cancer.

The subject in need may have a disease or disorder selected from a cancer or an injury. Inflammation may be a symptom of the disease or disorder. The disease or disorder may be a side effect of an implant, graft, stent, or prosthesis. The disease or disorder may be caused by a defective gene.

Example 9: Illustrative Methods for Treating a Disease or Disorder by Administering to a Subject a Compound of the Present Disclosure In this example, a compound of the present disclosure is administered to a subject in need, e.g., who has a disease or a disorder.

Here, a subject in need is administered (e.g., by infusion or injection) a therapeutically-effective amount of a pharmaceutical composition comprising a compound of the present disclosure. In this method, the compound is loaded into a platelet in vivo.

Any agent listed in the present disclosure or known in the art may be used in this example. The agent may be an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet.

In some embodiments, the compound may comprise an agent selected from an EGFR inhibitor (e.g., Cetuximab), a VEGF inhibitor (e.g., Bevacizumab), a PDL1 inhibitor (e.g., Pembrolizumab), an FN1 inhibitor (e.g., Ocriplasmin), a multikinase inhibitor (e.g., regorafenib), a FGFR2 antagonist (e.g., thalidomide), thrombin and its analogues, CSF3R agonist (e.g., Filgrastim), PSMB5 inhibitor (e.g., Bortezomib), fumagillin, or an ALK/ROS1/NTRK inhibitor (e.g., crizotinib). The subject may be administered more than one compound; the additional compounds may have an agent selected from the immediately above list or from any agent known in the art, e.g., an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase (agonist or inhibitor), or a factor that inhibits cellular proliferation, angiogenesis, inflammation, immunity, or another physiological process mediated by or associated with a platelet.

The subject may further be administered a second pharmaceutical composition comprising one or more of heparanase, thrombin and its fragment peptides, a protease-activated receptor 1 (PAR1) agonist or antagonist peptide, a protease-activated receptor 4 (PAR4) agonist or antagonist peptide, plasmin and its fragments, and/or a metalloproteinase, a peroxidase, and/or a phosphohydrolase. The second pharmaceutical composition promotes release of the compound from a platelet.

The second pharmaceutical composition may be administered after the pharmaceutical composition is administered, e.g., at least twice before the second pharmaceutical composition is administered.

A subject may be administered additional therapeutic agents in conjunction with the pharmaceutical compositions comprising a compound of the present disclosure. Additional therapeutic agents may be Remdesivir and/or a low-dose chemotherapy.

The subject in need may have a disease or disorder selected from a cancer or an injury. Inflammation may be a symptom of the disease or disorder. The disease or disorder may be a side effect of an implant, graft, stent, or prosthesis. The disease or disorder may be caused by a defective gene.

What is claimed is:

1. A compound comprising a first agent and a first polypeptide, wherein the first polypeptide comprises a glycosaminoglycan (GAG)-binding peptide which is capable of binding a GAG in an alpha granule of a platelet; wherein the GAG-binding peptide binds to chondroitin sulfate (CS) and/or heparan sulfate (HS); and wherein the GAG-binding peptide comprises an amino acid sequence of any one of SEQ ID NO: 1 to SEQ ID NO: 8 or SEQ ID NO: 10 to SEQ ID NO: 13.

2. The compound of claim 1, wherein the GAG-binding peptide binds to chondroitin sulfate A (CSA).

3. The compound of claim 1, wherein the GAG-binding peptide binds to heparan sulfate (HS), serglycin, perlecan, dermatan sulfate, keratan sulfate, and/or GPIIb/IIIa.

4. The compound of claim 1, wherein the GAG-binding peptide remains bound to a CS-containing column when exposed to about 1N NaCl, to about 2N NaCl, or to about 3 N NaCl.

5. The compound of claim 1, wherein the GAG-binding peptide is unbound to an HS-containing column, a serglycin-containing column, perlecan-containing column, dermatan sulfate-containing column, keratan sulfate-containing column, and/or GPIIb/IIIa-containing column when exposed to NaCl of between about 0.001N and about 0.01N, at least 0.1N, or at least 1N.

6. The compound of claim 1, wherein the first polypeptide consists of the GAG-binding peptide.

7. The compound of claim 1, wherein the N-terminal of the first polypeptide is directly or indirectly linked to the first agent and/or the C-terminal of the first polypeptide is directly or indirectly linked to the first agent.

8. The compound of claim 1, wherein the first agent comprises an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase agonist, a tyrosine kinase inhibitor, or a factor that inhibits cellular proliferation, angiogenesis, inflammation and immunity.

9. The compound of claim 8, wherein the first agent is harmful to mammalian cells and/or is toxic to a subject and/or the first agent is susceptible to degradation when administered directly into the bloodstream of a subject.

10. An isolated platelet comprising 1 to 1000 copies of the compound of claim 1.

11. The isolated platelet of claim 10, wherein the 1 to 1000 copies of the compound are loaded into an alpha granule of the platelet.

12. The isolated platelet of claim 10, further comprising an at least second compound wherein the at least second compound comprises an at least second agent and an at least second polypeptide, wherein the at least second polypeptide comprises an at least second glycosaminoglycan (GAG)-binding peptide which is capable of binding a GAG in an alpha granule of a platelet.

13. The isolated platelet of claim 12, wherein the at least second agent comprises an antibody, a chemotherapeutic agent, a cytotoxic compound, a small molecule, a fluorescent moiety, radioactive element, an immune checkpoint inhibitor, a growth factor, a growth inhibitor, a protease/proteinase, a coagulation factor, a lipid or phospholipid, an extracellular matrix protein, a hormone, an enzyme, a chemokine/chemoattractant, a neurotrophin, a tyrosine kinase agonist, a tyrosine kinase inhibitor, or a factor that inhibits cellular proliferation, angiogenesis, inflammation and immunity, and wherein the first agent is different from the at least second agent.

14. A pharmaceutical composition comprising the isolated platelet of claim 10 and one or more pharmaceutically-acceptable excipients.

15. A pharmaceutical composition comprising the isolated platelet of claim 12 and one or more pharmaceutically-acceptable excipients.

16. A method for treating a disease or disorder in a subject in need thereof, the method comprising a step of administering to the subject a therapeutically-effective amount of the pharmaceutical composition of claim 14.

17. A method for treating a disease or disorder in a subject in need thereof, the method comprising a step of administering to the subject a therapeutically-effective amount of the pharmaceutical composition of claim 15.

18. A pharmaceutical composition comprising:

a first isolated platelet comprising a first compound comprising a first agent and a first polypeptide, wherein the first polypeptide comprises a first glycosaminoglycan (GAG)-binding peptide which is capable of binding a first GAG in an alpha granule of the platelet;

an at least second isolated platelet comprising an at least second compound comprising an at least second agent and an at least second polypeptide, wherein the at least second polypeptide comprises an at least second GAG-binding peptide which is capable of binding an at least second GAG in an alpha granule of the platelet; and one or more pharmaceutically-acceptable excipients, wherein the first GAG-binding peptide and the at least second GAG-binding peptide comprises an amino acid sequence of any one of SEQ ID NO: 1 to SEQ ID NO: 8 or SEQ ID NO: 10 to SEQ ID NO: 13.

19. The pharmaceutical composition of claim 18, wherein the first and/or the at least second agents are independently selected from the group consisting of an antibody, a chemotherapeutic agent, a cytotoxic compound, a small molecule, a fluorescent moiety, a radioactive element, an immune checkpoint inhibitor, a growth factor, a growth inhibitor, a protease/proteinase, a coagulation factor, a lipid, a phospholipid, an extracellular matrix protein, a hormone, an enzyme, a chemokine, a chemoattractant, a neurotrophin, a tyrosine kinase agonist, a tyrosine kinase inhibitor, and a factor that inhibits cellular proliferation, angiogenesis, inflammation, or immunity.

20. A method for manufacturing a loaded platelet, the method comprising steps of:

obtaining a platelet, contacting the platelet in vitro or ex vivo with a compound of claim 1, and allowing contact between the platelet and the compound to progress until the compound is internalized by an alpha granule of the platelet, thereby producing a loaded platelet.

21. The method of claim 20, further comprising steps of:

contacting the platelet in vitro or ex vivo with an at least second compound, wherein the at least second compound comprises an at least second agent and an at least second polypeptide, wherein the at least second polypeptide comprises an at least second glycosaminoglycan (GAG)-binding peptide which is capable of binding a GAG in an alpha granule of a platelet; and allowing contact between the platelet and the at least second compound to progress until the at least second compound is internalized by an alpha granule of the platelet.

* * * * *

SEQUENCE LISTING

```
<160> NUMBER OF SEQ ID NOS: 14

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 1

Glu Arg Arg Ile Trp Phe Pro Tyr Arg Arg Phe
```

1 5 10

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Arg Phe Arg Trp Pro Tyr Arg Ile Arg Glu Phe
1 5 10

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Ala Arg Arg Ile Trp Phe Pro Tyr Arg Arg Phe
1 5 10

<210> SEQ ID NO 4
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 4

Glu Ala Arg Ile Trp Phe Pro Tyr Arg Arg Phe
1 5 10

<210> SEQ ID NO 5
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 5

Glu Arg Ala Ile Trp Phe Pro Tyr Arg Arg Phe
1 5 10

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 6

Glu Arg Arg Ala Trp Phe Pro Tyr Arg Arg Phe
1 5 10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 7

Glu Arg Arg Ile Ala Phe Pro Tyr Arg Arg Phe
1 5 10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 8

Glu Arg Arg Ile Trp Ala Pro Tyr Arg Arg Phe
1 5 10

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Glu Arg Arg Ile Trp Phe Ala Tyr Arg Arg Phe
1 5 10

<210> SEQ ID NO 10
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 10

Glu Arg Arg Ile Trp Phe Pro Ala Arg Arg Phe
1 5 10

<210> SEQ ID NO 11
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 11

Glu Arg Arg Ile Trp Phe Pro Tyr Ala Arg Phe
1 5 10

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 12

Glu Arg Arg Ile Trp Phe Pro Tyr Arg Ala Phe
1 5 10

<210> SEQ ID NO 13
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 13

Glu Arg Arg Ile Trp Phe Pro Tyr Arg Arg Ala
1 5 10

```
<210> SEQ ID NO 14
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 14

Glu Gly Gly Ile Trp Phe Pro Tyr Gly Gly Phe
1               5                   10
```